United States Patent [19]

Kuramoto et al.

[11] Patent Number: 5,245,037

[45] Date of Patent: Sep. 14, 1993

[54] QUINOLONE DERIVATIVES AND ANTIBACTERIAL AGENTS CONTAINING THE SAME

[75] Inventors: Yasuhiro Kuramoto; Masayasu Okuhira; Takashi Yatsunami, all of Hiroshima, Japan

[73] Assignee: Wakunaga Seiyaku Kabushiki Kaisha, Osaka, Japan

[21] Appl. No.: 497,885

[22] Filed: Mar. 23, 1990

[30] Foreign Application Priority Data

Mar. 31, 1989 [JP] Japan .................................. 1-82321
Sep. 13, 1989 [JP] Japan .................................. 1-238064

[51] Int. Cl.$^5$ ........................................ C07D 405/04
[52] U.S. Cl. ................................ 546/156; 540/597; 544/349; 544/105; 544/363; 546/16; 546/122; 546/113; 546/123
[58] Field of Search ................ 546/156; 540/597; 514/312, 213

[56] References Cited

U.S. PATENT DOCUMENTS

| | | | |
|---|---|---|---|
| 4,780,468 | 10/1988 | Bridges et al. | 546/156 |
| 4,786,649 | 11/1988 | Ueda et al. | 546/156 |
| 4,801,584 | 1/1989 | Yokose et al. | 544/66 |
| 4,851,418 | 7/1989 | Sanchez | 546/156 |
| 4,962,112 | 10/1990 | Rosen et al. | 546/156 |

FOREIGN PATENT DOCUMENTS

| | | |
|---|---|---|
| 153163 | 8/1985 | European Pat. Off. |
| 230948 | 8/1987 | European Pat. Off. |
| 2188317 | 9/1987 | United Kingdom |

OTHER PUBLICATIONS

J. Med. Chem., 29. 394–404 (1986).
J. Med. Chem., 29. 2363–2369 (1986).
Chemical Abstracts vol. 105, No. 25, Dec. 22, 1986, p. 787, Abstract No. 226520t, Columbus, Ohio, US; & JP-A-61148179 (Kokai Tokkyo Koho) May 7, 1986 European Search Report.

*Primary Examiner*—Bernard Dentz
*Assistant Examiner*—James H. Turnipseed
*Attorney, Agent, or Firm*—Oblon, Spivak, McClelland, Maier & Neustadt

[57] ABSTRACT

Antibacterial quinolone derivatives represented by the following formula [I] and salts thereof are disclosed.

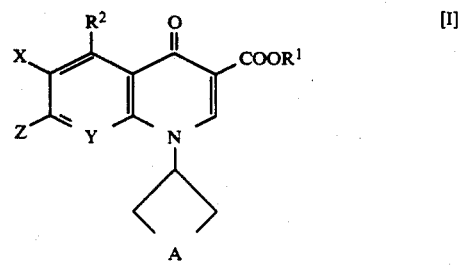

wherein $R^1$ means a hydrogen atom or a carboxyl-protecting group; $R^2$ denotes a hydrogen or halogen atom or a hydroxyl, lower alkoxyl, amino, aralkylamino, or mono- or di-(lower alkyl)amino group; A represents an oxygen or sulfur atom or N—$R^3$ in which $R^3$ is a hydrogen atom or an amino-protecting group; X is a hydrogen or halogen atom; Y means a nitrogen atom or C—$R^4$ in which $R^4$ is a hydrogen or halogen atom or a lower alkyl or lower alkoxyl group; and Z denotes a halogen atom or a substituted or unsubstituted heterocyclic group having at least one nitrogen atom as a hetero atom.

4 Claims, No Drawings

QUINOLONE DERIVATIVES AND ANTIBACTERIAL AGENTS CONTAINING THE SAME

BACKGROUND OF THE INVENTION

1) Field of the Invention

The present invention relates to novel quinolone derivatives and salts thereof, said derivatives and salts having excellent antibacterial activities, to preparation processes thereof and also to antibacterial agents containing the same.

2) Description of the Related Art

New quinolone agents having pyridonecarboxylic acid as a basic skeleton have excellent antibacterial activities and a broad antibacterial spectrum, so that they have attracted interests as synthetic antibacterial agents comparable with antibiotics. Among these, norfloxacin [Japanese Patent Application Laid-Open (Kokai) No. 141286/1978], enoxacin [Japanese Patent Application Laid-Open (Kokai) No. 31042/1980], ofloxacin [Japanese Patent Application Laid-Open (Kokai) No. 46986/1982], ciprofloxacin [Japanese Patent Application Laid-Open (Kokai) No. 76667/1983] and the like have already found wide-spread clinical utility as therapeutic agents for infectious diseases.

The new quinolone agents known to date are however not fully satisfactory either in antibacterial activities, oral absorption, long-acting property, side effects on central nervous system, etc. To solve these problems, investigations are now under way, especially on substituents on positions 1, 5, 6, 7 and 8 of the quinoline and naphthylidine skeletons.

SUMMARY OF THE INVENTION

With the foregoing in view, the present inventors have conducted an extensive investigation with a view toward providing clinically excellent synthetic antibacterial agents improved in the problems described above. As a result, it has been found that quinolone derivatives which have the quinoline or naphthylidine skeleton with an oxetane, thietane or azetidine ring introduced on position 1 thereof and are represented by the formula [I] to be described herein, have strong antibacterial activities against gram-negative and gram-positive bacteria and also a suitable hydrophilicity/hydrophobicity balance required for synthetic antibacterial agents, leading to the completion of the present invention.

The present invention therefore provides quinolone derivatives represented by the below-described formula [I] and salts thereof, their preparation processes and antibacterial agents containing them.

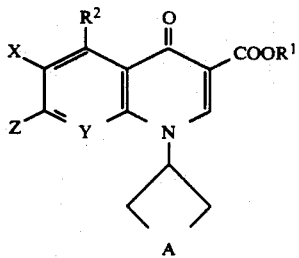

wherein $R^1$ means a hydrogen atom or a carboxyl-protecting group; $R^2$ denotes a hydrogen or halogen atom or a hydroxyl, lower alkoxyl, amino, aralkylamino, or mono- or di-(lower alkyl)amino group; A represents an oxygen or sulfur atom or $N-R^3$ in which $R^3$ is a hydrogen atom or an amino-protecting group; X is a hydrogen or halogen atom; Y means a nitrogen atom or $C-R^4$ in which $R^4$ is a hydrogen or halogen atom or a lower alkyl or lower alkoxyl group; and Z denotes a halogen atom or a substituted or unsubstituted heterocyclic group having at least one nitrogen atom as a hetero atom.

In the present invention, the term "lower" employed in the definition for some substituent groups in formula [I] means that the group referred to has 1-7, preferably 1-4 carbon atoms when the substituent group is a linear or branched group but has 3-7 carbon atoms when the substituent group is a cyclic group.

The compounds [I] and their salts according to the present invention are extremely valuable as antibacterial agents. They can therefore be used as drugs for human being and animals and also as drugs for fish diseases, agricultural chemicals and food preservatives.

DETAILED DESCRIPTION OF THE INVENTION AND PREFERRED EMBODIMENT

The term "carboxyl-protecting group" represented by $R^1$ indicates the ester residual group of a carboxylate ester and means a desired group capable of undergoing a relatively easy cleavage and yielding a corresponding free carboxyl group. Specific examples of the carboxyl-protecting group includes those removable upon treatment under mild conditions, such as hydrolysis or catalytic reduction, such as lower alkyl groups (e.g., methyl, ethyl, n-propyl, t-butyl, etc.), aralkyl groups (e.g., benzyl, etc.), and aryl groups (e.g., phenyl, etc.); and those readily removable in vivo, such as lower alkanoyloxy-lower a)ky) groups (e.g., acetoxymethyl, pivaloyloxymethyl, etc.), lower alkoxycarbonyloxy-lower alkyl groups (e.g., methoxycarbonyloxymethyl, 1-ethoxycarbonyloxyethyl, etc.), lower alkoxymethyl groups (e.g., methoxymethyl, etc.), lactonyl groups (phthalidyl, etc.), di(lower alkyl)amino-lower alkyl groups (e.g., 1-dimethylaminoethyl, etc.), (5-methyl-2-oxol-4-yl)methyl group, and the like.

Illustrative of the halogen atom represented by $R^2$ include F, Cl and Br, with F and Cl being preferred. Examples of the lower alkoxyl group indicated by $R^2$ include methoxy, ethoxy and isopropyloxy. Examples of the mono- or di-(lower alkyl)amino group include methylamino, ethylamino or dimethylamino. Examples of the aralkyl group represented by $R^2$ include benzyl and phenethyl.

When A is the group $N-R^3$, illustrative of the amino-protecting group denoted by $R^3$ include lower alkyl groups, lower alkenyl groups and the like as well as those employed as amino-protecting groups in usual peptide syntheses. More specific examples of the amino-protecting group include alkyloxycarbonyl groups (ethoxycarbonyl, t-butoxycarbonyl, etc.), acyl groups (acetyl, benzoyl, etc.), benzyl-type protecting groups (benzyl, benzhydryl, etc.), and the like. In addition, illustrative of the lower alkyl group include linear or branched alkyl groups having 1-7, preferably 1-4 carbon atoms, such as methyl, ethyl, n-propyl, isopropyl and t-butyl. Examples of the lower alkenyl group include linear and branched alkenyl groups having 2-7, preferably 2-5 carbon atoms, such as vinyl, allyl and 1-propenyl.

Exemplary halogen atoms represented by X include those mentioned above as $R^2$, with F and Cl being preferred. Of these, F is more preferred.

When Y is C—$R^4$, illustrative of the halogen atom represented by $R^4$ include F, Cl and Br, with F and Cl being preferred. Illustrative of the lower alkyl group indicated by $R^4$ include linear or branched alkyl groups having 1-7, preferably 1-4 carbon atoms, such as methyl, ethyl, n-propyl, isopropyl and t-butyl, with methyl being preferred.

Exemplary lower alkoxyl groups represented by $R^4$ include those mentioned above as $R^2$, with methoxy being preferred.

Exemplary halogen atoms represented by Z include those mentioned above as $R^2$, with F and Cl being preferred.

Further, the heterocyclic group represented by Z and containing at least one nitrogen atom as a hetero atom may be either a saturated heterocyclic group or an unsaturated heterocyclic group. It may be fused with another heterocyclic ring containing at least one nitrogen atom or with a benzene ring. Illustrative of the heterocyclic ring include heterocyclic groups containing 1-3 nitrogen atoms, such as residual groups of azetidine, pyrrolidine, pyrroline, pyrrole, imidazole, pyrazole, pyrazolidine, pyridine, pyrimidine, piperidine, piperazine, homopiperazine and triazole; heterocyclic groups containing as hetero atoms one nitrogen atom and another hetero atom selected from oxygen atom and sulfur atom, such as residual groups of thiazolidine, thiazole, morpholine and thiomorpholine; heterocyclic groups containing another heterocyclic ring or a benzene ring fused therewith, such as residual groups of indole, dihydroindole, isoindole, dihydroisoindole, isoindoline, naphthylidine, perhydronaphthylidine, pyrrolidino[1,2-a]piperazine, pyrrolidino[3,4-c]pyrrolidine and pyrrolidino[3,4-b]morpholine; and bicyclic heterocyclic groups such as residual groups of 2,5-diazabicyclo[2,2,1]heptane and 2,5-diazabicyclo[3,1,1]heptane.

Preferably, these heterocyclic groups are residual groups of 3-7 membered rings and the heterocyclic groups containing another heterocyclic ring or a benzene ring fused therewith are residual groups of 8-12 membered rings. They may be substituted with 1-4 suitable substituent groups. Exemplary substituent groups include nitro, hydroxyl and amino groups, halogen atoms, lower alkyl groups, cyclo-lower alkyl groups, lower alkoxyl groups, mono- or di-(lower alkyl)amino groups, cyclo-lower alkylamino groups, amino-lower alkyl groups, halo-lower alkyl groups, mono- or di-(lower alkyl)amino-lower alkyl groups, hydroxy-lower alkyl groups, alkoxy-lower alkyl groups, cyclo(-lower alkyl)amino-lower alkyl groups, substituted or unsubstituted acyloxy groups, lower alkylthio groups, substituted or unsubstituted aryl groups, cyano-lower alkyl groups, substituted or unsubstituted acylamino groups, substituted or unsubstituted alkoxycarbonylamino groups, substituted or unsubstituted alkoxycarbonyl groups, substituted or unsubstituted amino-(cyclo-lower alkyl) groups, substituted or unsubstituted acylamino-lower alkyl groups, substituted or unsubstituted alkoxycarbonylamino-lower alkyl groups, lower alkenyl groups, cyano group, mercapto group, formimidoyl group, lower alkylimidoyl groups, formimidoylamino group, lower alkylimidoylamino groups, substituted or unsubstituted aralkyl groups or lower alylidene groups, and mono- or di-(lower alkyl)hydrazino groups. These substituent groups may be bonded to on the same atom or different atoms in each heterocyclic group.

The heterocyclic group represented by Z and containing at least one nitrogen atom as a hetero atom may be bonded to the quinolone skeleton at any one of the ring-forming atoms thereof. Preferred examples include the following heterocyclic rings bonded to the quinolone skeleton at a nitrogen atom thereof:

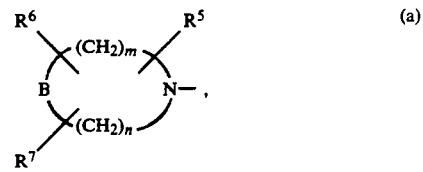

(a)

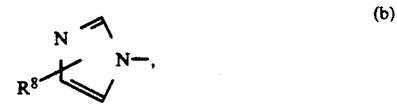

(b)

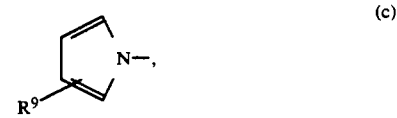

(c)

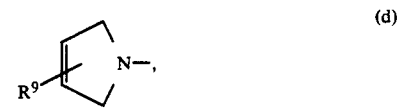

(d)

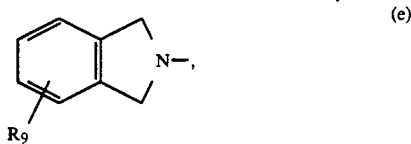

(e)

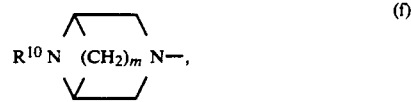

(f)

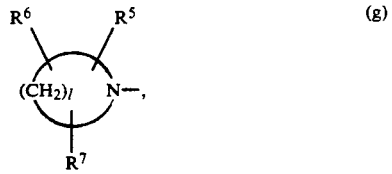

(g)

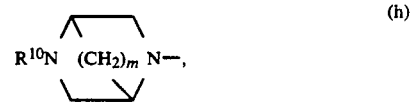

(h)

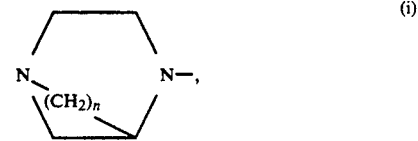

(i)

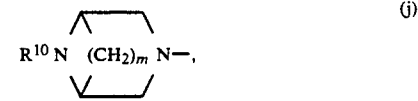

(j)

-continued

 (k)

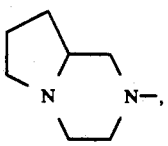 (l)

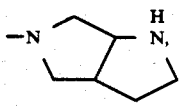 (m)

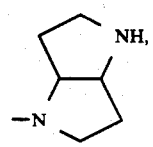 (n)

 (o)

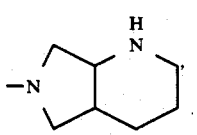 (p)

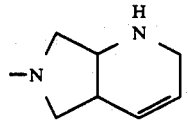 (q)

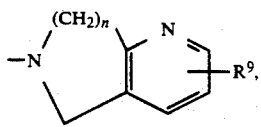 (r)

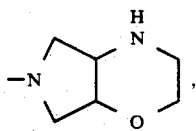 (s)

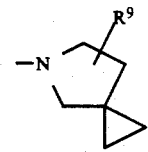 (t)

wherein B means an oxygen atom, a sulfur atom, —NR-$^{10}$— or

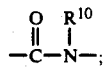

$R^5$, $R^6$ and $R^7$ may be the same or different and individually denote a hydrogen or halogen atom or a hydroxyl, amino, lower alkyl, halo-lower alkyl, substituted or unsubstituted mono- or di-(lower alkyl)amino, cyclo(lower alkyl)amino, amino-lower alkyl, substituted or unsubstituted mono- or di(lower alkyl)amino-lower alkyl, cyclo(lower alkyl)amino-lower alkyl, substituted or unsubstituted alkoxyl, substituted or unsubstituted acyloxy, lower alkylthio, substituted or unsubstituted aryl, cyano-lower alkyl, substituted or unsubstituted acylamino, substituted or unsubstituted alkoxycarbonyl, substituted or unsubstituted amino(cyclo-lower alkyl), substituted or unsubstituted acylamino-lower alkyl, substituted or unsubstituted alkoxycarbonylamino-lower alkyl, hydroxy-lower alkyl, substituted or unsubstituted alkoxy-lower alkyl, lower alkenyl, cyano, mercapto, formimidoylamino, or lower alkylimidoylamino group, $R^8$ represents a hydrogen atom or a lower alkyl group, $R^9$ is a hydrogen or halogen atom or a nitro, substituted or unsubstituted lower alkyl, amino, amino-lower alkyl, mono- or di-(lower alkyl)amino-lower alkyl, lower alkoxyl, hydroxyl, substituted or unsubstituted mono- or di-(lower alkyl)amino, formimidoylamino, or a lower alkylimidoylamino group, $R^{10}$ means a hydrogen atom or a substituted or unsubstituted lower alkyl, substituted or unsubstituted cyclo-lower alkyl, substituted or unsubstituted aralkyl, substituted or unsubstituted aryl, substituted or unsubstituted lower alkenyl, substituted or unsubstituted acyl, substituted or unsubstituted alkoxycarbonyl, hydroxy-lower alkyl, formimidoyl, or lower alkylimidoyl group, m stands for 1, 2 or 3, n denotes 1 or 2, and l is 3, 4 or 5.

As $R^5$, $R^6$ and $R^7$, may be mentioned, for example, halogen atoms (e.g., F, Cl, etc.), hydroxyl, amino, substituted or unsubstituted mono- or di(lower alkyl)amino groups (e.g., methylamino, ethylamino, n-propylamino, dimethylamino, diethylamino, benzylamino, benzylethylamino, benzylamino, benzylethylamino, pyrrolidinyl, piperidinyl, hydroxyethylamino, methoxyethylamino, fluoroethylamino, etc.), cyclo(lower alkyl)amino groups (e.g., cyclopropylamino, cyclopentylamino, etc.), lower alkyl groups (e.g., methyl, ethyl, n-propyl, etc.), halo-lower alkyl groups (e.g., fluoromethyl, trifluoromethyl, etc.), amino-lower alkyl groups (e.g., aminomethyl, 1-aminoethyl, 2-aminoethyl, 1-amino-1-methylethyl, etc.), substituted or unsubstituted mono- or di(lower alkyl)amino-lower alkyl groups (e.g., methylaminomethyl, ethylaminomethyl, dimethylaminomethyl, diethylaminomethyl, n-propylmethylaminomethyl, di(n-propyl)aminomethyl, isopropylaminomethyl, methylaminoethyl, dimethylaminoethyl, methylamino-n-propyl, diethylaminoethyl, dimethylamino-n-propyl, pyrrolidinylmethyl, benzylaminomethyl, benzylmethylaminomethyl, 2-fluoroethylaminomethyl, 2-hydroxyethylaminomethyl, 2-methoxyethylaminomethyl, 2-aminoethylaminomethyl, etc.), cyclo(lower alkyl)amino-lower alkyl groups (e.g., cyclopropylaminomethyl, etc.), substituted or unsubstituted alkoxyl groups (e.g., methoxy, ethoxy, n-propoxy, phenoxy, p-chlorophenoxy, p-fluorophenoxy, benzyloxy, etc.), substituted or unsubstituted acyloxy groups (e.g., acetoxy, benzoyloxy, etc.), lower alkylthio groups (e.g., methylthio, ethylthio, etc.), substituted or unsubstituted aryl groups (e.g., phenyl, p-fluorophenyl, p-methoxyphenyl, etc.), cyano-lower alkyl groups (e.g., cyanomethyl), substituted or unsubstituted alkoxycarbonylamino groups (e.g., t-butoxycarbonylamino, etc.), substituted or unsubstituted acylamino groups (e.g., acetyl, benzoyl, etc.), substituted or unsubstituted alkoxycarbonyl groups (e.g., methoxycarbonyl, ethoxycarbonyl, etc.), substituted or unsubstituted aminocyclo-lower alkyl groups (e.g., 1-aminocyclopropyl, etc.), substituted or unsubstituted acylamino-lower alkyl groups (e.g., acetylamino, etc.), substituted or unsubstituted alkoxycarbonylamino-lower alkyl groups (e.g., t-butoxycarbonylaminomethyl, benzyloxycarbonylaminomethyl, etc.), hydroxy-lower alkyl groups (e.g., hydroxymethyl, etc.), substituted or unsubstituted alkoxy-lower alkyl groups (e.g., methoxymethyl, etc.), lower alkenyl groups (e.g., vinyl, allyl, etc.), lower alkylidene groups (e.g., methylene, ethylidene, etc.), cyano, mercapto, formimidoyl, lower alkylimidoyl groups (e.g., acetimidoyl, etc.), formimidoylamino, lower alkylimidoylamino groups (e.g., acetimidoylamino, etc.), mono- or di0(lower alkyl)hydrazino groups (e.g., 2-methylhydrazino, etc.) and the like.

As described above, $R^{10}$ represents a hydrogen atom, a substituted or unsubstituted alkyl group, substituted or unsubstituted cyclo-lower alkyl group, substituted or unsubstituted aralkyl group, substituted or unsubstituted aryl group, substituted or unsubstituted alkenyl group, substituted or unsubstituted acyl group, substituted or unsubstituted alkoxycarbonyl group, hydroxy-lower alkyl group, formimidoyl group, or lower alkylimidoyl group. Typical examples of $R^{10}$ are as follows. Illustrative of the lower alkyl group include methyl, ethyl, n-propyl, isopropyl, n-butyl and t-butyl. Exemplary cyclo-lower alkyl groups include cyclopropyl, cyclopentyl and cyclohexyl. Examples of the aralkyl group include benzyl, phenylethyl and phenylpropyl. Exemplary aryl groups include phenyl. Illustrative of the lower alkenyl group include allyl, 2-butenyl, 3-methyl-2-butenyl and 3-butenyl. These groups may be substituted by 1–3 substituents selected from the class consisting of halogen atoms (e.g., F, Cl, etc.), hydroxy, substituted or unsubstituted amino groups (e.g., amino, methylamino, dimethylamino, ethylamino, acetamido, ethoxycarbonylamino, etc.), substituted or unsubstituted alkoxyl groups (e.g., methoxy, ethoxy, phenoxy, benzyloxy, p-bromobenzyloxy, etc.), lower alkyl groups (e.g., methyl, ethyl), carboxy, lower alkoxycarbonyl groups (e.g., methoxycarbonyl, ethoxycarbonyl, etc.), cyano, lower alkylthio groups (e.g., methylthio), substituted or unsubstituted phenyl groups (e.g., phenyl, p-fluorophenyl, p-methoxyphenyl, etc.), substituted or unsubstituted acyl groups (e.g., formyl, acetyl, n-propionyl, benzoyl, etc.), and the like.

Exemplary lower alkyl groups represented by $R^8$ include methyl, ethyl, n-propyl, isopropyl and t-butyl.

Exemplary substituted or unsubstituted lower alkyl groups represented by $R^9$ include methyl, ethyl, aminomethyl, methylaminomethyl, dimethylaminomethyl, ethylaminomethyl and hydroxymethyl. Illustrative examples of the substituted or unsubstituted mono- or di-(lower alkyl)amino group also represented by $R^9$ include methylamino, ethylamino and dimethylamino.

Illustrative of the heterocyclic group of the formula (a) include piperazinyl, morpholino, thiomorpholino, homopiperazinyl, thiazolidinyl, oxazolidinyl and 3-oxo-1-piperazinyl.

Illustrative of the bicyclic heterocyclic groups represented by the formulae (f), (h)-(j), (r) and (t) include the following groups:

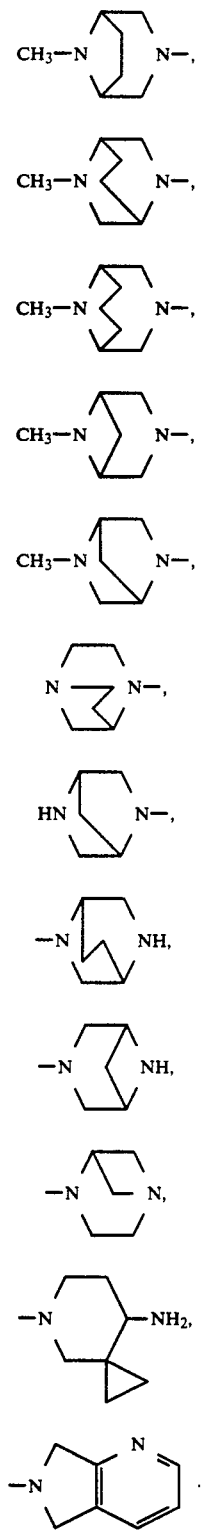

Exemplary heterocyclic groups represented by the formula (g) include residual groups of azetidine, pyrrolidine and piperidine.

Preferred specific examples of the heterocyclic group designated by the formulae (a) and (g) are as follows:

3-hydroxyazetidinyl, 3-aminoazetidinyl, 2-(N-t-butoxycarbonylamino)azetidinyl, 3-acetylaminoazetidinyl, 3-methylaminoazetidinyl, 3-dimethylaminoazetidinyl, 3-aminomethylazetidinyl, pyrrolidinyl, 3-hydroxypyrrolidinyl, 3,4-dihydroxypyrrolidinyl, 3-methoxypyrrolidinyl, 3-methylpyrrolidinyl, 3-hydroxy-4-methylpyrrolidinyl, 3-aminopyrrolidinyl, 3-methylaminopyrrolidinyl, 3-dimethylaminopyrrolidinyl, 3-ethylaminopyrrolidinyl, 3-diethylaminopyrrolidinyl, 3-acetylaminopyrrolidinyl, 3-t-butoxycarbonylaminopyrrolidinyl, 3-(N-acetyl)methylaminopyrrolidinyl, 3-(t-butoxycarbonyl)methylaminopyrrolidinyl, 3-aminomethylpyrrolidinyl, 3-methylaminomethylpyrrolidinyl, 3-dimethylaminomethylpyrrolidnyl, 3-ethylaminomethylpyrrolidinyl, 3-diethylaminomethylpyrrolidinyl, 3-(N-acetyl)aminomethylpyrrolidinyl, 3-(t-butoxycarbonyl)aminomethylpyrrolidinyl, 3-(N-acetyl)methylaminomethylpyrrolidinyl, 3-(t-butoxycarbonyl)methylaminomethylpyrrolidinyl, 3-(1-aminoethyl)pyrrolidinyl, 3-(2-aminoethyl)pyrrolidinyl, 3-(1-amino-1-methylethyl)pyrrolidinyl, 3-(1-methylaminoethyl)pyrrolidinyl, 3-(1-dimethylaminoethyl)pyrrolidinyl, 3-amino-4-methylpyrrolidinyl, 3-amino-5-methylpyrrolidinyl, 3-methylamino-4-methylpyrrolidinyl, 3-dimethylamino-4-methylpyrrolidinyl, 3-ethylamino-4-methylpyrrolidinyl, 3-diethylamino-3-methylpyrrolidinyl, 3-diethylamino-4-methylpyrrolidinyl, 3-aminomethyl-4-methylpyrrolidinyl, 3-methylaminomethyl-4-methylpyrrolidinyl, 3-dimethylaminomethyl-4-methylpyrrolidinyl, 3-ethylaminomethyl-4-methylpyrrolidinyl, 3-(1-aminoethyl)-4-methylpyrrolidinyl, 3-(2-aminoethyl)-4-methylpyrrolidinyl, 3-amino-4-ethylpyrrolidinyl, 3-methylamino-4-ethylpyrrolidinyl, 3-dimethylamino-4-ethylpyrrolidinyl, 3-ethylamino-4-ethylpyrrolidinyl, 3-diethylamino-4-ethylpyrrolidinyl, 3-aminomethyl-4-ethylpyrrolidinyl, 3-methylaminomethyl-4-ethylpyrrolidinyl, 3-dimethylaminomethyl-4-ethylpyrrolidinyl, 3-amino-3-methylpyrrolidinyl, 3-methylamino-3-methylpyrrolidinyl, 3-dimethylamino-3-methylpyrrolidinyl, 3-amino-3,4-dimethylpyrrolidinyl, 3-amino-4,4-dimethylpyrrolidinyl, 3-amino-4,5-dimethylpyrrolidinyl, 3-amino-2,4-dimethylpyrrolidinyl, 3-methylamino-3,4-dimethylpyrrolidinyl, 2-methyl-3-aminopyrrolidinyl, 2-methyl-3-dimethylaminopyrrolidinyl, 3-amino-4-vinylpyrrolidinyl, 3-amino-4-methoxypyrrolidinyl, 3-amino-4-methoxymethylpyrrolidinyl, 3-methylamino-4-methoxypyrrolidinyl, 3-dimethylamino-4-methoxypyrrolidinyl, 3-ethylamino-4-methoxypyrrolidinyl, 3-diethylamino-4-methoxypyrrolidinyl, 3-benzylamino-4-methoxypyrrolidinyl, 3-aminomethyl-4-methoxypyrrolidinyl, 3-methylaminomethyl-4-methoxypyrrolidinyl, 3-dimethylaminomethyl-4-methoxypyrrolidinyl, 3-ethylaminomethyl-4-methoxypyrrolidinyl, 3-aminomethyl-3-methoxypyrrolidinyl, 3-methylaminomethyl-3-methoxypyrrolidinyl, 3-dimethylaminomethyl-3-methoxypyrrolidinyl, 3-amino-4-ethoxypyrrolidinyl, 3-dimethylamino-4-ethoxypyrrolidinyl, 3-methylamino-4-ethoxypyrrolidinyl, 3-aminomethyl-4-ethoxypyrrolidinyl, 3-dimethylaminomethyl-4-ethoxypyrrolidinyl, 3-amino-4-aminocarbonylpyrrolidinyl, 3-amino-4-dimethylaminocarbonylpyrrolidinyl, 3-amino-4-hydroxypyrrolidinyl, 3-amino-4-hydroxymethylpyrrolidinyl, 3-amino-4-methyl-4-hydroxymethylpyrrolidinyl, 3-amino-4-hydroxyethylpyrrolidinyl, 3-aminomethyl-4-hydroxypyrrolidinyl, 3-dimethylaminomethyl-4-hydroxypyrrolidinyl, 3,4-dihydroxypyrrolidinyl, 3,4-dimethoxypyrrolidinyl, 3-hydroxy-4-methylpyrrolidinyl, 3-amino-4-fluoropyrrolidinyl, 3-amino-4-fluoromethylpyrrolidinyl, 3-amino-4-trifluoromethylpyrrolidinyl, 3-methylamino-4-fluoropyrrolidinyl, 3-dimethylamino-4-fluoropyrrolidinyl, 3-aminomethyl-4-fluoropyrrolidinyl, 3-methylaminomethyl-4-fluoropyrrolidinyl, 3-dimethylaminomethyl-4-fluoropyrrolidinyl, 3-methylamino-4-chloropyrrolidinyl, 3-aminomethyl-4-chloropyrrolidinyl, 3-methylaminomethyl-4-chloropyrrolidinyl, 3-(2-hydroxyethyl)aminomethylpyrrolidinyl, 3-(2-fluoroethyl)aminomethylpyrrolidinyl, 3-amino-4-methylthiopyrrolidinyl, 3-amino-4-methylsulfinylpyrrolidinyl, 3-formimidoylaminopyrrolidinyl, 3-(2-dimethylhydrazino)pyrrolidinyl, 3-amino-4-methylenepyrrolidinyl, piperazinyl, 4-methylpiperazinyl, 3-methylpiperazinyl, 2-methylpiperazinyl, 3,4-dimethylpiperazinyl, 3,5-dimethylpiperazinyl, 3,3-dimethylpiperazinyl, 3,4,5-trimethylpiperazinyl, 4-ethoxycarbonypiperazinyl, 4-t-butoxycarbonylpiperazinyl, 4-acetylpiperazinyl, 4-benzyloxycarbonylpiperazinyl, 4-ethylpiperazinyl, 3,4-diethylpiperazinyl, 3,4,5-triethylpiperazinyl, 4-ethyl-3,5-dimethylpiperazinyl, 3-methyl-4-acetylpiperazinyl, 3-methyl-4-t-butoxycarbonylpiperazinyl, 4-benzylpiperazinyl, 4-n-propylpiperazinyl, 4-isopropylpiperazinyl, 4-t-butylpiperazinyl, 4-cyclopropylpiperazinyl, 4-cyclopentylpiperazinyl, 4-cyclopropylmethylpiperazinyl, 4-phenylpiperazinyl, 4-(p-dimethylaminophenyl)piperazinyl 4-(p-methoxyphenyl)piperazinyl, 4-(p-fluorophenyl)piperazinyl 3-phenylpiperazinyl, 3-(p-fluorophenyl)piperazinyl 3-(p-chlorophenyl)piperazinyl, 3-(p-hydroxyphenyl)piperazinyl 3-(p-methylphenyl)piperazinyl, 4-hydroxyethylpiperazinyl, 4-aminoethylpiperazinyl, 4-allylpiperazinyl, 4-cinnamylpiperazinyl, 4-cyanoethylpiperazinyl, 4-carboxyethylpiperazinyl, 4-carboxymethylpiperazinyl, 4-(1,2-dicarboxyethyl)piperazinyl, 4-hydroxypiperazinyl, 4-aminopiperizinyl, 3-fluoromethylpiperazinyl, 3-trifluoromethylpiperazinyl, 4-formimidoylpiperazinyl, 4-acetoimidoylpiperazinyl, 4-dimethylaminopiperizinyl, 4-hydroxypiperizinyl, morpholino, 2-aminomethylmorpholino, 2-methylaminomorpholino, 2-dimethylaminomorpholino, thiomorpholino, homopiperazinyl, 4-methylhomopiperazinyl, thiazolizinyl, 3-pyrrolinyl, 3-aminomethyl-3-pyrrolinyl, oxazolidinyl, imidazolyl and pyrrolyl.

The compounds [I] of the present invention can be converted into both acid addition salts and base addition salts. Exemplary acid addition salts include (a) the salts with mineral acids such as hydrochloric acid and sulfuric acid, (b) the salts with organic carboxylic acids such as formic acid, citric acid, trichloroacetic acid and trifluoroacetic acid, and (c) the salts with sulfonic acids such as methanesulfonic acid, benzenesulfonic acid, p-toluenesulfonic acid, mesitylenesulfonic acid and naphthalenesulfonic acid. On the other hand, illustrative base addition salts include (a) the salts with alkali metals such as sodium and potassium, (b) the salts with alkaline earth metals such as calcium and magnesium, (c) the ammonium salt, (d) the salts with nitrogen-containing organic bases such as trimethylamine, triethylamine, tributylamine, pyridine, N,N-dimethylaniline, N-methylpiperidine,N-methylmorpholine, diethylamine, cyclohexylamine, procaine, dibenzylamine, N-benzyl-β-phenethylamine, 1-ephenamine and N,N'-dibenzylethylenediamine.

The compounds [I] of the present invention may be not only in unsolvated forms but also in hydrated or solvated forms. The present invention therefore embraces the compounds [I] in any crystalline forms and their hydrated and solvated products Further, the compounds [I] of the present invention include those containing an asymmetric carbon atom in a substituent group on position 7. They can exist as optically active substances. These optically active substances are also embraced in the compounds of the present invention.

The compounds [I] of the present invention also include those containing two asymmetric carbon atoms in a substituent group on position 7. They can exist as different stereoisomers (cis-form, trans-form). These stereoisomers are also included in the compounds of the present invention.

Each compound [I] of the present invention can be prepared by a process suited for the types of its substituent groups. Preferred preparation processes are as follows:

Process 1

The compounds of the formula [I] in which $R^1$ is a hydrogen atom or a lower alkyl group can be prepared, for example, by the series of steps shown in the following reaction scheme (1):

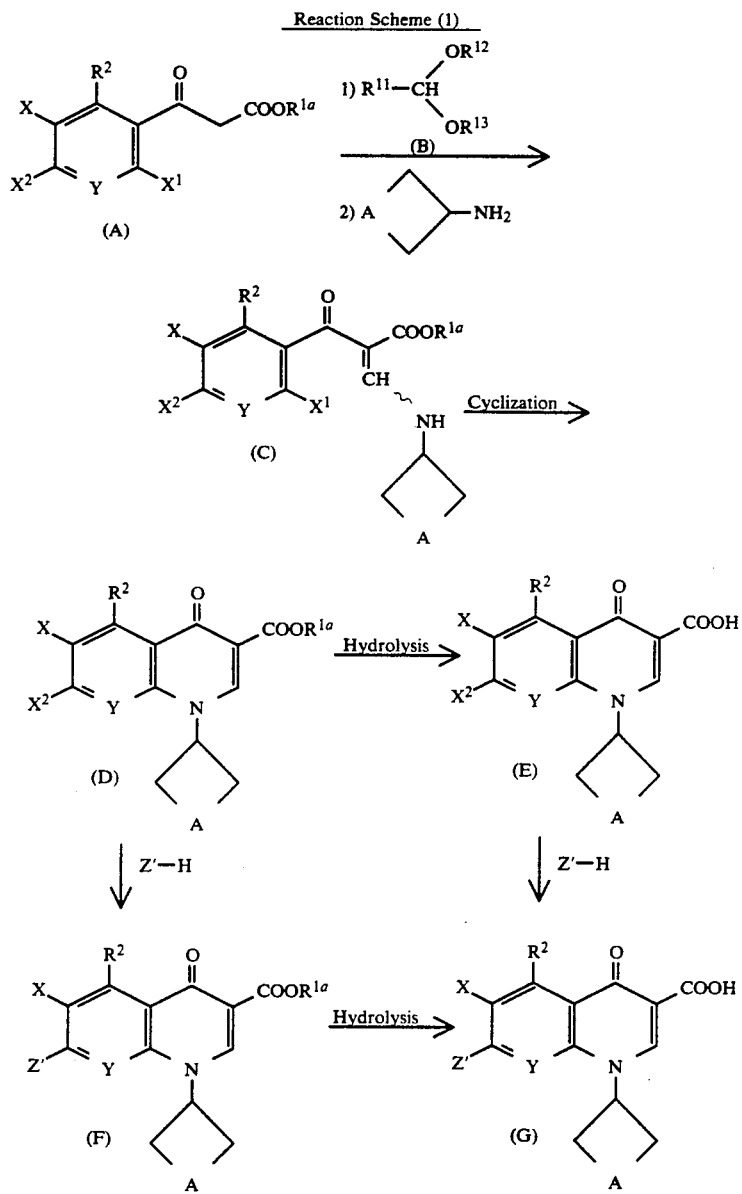

wherein $R^2$, X, Y and A have the same meanings as defined above, $X^1$ and $X^2$ individually mean a halogen atom, $R^{1a}$ denotes a lower alkyl group, $R^{11}$ represents a lower alkoxyl group or a group

in which $R^{14}$ and $R^{15}$ individually mean a lower alkyl group, $R^{12}$ and $R^{13}$ individually mean a lower alkyl group, and Z' is any one of the groups defined above for Z other than the halogen atoms.

The compound (C) can be obtained by reacting an orthoformic acid ester such as ethyl orthoformate or methyl orthoformate with the compound (A) in acetic anhydride and then reacting the resulting product with the compound

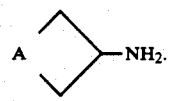

The reaction between the compound (A) and the orthoformic acid ester is conducted generally at 0°–160° C., preferably at 50°–150° C. The reaction time is generally 10 minutes to 48 hours, preferably 1–10 hours. The orthoformic acid ester can be used in at least an equimolar amount, notably in a molar amount 1 to about 10 times relative to the compound (A). The subsequent reaction with the

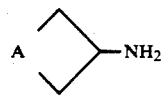

is conducted in a suitable solvent. Any solvent can be used here as long as it does not affect the reaction. Exemplary solvents include aromatic hydrocarbons such as benzene, toluene and xylene; ethers such as diethyl ether, tetrahydrofuran, dioxane, monoglyme and diglyme; aliphatic hydrocarbons such as pentane, hexane, heptane and ligroin; halogenated hydrocarbons such as methylene chloride, chloroform and carbon tetrachloride; dipolar aprotic solvent such as dimethylformamide, dimethylsulfoxide; and alcohols such as methanol, ethanol and propanol. The reaction is conducted generally at 0°–150° C., preferably 0°–100° C. The reaction time generally ranges from 10 minutes to 48 hours. The compound

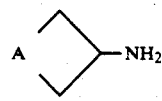

can be used in at least an equimolar amount, preferably in a molar amount 1–2 times relative to the compound (A).

As an alternative, the compound (C) may be obtained by reaction of compound (a) with an acetal such as N,N-dimethylformamide dimethyl acetal or N,N-dimethylformamide diethyl acetal, followed by the reaction with the compound

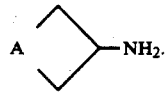

Any solvent may be used for the reaction with the acetal as long as it is inert to the reaction. The above-exemplified solvents can be mentioned by way of example. The reaction is conducted generally at 0°–150° C., preferably at room temperature–100° C. The reaction time is generally from 10 minutes to 48 hours, with 1–10 hours being preferred.

The cyclization reaction of the compound (C) is conducted in a suitable solvent in the presence of a basic compound. Any solvent can be used for this reaction as long as it does not affect the reaction. Exemplary solvents include aromatic hydrocarbons such as benzene, toluene and xylene; ethers such as diethyl ether, tetrahydrofuran, dioxane and monoglyme; halogenated hydrocarbons such as methylene chloride, chloroform and carbon tetrachloride; alcohols such as methanol, ethanol, propanol and butanol; and dipolar aprotic solvents such as dimethylformamide and dimethylsulfoxide. Illustrative usable basic compounds include alkali metals such as metallic sodium and metallic potassium; metal hydrides such as sodium hydride and calcium hydride; inorganic bases such as sodium hydroxide, potassium hydroxide and sodium carbonate; alkoxides such as sodium methoxide, sodium ethoxide and potassium t-butoxide; metal fluorides such as sodium fluoride and potassium fluoride; and organic bases such as triethylamine and 1,8-diazabicyclo[5.4.0]undecene (DBU). The reaction temperature of this reaction is generally 0°–200° C., preferably from room temperature to 180° C. The reaction can be brought to completion usually in 5 minutes to 24 hours. The basic compound may be used in an amount of at least an equimolar amount, preferably in a molar amount 1–2 times relative to the compound (C).

The hydrolysis of each of the compounds (D) and (F) can be conducted under the reaction conditions which are employed in usual hydrolysis reactions. For example, the hydrolysis may be carried out in the presence of a basic compound such as sodium hydroxide, potassium hydroxide, sodium carbonate or potassium carbonate, a mineral acid such as hydrochloric acid, sulfuric acid or hydrobromic acid or an organic acid such as p-toluenesulfonic acid and in a solvent, e.g., water, an alcohol such as methanol, ethanol or propanol, an ether such as tetrahydrofuran or dioxane, a ketone such as acetone or methyl ethyl ketone, or acetic acid, or a mixed solvent thereof. This reaction is conducted generally at room temperature to 180° C, preferably from room temperature to 140° C. The reaction time generally ranges from 1 hour to 24 hours.

The compounds (F) and (G) can be obtained by reacting Z'—H to the compounds (D) and (E), respectively. These reactions are conducted at room temperature to 160° C. in a solvent which does not give influence to the reactions, for example, an aromatic hydrocarbon such as benzene, toluene or xylene, an alcohol such as methanol or ethanol, an ether such as tetrahydrofuran, dioxane or monoglyme, a halogenated hydrocarbon such as methylene chloride, chloroform or carbon tetrachloride, a dipolar aprotic solvent such as dimethylformamide, dimethylsulfoxide or N-methylpyrrolidone, acetonitrile, or pyridine, and if necessary, in the presence of an acid-neutralizing agent such as sodium carbonate, calcium carbonate, sodium hydrogencarbonate or triethylamine 1,8-diazabicyclo[5.4.0]undecene (DBU). The reaction time may range from several minutes to 48 hours, preferably from 10 minutes to 24 hours. Z'—H may be used in at least an equimolar amount, preferably in a molar amount 1–5 times relative to the compound (D) or compound (E).

When the starting compounds employed in the above reactions, namely, the starting compounds

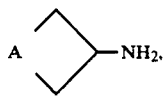

Z'—H and/or (A) contain one or more reactive groups which do not take part in the reactions, such as amino, imino, hydroxyl, mercapto and/or carboxyl groups, these starting compounds may be used in a form with these groups being protected, followed by the removal of the protecting groups by a method known per se after completion of the reaction. Any protecting groups can be used as long as they can be removed without destroying the structure of the compound of the present invention to be formed by the reaction. Groups usually employed in the chemical field of peptides, aminosaccharides and nucleic acids can be used.

The starting compound (A) can be prepared by any one of the processes described in the following publications or by a similar process.

1) J. Heterocyclic Chem. 22, 1033 (1985).
2) Liebigs Ann. Chem. 29 (1987).
3) J. Med. Chem. 31, 991 (1988).
4) J. Org. Chem. 35, 930 (1970).
5) Japanese Patent Application Laid-Open (Kokai) No. 246541/1987.
6) Japanese Patent Application Laid-Open (Kokai) No. 26272/1987.
7) Japanese Patent Application Laid-Open (Kokai) No. 145268/1988.
8) J. Med. Chem. 29, 2363 (1986).
9) J. Fluorin Chem. 28, 361 (1985).
10) Japanese Patent Application Laid-Open (Kokai) No. 198664/1988.
11) Japanese Patent Application Laid-Open (Kokai) No. 264461/1988.
12) Japanese Patent Application Laid-Open (Kokai) No. 104974/1988.
13) Eur. Pat. App. EP 230948.
14) Japanese Patent Application Laid-Open (Kokai) No. 28157/1990.

Process 2

Of the compounds represented by the formula [I], those in which $R^2$ is a hydroxyl, amino or mono(lower alkyl)amino group and, in addition, $R^1$ is a hydrogen atom or lower alkyl group can also be prepared by the steps shown in the following reaction scheme (2):

Reaction Scheme (2)

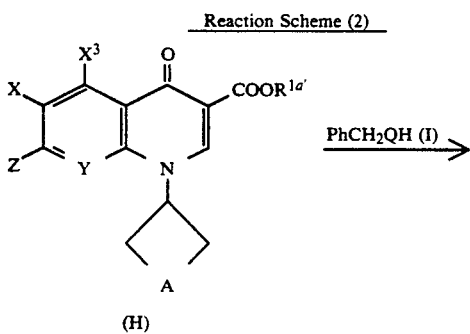

(H)

PhCH$_2$QH (I) →

-continued
Reaction Scheme (2)

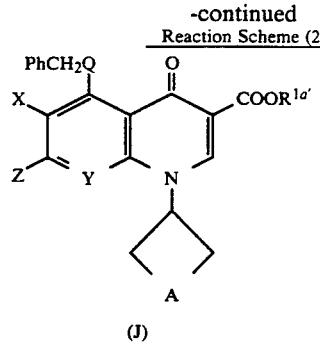

(J)

Debenzylation →

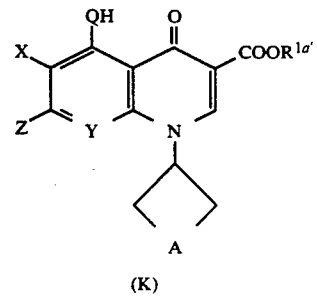

(K)

wherein $R^{1a'}$, X and Z have the same meanings, $X^3$ means a halogen atom, preferably F, and Q represents —O—, —NH— or —NR$^{16}$— in which $R^{16}$ is a lower alkyl group.

The compound (J) can be obtained by reacting the compound represented by the formula (H) with the compound (I), and if necessary, in the presence of an acid-neutralizing agent. Solvents which are usable in this reaction are those giving no influence to the reaction, including aromatic hydrocarbons such as toluene and xylene, ethers such as tetrahydrofuran, dioxane and monoglyme, halogenated hydrocarbons such as methylene chloride and chloroform, dipolar aprotic solvents such as dimethylformamide and dimethylsulfoxide, acetonitrile and pyridine. The reaction temperature may be usually 0°-150° C., preferably from room temperature to about 120° C. The reaction can generally be brought to completion approximately in 10 minutes to 24 hours.

The compound (I) may be used in at least an equimolar amount, preferably in a molar amount 1-1.5 times relative to the compound (H). As the acid-neutralizing agent, it is possible to employ the same acid-neutralizing agent as that usable in the reaction of the compound (D) or compound (E) with Z'—H.

For the debenzylation of the compound (J), the reaction conditions employed in any usual catalytic reduction can be applied. It can be conducted, for example, by stirring the compound (J) in the presence of a catalyst such as palladium/carbon, palladium black or platinum dioxide, in a solvent such as methanol, ethanol, propanol, acetic acid, tetrahydrofuran, dioxane, ethyl acetate or water or in a mixed solvent thereof, generally under the atmosphere of hydrogen gas at a pressure of 1-100 atm. The reaction temperature generally ranges from room temperature to 100° C. The reaction is generally brought to completion in 1-48 hours.

Process 3

Among the compounds represented by the formula [I], those having a hydrogen atom or a lower alkyl group as $R^1$ and a hydroxyl, lower alkoxyl, amino, or mono- or di-lower alkyl group as $R^2$ can also be prepared by the reaction step shown in the following reaction scheme (3):

Reaction Scheme (3)

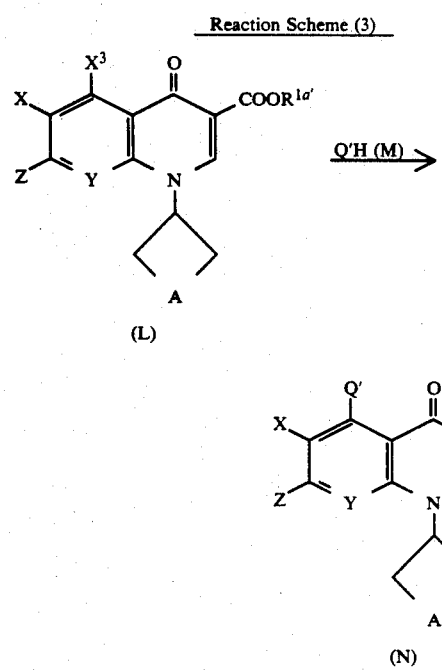

wherein $R^{1a'}$, A, X, $X^3$, Y and Z have the same meanings as defined above, and Q' represents a hydroxyl, lower alkoxyl, amino, or mono- or di(lower alkyl)amino group.

The compound (N) can be obtained by reacting the compound (L) with the compound (M), and if necessary, in the presence of an acid-neutralizing agent. Any solvent may be used here as long as it does not affect the reaction. For example, the solvents usable in the reaction between the compound (H) and the compound (I) and their mixed solvents can be used. The reaction temperature may generally range from 0° C. to 150° C., with room temperature to about 120° C being preferred. The reaction can be brought to completion generally in 10 minutes to 24 hours. The compound represented by the formula (M) may be used in an amount ranging from an equimolar amount to a large excess amount, relative to the compound (L). When the compound (L) is volatile, the reaction may be conducted in a closed system, for example, by using an autoclave or the like. As the acid-neutralizing agent, those exemplified above can be used.

Process 4

Of the compounds [I], those represented by the formula [I] in which $R^1$ is a hydrogen atom or a lower alkyl group, Y is C—$R^{4'}$, $R^{4'}$ being a lower alkoxyl group, and $R^{2'}$ is one of the groups defined above other than the halogen atoms can also be prepared by the reaction step shown in the following reaction scheme (4):

Reaction Scheme (4)

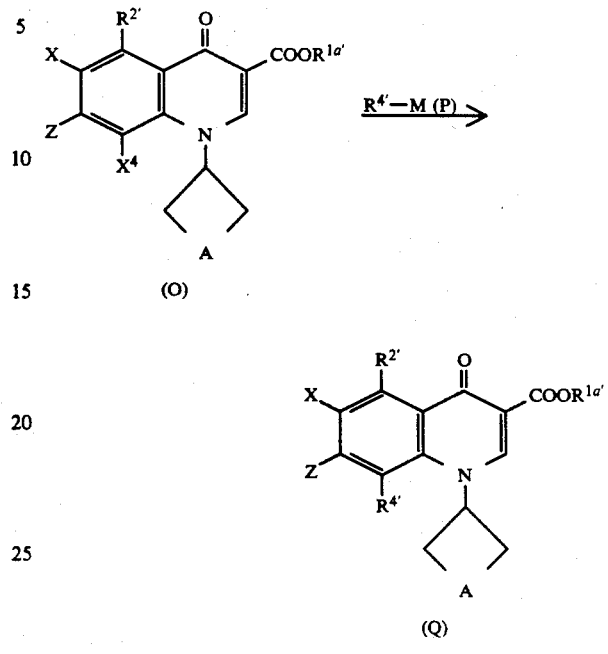

wherein $R^{1a'}$, A, X and Z have the same meanings as defined above, $R^{2'}$ means one of the groups defined above for $R^2$ other than the halogen groups, $X^4$ represents a halogen atom, preferably F or Cl, $R^{4'}$ denotes a lower alkoxyl group, and M is an alkali metal atom.

The compound (Q) can be obtained by reacting the compound (O) with the compound (P). Exemplary preferred solvents usable in this reaction include solvents inert to the reaction and mixed solvents thereof, for example, alcohols corresponding to $R^{4'}$ and in addition, aromatic hydrocarbons such as benzene and toluene, ethers such as tetrahydrofuran and dioxane, dipolar aprotic solvents such as dimethylformamide, dimethylsulfoxide, HMPA and N-methylpyrrolidone, acetonitrile, pyridine and the like. The reaction temperature generally ranges from room temperature to 150° C., preferably from room temperature to about 100° C. The reaction can be brought to completion generally in 10 minutes to 24 hours. The compound (P) can be used in an equimolar amount to a large excess amount, preferably an equimolar amount to a five fold molar amount, relative to the compound (O).

Process 5

Among the compounds represented by the formula [I], those containing a carboxyl-protecting group as $R^1$ can be prepared, for example, by the reaction step shown in the following reaction scheme (5):

Reaction Scheme (5)

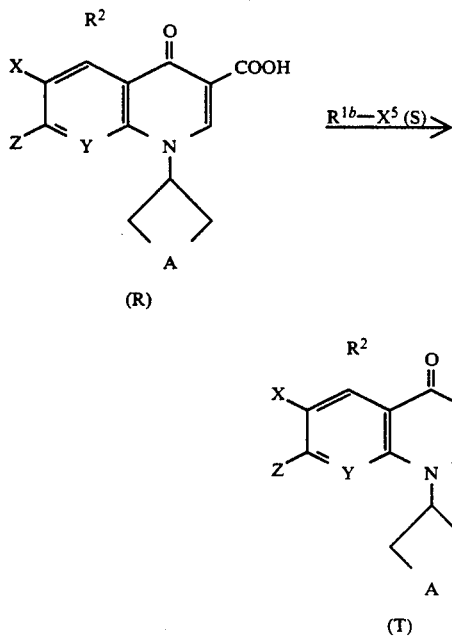

wherein $R^2$, A, X, Y and Z have the same meanings as defined above, $R^{1b}$ means a carboxyl-protecting group, and $X^5$ denotes a halogen atom.

The compound (T) can be obtained by reacting the compound (R) with the compound (S). Exemplary solvents usable in the reaction include inert solvents, for example, aromatic hydrocarbons such as benzene and toluene, halogenated hydrocarbons such as methylene chloride and chloroform, dipolar aprotic solvents such as dimethylformamide and dimethylsulfoxide, and acetonitrile. The reaction temperature generally ranges from room temperature to about 100° C. Preferably, this reaction is carried out in the presence of a basic compounds such as triethylamine, diisopropylethylamine, dicyclohexylamine, DBU, sodium carbonate, potassium carbonate or sodium hydroxide.

Among the compounds represented by the formula [I], those containing a primary or secondary amino group as the heterocyclic group indicated by Z can be converted to the compounds which have a formimidoyl or lower alkylimidoyl group on the amino group by reacting with formimidic acid ester or lower alkanecarboximidic acid ester.

The thus-obtained compounds of the present invention can be isolated and purified by methods known Per se in the art. They are obtained in the form of salts, free carboxylic acids or free amines, depending on the conditions for isolation and purification. However, they can be converted mutually from one of these forms into another one, whereby the compounds of the present invention can be prepared in a desired form.

Action (1) Antibacterial Activities

With respect to certain representative compounds among the compounds [I] of the present invention, their minimum inhibitory concentrations (MIC; μg/ml) were measured in accordance with the standard method established by the Japan Society of Chemotherapy [CHEMOTHERAPY, 29(1), 76-79 (1981)]. The results are summarized in Table 1, in which the compound numbers are as shown in examples.

TABLE 1

| | Minimum inhibitory concentration (μg/ml) | | |
|---|---|---|---|
| Compound No. | E. Coli NIH JC-2 (IFO 12734) | S. aureus 209 P (IFO 12732) | P. aeruginosa (IFO 3445)* |
| 4 | 0.39 | 0.2 | 1.56 |
| 5 | 0.39 | 0.39 | 6.25 |
| 6 | 0.78 | 0.78 | 6.25 |
| 7 | 0.78 | 0.39 | 3.13 |
| 9 | 0.39 | 0.2 | 3.13 |
| 11 | 0.2 | 1.56 | 1.56 |
| 12 | 0.2 | 1.56 | 1.56 |
| 13 | 0.2 | 1.56 | 1.56 |
| 14 | 0.2 | 3.13 | 3.13 |
| 15 | 0.78 | 0.39 | 6.25 |
| 16 | 0.39 | 0.78 | 1.56 |
| 17 | 0.78 | 3.13 | 6.25 |
| 18 | 0.39 | 1.56 | 1.56 |
| 19 | 0.2 | 1.56 | 3.13 |
| 20 | 1.56 | 0.2 | 3.13 |
| 21 | 0.39 | 0.39 | 3.13 |
| 22 | 6.25 | 0.78 | >25 |
| 27 | 0.39 | 0.2 | 3.13 |
| 28 | 0.78 | 0.78 | 6.25 |
| 29 | 0.1 | 0.78 | 0.78 |
| 30 | 0.78 | 0.2 | 3.13 |
| 31 | 0.2 | 0.39 | 0.78 |
| 32 | 0.78 | 0.1 | 3.13 |
| 35 | 0.2 | 1.56 | 3.13 |
| 36 | 0.39 | 3.13 | 3.13 |
| 37 | 0.39 | 1.56 | 1.56 |
| 38 | 3.13 | 0.39 | 12.5 |
| 39 | 0.39 | 1.56 | 6.25 |
| 40 | 0.39 | 0.78 | 6.25 |
| 41 | 0.78 | 12.5 | 6.25 |
| 42 | 0.78 | 1.56 | 3.13 |
| 44 | 0.39 | 1.56 | 1.56 |
| 45 | 0.39 | 1.56 | 3.13 |
| 46 | 0.78 | 0.1 | 3.13 |
| 47 | 0.78 | 0.2 | 6.25 |
| 48 | 0.39 | 1.56 | 3.13 |
| 49 | 0.78 | 1.56 | 3.13 |
| 50 | 0.39 | 0.78 | 1.56 |
| 51 | 0.78 | 1.56 | 3.13 |
| 52 | 0.78 | 0.1 | 3.13 |
| 53 | 0.2 | 0.1 | 3.13 |
| 55 | 0.39 | 0.78 | 0.78 |
| 58 | 0.78 | 0.39 | 6.25 |
| 59 | 0.39 | 0.39 | 3.13 |
| 61 | 0.39 | 3.13 | 1.56 |
| 65 | 0.2 | 1.56 | 0.39 |
| 66 | 0.39 | 3.13 | 3.13 |
| 68 | 0.39 | 3.13 | 0.78 |
| 69 | 0.39 | 3.13 | 1.56 |
| 70 | 1.56 | 0.39 | 6.25 |
| 72 | 0.39 | 0.2 | 3.13 |
| 73 | 0.78 | 0.78 | 6.25 |
| 76 | 0.39 | 0.2 | 1.56 |
| 77 | 1.56 | 1.56 | 12.5 |
| 79 | 1.56 | 0.1 | 25 |
| 81 | 0.78 | 0.78 | 3.13 |
| 82 | 1.56 | 0.78 | 12.5 |
| 85 | 1.56 | 3.13 | 6.25 |
| 86 | 0.39 | 1.56 | 3.13 |
| 88 | 0.78 | 6.25 | 3.13 |
| 89 | 0.78 | 1.56 | 3.13 |
| 90 | 0.2 | 0.2 | 1.56 |
| 91 | 0.2 | 0.78 | 1.56 |
| 92 | 0.1 | 0.39 | 1.56 |
| 93 | 0.78 | 1.56 | 3.13 |
| 94 | 0.2 | 0.78 | 1.56 |
| 95 | 0.2 | 1.56 | 3.13 |
| 96 | 0.1 | 0.39 | 0.78 |
| 97 | 0.39 | 0.78 | 1.56 |
| 101 | 0.1 | 0.2 | 0.78 |
| 102 | 0.1 | 0.39 | 0.78 |
| 103 | 0.1 | 0.2 | 0.39 |
| 107 | 0.78 | 3.13 | 6.25 |
| 108 | 0.78 | 0.78 | 3.13 |
| 109 | 0.39 | 0.78 | 3.13 |

TABLE 1-continued

| Compound No. | Minimum inhibitory concentration (μg/ml) | | |
|---|---|---|---|
| | E. Coli NIH JC-2 (IFO 12734) | S. aureus 209 P (IFO 12732) | P. aeruginosa (IFO 3445)* |
| 110 | 0.78 | 1.56 | 6.25 |

*IFO: Institute for Fermentation Osaka (2) Partition Coefficient

Following the method proposed by Akira Tsuji et al. in Antimicrob. Agents Chemother., 32, 190-194 (1988), 50 mM phosphate buffer (pH 7.4μ=0.15)/n-octanol partition coefficients were measured. The measurement results of representative compounds are shown in Table 2.

TABLE 2

| Compound No. | Partition coefficient |
|---|---|
| 29 | 0.465 ± 0.001 |
| 113 | 0.296 ± 0.003 |

(3) Interaction with Fenbufen and Toxicological Study

These activities were studied by the coadministration test with fenbufen, according to the method of Yamamoto et, al. (Chemotherapy, 36, 300-324, 1988).

Preparation of Materials

Fenbufen and the quinolone compounds were each diluted with a solution of 0.5% methylcellulose.

Test Method

A dose of 200 mg/kg of fenbufen was administered by oral route to groups of 10 mice (female, ICR, 18-23 g) 90 minutes before administration of the quinolone compounds by oral route, at a dose of 500 mg/kg. The number of animals i each group who showed a convulsion activity during two hours following the administration of the compound of this invention was noted. Following the 24 hours number of survival animals was noted. The results are recorded in the following table.

TABLE 3

| Quinolone compound + fenbufen | Induction of convulsion number of positive mice | Mortality number of dead mice |
|---|---|---|
| Compound 29 | 0/10 | 0/10 |
| Compound 117 | 0/10 | 0/10 |
| Enoxacin | 10/10 | 10/10 |

The compounds of this invention benefit from good tolerance to a convulsion caused by drug interactions with antiinflammatory drug and show weak toxicity.

As has been described above, the compounds [I] and their salts according to the present invention are all novel compounds, exhibit extremely high antibacterial activities against gram-negative bacteria and gram-positive bacteria, and have high safety.

When the compounds [I] and their salts according to the present invention are used as antibacterial agents, they can be formulated into preparations along with a pharmaceutically-acceptable carrier for parenteral administration such as injection or rectal administration or for oral administration in the form of a solid or a liquid.

Preparations of this invention for use as injections can take the form of solutions, suspensions or emulsions in pharmaceutically-acceptable germ-free water or non-aqueous liquid. Exemplary suitable non-aqueous carriers, diluents, solvents and vehicles include propylene glycol, polyethylene glycol, vegetable oils such as olive oil, and injectable organic esters such as ethyl oleate. These preparations can contain one or more auxiliary agents, for example, antiseptics, wetting agents, emulsifiers and dispersants. These formulations can be sterilized, for example, by filtering them through a bacterial filter or by mixing, immediately before use, a sterilizing agent in the form of a germ-free solid composition soluble in sterilized water or one of some other media which can be sterilized and injected.

Exemplary solid preparations for oral administration include capsules, tablets, pills, powders, granules, etc. Upon formulation of these solid preparations, the compounds and their salts according to the present invention are generally mixed with at least one inert extender such as sucrose, lactose or starch. One or more materials other than inert extenders, for example, a lubricant such as magnesium stearate can also be incorporated in the preparations upon formulation of the latter in a usual manner. A buffer can also be incorporated in the case of capsules, tablets and pills. Tablets and pills can be applied with an enteric coating.

Illustrative liquid preparations includes pharmaceutically-acceptable emulsions, solutions, suspensions, syrups and elixirs, which contain an inert diluent employed commonly by those skilled in the art, for example, water. In addition to such an inert diluent, the liquid preparations can also be added with one or more auxiliary agents, for example, wetting agents, emulsifiers, suspending agents, sweetening agents, seasoning agents and perfumes.

Preparations for rectal administration are preferably suppositories which may contain an excipient such as cacao butter or suppository wax in addition to a compound or its salt according to the present invention.

The dosage of the compounds [I] and their salts according to the present invention generally ranges from about 0.1 mg/kg to 1,000 mg/kg per day, with about 1-100 mg/kg per day being preferred especially. If desired, this daily dosage can be administered in 2-4 portions.

The present invention will hereinafter be described by the following examples.

EXAMPLE 1

Ethyl 3-(oxetan-3-yl-amino)-2-(2,3,4,5-tetrafluorobenzoyl)acrylate (Compound No. 1)

3,3 g of ethyl 2,3,4,5-tetrafluorobenzoylacetate, 3.1 ml of ethyl orthoformate and 5.3 ml of acetic anhydride were reacted at 130° C. for 4 hours. After volatile components were distilled off under reduced pressure, the residue was dissolved in 60 ml of benzene, followed by the addition of 1 g of 3-aminooxetane at room temperature. After they were reacted at the same temperature for 18 hours, the solvent was distilled off. The residue was subjected to columnchromatography on silica gel (chloroform/ethyl acetate=4/1), whereby 3.54 g of the title compound was obtained as an oil-like yellow substance.

$^1$H-NMR (CDCl$_3$) δ: 1.11(t,J=7Hz,3H), 4.08(q,J=7Hz,2H), 4.7-4.8(m,3H), 4.9-5.05(m,2H), 6.95-7.05(m,1H), 8.09(d,J=13.6Hz,1H).

EXAMPLE 2

Ethyl-1-(oxetan-3-yl)-6,7,8-trifluoro-1,4-dihydro-4-oxoquinoline-3-carboxylate (Compound No. 2)

1.57 g of Compound No. 1 was dissolved in 15 ml of dimethylformamide, followed by the addition of 650 mg of potassium carbonate. The resultant mixture was reacted at 160° C. for 10 minutes. After the solvent was distilled off, the residue was extracted with 50 ml of chloroform. The organic layer was washed with water and then dried over $MgSO_4$. The solvent was thereafter distilled off. The residue was crystallized from hexane-chloroform, whereby 1 g of the title compound was obtained as slightly yellow needle crystals.

Melting point: 146°–147° C.

$^1$H-NMR (CDCl$_3$) δ: 1.4(t,J=7Hz,3H), 4.4(q,J=7Hz,2H), 4.95–5.2(m,4H), 5.7–5.9 (m,1H), 8.1–8.2(m,1H), 8.68(s,1H).

EXAMPLE 3

1-(Oxetan-3-yl)-6,7,8-trifluoro-1,4-dihydro-4-oxoquinoline-3-carboxylic acid (Compound No. 3)

1 g of Compound No. 2 was reacted under reflux for 1 hour in the mixture of 20 ml of ethanol, 4 ml of tetrahydrofuran and 24 ml of a 10% solution of sodium carbonate. After the organic solvents were distilled off, the residue was acidified with 1N-HCl and then extracted with chloroform. The organic layer was washed with water and then dried over $MgSO_4$, and the organic solvent was distilled off. The residue was crystallized from chloroform-hexane, whereby 790 mg of the title compound was obtained as slightly yellow needle crystals.

Melting point: 203°–206° C.

1H-NMR (CDCl$_3$) δ: 4.98–5.26(m,4H), 5.8–6.0(m,1H), 8.2–8.3(m,1H), 8.92(s,1H).

EXAMPLE 4

6,8-Difluoro-1-(oxetan-3-yl)-7-(pyrrolidin-1-yl)-1,4-dihydro-4-oxoquinoline-3-carboxylic acid (Compound No. 4)

100 mg of Compound No. 3 and 71 mg of pyrrolidine were reacted at 80° C. for 1 hour in 1 ml of DMF. After the solvent was distilled off, the residue was extracted with chloroform. The organic layer was washed with 5% acetic acid and water, and then dried over $MgSO_4$. The solvent was distilled off and the residue was crystallized from chloroform-ethanol, whereby 37 mg of the title compound was obtained as colorless needle crystals.

Melting point: 261°–262° C. $^1$H-NMR (CDCl$_3$+DMSO-d$_6$) δ: 1.85–2.0(m,4H), 3.6–3.7(m,4H), 4.85–5.1(m,4H), 5.8–5.9(m,1H), 7.74(d,J=14Hz,1H), 8.66(s,1H).

EXAMPLE 5

Compound Nos. 5–9 and Compound Nos. 11–22, which are shown in Table 4, were obtained in a similar manner to Example 4.

TABLE 4

[Structure: quinolone core with R² at position, F, Y, N (cyclobutyl-O), COOH, with Z substituent]

| Comp'd. No. | R² | Z | Y | Appearance | Melting point (°C.) | [Solvent] ¹H-NMR | Reaction solvent |
|---|---|---|---|---|---|---|---|
| 5 | H | 2,5-dihydropyrrol-1-yl | CF | Yellow solid | 254–250 | [DMSO-d₆]: 4.5–4.6(m, 4H), 4.9–5.1(m, 4H), 5.8–5.9(m, 1H), 5.98(s, 2H), 7.76(dd, J=14Hz, J=2Hz, 1H), 8.64(s, 1H) | DMF |
| 6 | H | morpholin-4-yl | CF | Colorless plate crystals | 266.3 | [CDCl₃]: 3.3–3.4(m, 4H), 3.8–3.9(m, 4H), 5.0–5.2(m, 4H), 5.8–5.9(m, 1H), 7.97(dd, J=11Hz, J=1.5Hz, 1H), 8.77(s, 1H) | DMF |
| 7 | H | thiomorpholin-4-yl | CF | Yellowish white solid | 277.2 | [CDCl₃]: 2.7–2.8(m, 4H), 3.4–3.5(m, 4H), 4.9–5.2(m, 4H), 5.8–5.9(m, 1H), 7.98(dd, J=11.4Hz, J=1.5Hz, 1H), 8.79(s, 1H) | DMF |
| 8 | H | imidazol-1-yl | CF | Colorless solid | 180.5–181.5 | [CDCl₃]: 5.0–5.2(m, 4H), 5.8–6.0(m, 1H), 7.26(s, 1H), 7.33(s, 1H), 7.81(s, 1H), 8.31(dd, J=10Hz, 2Hz, 1H), 8.90(s, 1H) | DMF |
| 9 | H | isoindolin-2-yl | CF | Red solid | 248.5–250.5 | [DMSO-d₆]: 4.9–5.3(m, 8H), 5.8–6.0(m, 1H), 7.2–7.5(m, 4H), 7.85(d, J=10Hz, 1H), 8.7(s, 1H) | DMF |
| 11 | H | 4-methylpiperazin-1-yl | CF | Yellow plate crystals | 221.9 | [CDCl₃]: 2.37(s, 3H), 2.5–2.6(m, 4H), 3.3–3.5(m, 4H), 4.92–5.2(m, 4H), 5.8–5.9(m, 1H), 7.94(dd, J=12Hz, 2Hz, 1H), 8.76(s, 1H) | DMF |

TABLE 4-continued

![Structure: quinolone core with R² at position, F, Z, Y=CF positions, COOH, oxetanyl N-substituent]

| Comp'd. No. | R² | Z | Y | Appearance | Melting point (°C.) | [Solvent] ¹H-NMR | Reaction solvent |
|---|---|---|---|---|---|---|---|
| 12 | H | piperazinyl · CH₃COOH | CF | White solid | 252-254 | [DMSO-d₆]: 1.9(s, 3H), 2.75-2.9(m, 4H), 3.2-3.35(m, 4H), 4.9-5.15(m, 4H), 5.85-5.95(m, 1H), 7.84(d, J=11Hz, 1H), 8.77(s, 1H) | DMSO+DBU |
| 13 | H | 2-methylpiperazinyl | CF | Yellow solid | 228.5-229 | [DMSO-d₆]: 0.97(d, J=5Hz, 3H), 2.6-2.9(m, 3H), 3.0-3.4(m, 4H), 5.8-6.0(m, 1H), 4.9-5.1(m, 4H), 7.83(d, J=12Hz, 1H), 8.74(s, 1H) | DMSO |
| 14 | H | 2,6-dimethylpiperazinyl | CF | Yellow solid | 239.5-240 | [DMSO-d₆]: 0.97(d, J=6.2Hz, 6H), 2.8-2.9(m, 2H), 3.0-3.4(m, 4H), 4.9-5.1(m, 4H), 5.8-6.0(m, 1H), 7.82(dd, J=12Hz, 1.5Hz, 1H), 8.76(s, 1H) | DMSO |
| 15 | H | 4-hydroxypiperidinyl | CF | Yellow needle crystals | 263.5-264 | [CDCl₃+DMSO-d₆]: 1.6-1.8, 1.9-2.05(m, 4H), 3.15-3.3, 3.45-3.6(m, 4H), 3.8-3.9(m, 1H), 4.95-5.2(m, 4H), 5.82-5.95(m, 1H), 7.9(dd, J=12Hz, 2Hz, 1H), 8.79(s, 1H) | DMF |
| 16 | H | 3-hydroxypyrrolidinyl | CF | Yellow powder | 254-256 | [DMSO-d₆]: 1.75-2.0(m, 2H), 3.2-4.0(m, 4H), 4.3-4.4(brs, 1H), 4.85-5.15(m, 4H), 5.75-5.9(m, 1H), 7.73(d, J=13.9Hz, 1H), 8.62(s, 1H) | DMF+DBU |

TABLE 4-continued

[Structure shown at top of table: A quinolone-type structure with R² group, F, Y, Z substituents, C=O, COOH, and N connected to an oxetane ring]

| Comp'd. No. | R² | Z | Y | Appearance | Melting point (°C.) | [Solvent] $^1$H-NMR | Reaction solvent |
|---|---|---|---|---|---|---|---|
| 17 | H | (cyclobutyl with HO and N—) | CF | Yellow solid | 253–254.5 | [DMSO-$d_6$]: 4.05–4.2(brs. 2H), 4.5–4.7(brs, 3H), 4.95–5.15(m, 4H), 5.75–5.9(m, 1H), 7.71(d, J=12.5Hz, 1H), 8.67(s, 1H) | DMF+DBU |
| 18 | H | (pyrrolidine with H₂N and N—) | CF | Brown powder | 160–163 | [DMSO-$d_6$]: 1.8–2.0(m, 2H), 3.3–4.0(m, 5H), 4.85–5.1(m, 4H), 5.75–5.95(m, 1H), 7.76(d, J=12Hz, 1H), 8.65(s, 1H) | DMSO+DBU |
| 19 | H | (pyrrolidine with Me₂N and N—) | CF | Yellow powder | 241–242 | [DMSO-$d_6$+D₂O]: 2.05–2.5(m, 2H), 2.87(s, 6H), 3.75–4.05(m, 4H), 4.1–4.3(m, 1H), 4.9–5.2(m, 4H), 5.85–5.95(m, 1H), 7.73(d, J=13.2Hz, 1H), 8.69(s, 1H) | DMF+DBU |
| 20 | H | (pyrrolidine with H₂N-CH₂ and N—) | CF | Yellow powder | 152–154 | [DMSO-$d_6$]: 1.5–2.1(m, 2H), 2.6–3.0(m, 2H), 3.0–3.6(m, 5H), 4.83–5.07(m, 4H), 5.72–5.95(m, 1H), 7.72(d, J=12Hz, 1H), 8.63(s, 1H) | DMSO+DBU |
| 21 | H | (pyrrolidine with Me₂N (quaternary C) and N—) | CF | Yellow solid | 228.5–229 | [DMSO-$d_6$+MeOH-$d_4$]: 1.65–1.85, 2.1–2.2(m, 2H), 2.5–2.8(m, 2H), 2.86(s, 6H), 3.45–3.95(m, 5H), 4.9–5.15(m, 4H), 5.8–5.95(m, 1H), 7.75(d, J=12Hz, 1H), 8.66(s, 1H) | DMF+DBU |

TABLE 4-continued

[Structure shown: quinolone core with R² at 5-position, F at 6-position, Z at 7-position, Y at 8-position, N-oxetanyl at 1-position, COOH at 3-position, =O at 4-position]

| Comp'd. No. | R² | Z | Y | Appearance | Melting point (°C.) | [Solvent] ¹H-NMR | Reaction solvent |
|---|---|---|---|---|---|---|---|
| 22 | H | [3-(aminomethyl)morpholin-4-yl: H₂N-CH₂- attached to morpholine N-] | CF | White solid | 194–194.5 | [DMSO-d6]: 2.9–3.1(m, 2H), 3.2–3.5(m, 4H), 3.5–4.1(m, 3H), 4.85–5.15(m, 4H), 5.8–6.0(m, 1H), 7.89(d, J=11.7Hz, 1H), 8.76(s, 1H) | DMF + DBU |

EXAMPLE 6

6,8-Difluoro-7-ethoxy-1-(oxetan-3-yl)-1,4-dihydro-4-oxoquinoline-3-carboxylic acid (Compound No. 10)

In Example 3, the mother liquor from which Compound No. 3 had been crystallized was concentrated. Hexane was added to the concentrate to solidify the same, whereby the title compound was obtained as a colorless solid.

Melting point: 175°–176° C.
$^1$H-NMR (CDCl$_3$) δ: 1.46(t,J=7Hz,3H), 4.41(q,J=7Hz,2H), 5.0–5.2(m,4H), 5.8–5.95(m,1H), 8.07(d,J=11Hz,1H), 8.83(s,1H).

EXAMPLE 7

Ethyl 1-(oxetan-3-yl)-5,6,7,8-tetrafluoro-1,4-dihydro-4-oxoquinoline-3-carboxylate (Compound No. 23)

14.1 g of ethyl 2,3,4,5,6-pentafluorobenzoylacetate, 12.5 ml of ethyl orthoformate and 21.2 ml of acetic anhydride were reacted at 130° C. for 3 hours. The solvent was distilled off under reduced pressure and 100 ml of benzene were added to the oily residue. At room temperature, 4.02 g of 3-aminooxetane were added, followed by stirring at the same temperature for 1 day. Benzene was distilled off, and upon addition of hexane, a yellow solid was formed. The solid was collected by filtration and then reacted at 140° C. for 10 minutes in the mixture of 4.73 g of potassium carbonate and 50 ml of dimethylformamide. The solvent was distilled off, followed by extraction with 200 ml of chloroform. After the organic layer was washed with water and dried over MgSO$_4$, the solvent was distilled off. The residue was subjected to columnchromatography on silica gel (chloroform/ethyl acetate=2/1), whereby the title compound was obtained as a yellow oily substance. Upon addition of hexane, the substance was solidified so that 7.94 g of the title compound was obtained as a yellow solid.

Melting point: 110°–113° C.
$^1$H-NMR (CDCl$_3$) δ: 1.4(t,J=7Hz,3H), 4.39(q,J=7Hz,2H), 4.9–5.2(m,4H), 5.7–5.8(m,1H), 8.55(s,1H).

EXAMPLE 8

Ethyl 5-benzylamino-1-(oxetan-3-yl)-6,7,8-trifluoro-1,4-dihydro-4-oxoquinoline-3-carboxylate (Compound No. 24)

3 g of Compound No. 23, 931 mg of benzylamine and 2.35 g potassium carbonate were reacted under reflux for 1 hour in 20 ml of acetonitrile. The solvent was distilled off, followed by extraction with 100 ml of chloroform. After the organic layer was washed with water and dried over MgSO$_4$, the solvent was distilled off. The residue was subjected to columnchromatography on silica gel (chloroform/ethyl acetate=10/1), whereby 2 g of the title compound was obtained as a yellow solid.

Melting point: 127°–128.5° C. $^1$H-NMR (CDCl$_3$) δ: 1.39(t,J=7Hz,3H), 4.39(q,J=7Hz,2H), 4.6–4.75(m,2H), 4.85–5.15(m,4H), 5.6–5.7(m,1H), 7.2–7.5(m,5H), 8.43(s,1H).

EXAMPLE 9

Ethyl 5-amino-1-(oxetan-3-yl)-6,7,8-trifluoro-1,4-dihydro-4-oxoquinoline-3-carboxylate (Compound No. 25)

1.2 g of Compound No. 24 was dissolved in the liquid mixture of 17 ml of tetrahydrofuran, 30 ml of ethanol and 10 ml of acetic acid, to which 500 mg of 10% Pd/C was added. They were reacted under normal pressure and hydrogen gas at room temperature for 16 hours. The reaction mixture was filtered through a Celite (trade mark) pad and the filtrate was concentrated. Ethanol was added to the residue. The resulting solid was collected by filtration, whereby 830 mg of the title compound was obtained as a colorless solid.

Melting point: 111°–112° C.
$^1$H-NMR (CDCl$_3$) δ: 1.4(t,J=7Hz,3H), 4.4(q,J=7Hz,2H), 4.9–5.2(m,4H), 5.6–5.8(m,1H), 6.8–7.2(br,2H), 8.47(s,1H).

EXAMPLE 10

5-Amino-1-(oxetan-3-yl)-6,7,8-trifluoro-1,4-dihydro-4-oxoquinoline-3-carboxylic acid (Compound No. 26)

600 mg of Compound No. 25 was reacted under reflux for 30 minutes in a mixture of 20 ml of ethanol, 20 ml of tetrahydrofuran and 15 ml of 10% sodium carbonate solution. After the organic solvents were distilled off, the pH of the residue was adjusted to 7–6 with acetic acid. The resultant mixture was subjected to centrifugation at 3,000 rpm for 10 minutes and the supernatant was removed by decantation. Using 10 ml of water, 10 ml of ethanol and 10 ml of ether successively, centrifugation and decantation were repeated so tat the precipitate was washed. After ether was removed by decantation, the residue was dried under reduced pressure whereby 280 mg of the title compound was obtained as a yellow solid.

Melting point: 197°–198° C.
$^1$H-NMR (DMSO-d$_6$) δ: 4.8–5.2(m,4H), 5.6–5.8(m,1H), 7.7–8.0(br,2H), 8.65(s,1H).

EXAMPLE 11

5-Amino-6,8-difluoro-1-(oxetan-3-yl)-7-(pyrrolidin-1-yl)-1,4-dihydro-4-oxoquinoline-3-carboxylic acid (Compound No. 27)

60 mg of Compound 26 and 43 mg of pyrrolidine were reacted at 80° C. for 1 hour in 1 ml of dimethylformamide. After the solvent was distilled off, the residue was solidified with 10 ml of ethanol. The solid was collected by filtration. The solid was washed with ethanol and ether, whereby 13 mg of the title compound was obtained as a yellow solid.

Melting point: 250°–253° C.
1H-NMR (DMSO-d$_6$) δ: 1.65–2.0(brs,4H), 3.4–3.8(brs,4H,), 4.7–5.0(m,4H), 5.6–5 8(m,1H), 7.0–7.3(br,2H), 8.45(s,1H).

EXAMPLE 12

Compound Nos. 28–32 and Compound Nos. 148–181, which are shown in Table 5, were obtained in a similar manner to Example 11.

In the subsequent examples, Isomers A and B will indicate those obtained by using starting compounds (raw materials employed to form Z in the formula [I]) isolated by the following procedure.

Compounds obtained using raw materials eluted first by columnchromatography on silica gel (eluent: CHCl$_3$/CH$_3$OH) or raw materials easily crystallized out of ether solution will be designated as Isomers A, while compounds obtained using raw materials eluted later by the chromatography on the silica gel column or raw materials not crystallized easily with ether will be designated as Isomers B.

TABLE 5

Structure: Quinolone core with R² at position, F, Y, Z substituents, N-oxetanyl group, and COOH

| Comp'd. No. | R² | Z | Y | Appearance | Melting point (°C) | [Solvent] ¹H-NMR | Reaction solvent |
|---|---|---|---|---|---|---|---|
| 28 | —NH₂ | thiomorpholine (N-, S) | CF | Yellow solid | 223-225 | [CDCl₃+DMSO-d₆]: 2.6-2.8(brs, 4H), 3.4-3.6 (brs, 4H), 4.85-5.2(m, 4H), 5.6-5.8(m, 1H), 6.5-6.7(brs, 2H), 8.59(s, 1H) | DMF |
| 29 | —NH₂ | N-methylpiperazine | CF | Yellow solid | 235-237 | [CDCl₃+DMSO-d₆]: 2.35(s, 3H), 2.5-2.7(brs, 4H), 3.3-3.45(brs, 4H), 4.8-5.1(m, 4H), 5.6-5.8(m, 1H), 6.6-6.8(brs, 2H), 8.57(s, 1H) | DMF |
| 30 | —NH₂ | isoindoline | CF | Yellow solid | 264-265 | [DMSO-d₆+CDCl₃]: 4.8-5.2(m, 4H), 3.27(brs, 4H), 5.7-5.8(m, 1H), 7.0-7.2(br, 2H), 7.2-7.4(m, 4H), 8.53(s, 1H) | DMF |
| 31 | —NH₂ | 3-aminopyrrolidine | CF | Yellow solid | 200-203 | [DMSO-d₆]: 1.9-2.1(m, 2H), 3.3-4.1(m, 5H), 4.8-5.1(m, 4H), 5.6-5.8(m, 1H), 7.3-7.5(br, 2H), 8.46(s, 1H) | DMF+Et₃N |
| 32 | —NH₂ | 3-(aminomethyl)pyrrolidine | CF | Yellow solid | 128-130 | [DMSO-d₆]: 1.5-2.2(m, 2H), 2.7-3.0(m, 2H), 3.0-3.8(m, 5H), 4.7-5.0(m, 4H), 5.6-5.8(m, 1H), 7.1-7.3(br, 2H), 8.44(s, 1H) | DMF+Et₃N |
| 148 | NH₂ | 3-amino-3-methylpyrrolidine | CF | Pale Yellow powder | 261-263 | [DMSO-d₆]: 1.24(s, 3H), 1.73(brs, 2H), 3.75-3.9(m, 1H), 4.75-5.0(m, 4H), 5.6-5.8(m, 1H), 7.18(brs, 2H), 8.43(s, 1H) | DMSO+Et₃N |

TABLE 5-continued

[Structure: quinolone with R² at position, F, Z substituent, N-oxetanyl, Y, COOH]

| Comp'd. No. | R² | Z | Y | Appearance | Melting point (°C.) | [Solvent] ¹H-NMR | Reaction solvent |
|---|---|---|---|---|---|---|---|
| 149 | NH₂ | [3-amino-3-(hydroxymethyl)-pyrrolidinyl, Me, Isomer A] | CF | Pale Yellow powder | 271-276 | [DMSO-d₆]: 1.03(s, 3H), 3.5-4.1(m, 4H), 4.8-5.1(m, 4H), 5.55-5.8(m, 1H), 7.16(brs, 2H), 8.45(s, 1H) | DMSO+Et₃N |
| 150 | NH₂ | [3-amino-3-(hydroxymethyl)-pyrrolidinyl, Me, Isomer B] | CF | Pale Yellow powder | ≧300 (decomposed) | [DMSO-d₆]: 0.91(s, 3H), 3.6-3.8(m, 2H), 4.7-5.1(m, 4H), 5.6-5.8(m, 1H), 7.15(brs, 2H), 8.45(s, 1H) | DMSO+Et₃N |
| 151 | NH₂ | [3-amino-3,3-dimethyl-pyrrolidinyl] | CF | Pale Yellow powder | ≧210 (colored & decomposed) | [DMSO-d₆]: 1.06(s, 3H), 1.13(s, 3H), 3.58-3.75(m, 2H), 3.9-4.05(m, 1H), 4.75-5.05(m, 4H), 5.6-5.8(m, 1H), 7.23(brs, 2H), 8.46(s, 1H) | DMSO+Et₃N |
| 152 | NH₂ | [3-(1-aminoethyl)pyrrolidinyl, Isomer A] | CF | Yellow powder | 209-213 | [DMSO-d₆]: 1.17(d, J=6.43Hz, 3H), 1.55-1.8(m, 1H), 2.0-2.3(m, 2H), 4.7-5.0(m, 4H), 5.6-5.8(m, 1H), 7.20(brs, 2H), 8.44(s, 1H) | DMSO+Et₃N |
| 153 | NH₂ | [3-(1-aminoethyl)pyrrolidinyl, Isomer B] | CF | Yellow powder | ≧251 (colored & decomposed) | [DMSO-d₆]: 1.25(s, 3H), 1.55-1.8(m, 1H), 1.95-2.1(m, 1H), 2.2-2.4(m, 1H), 4.75-5.05(m, 4H), 5.6-5.8(m, 1H), 7.19(brs, 2H), 8.41(s, 1H) | DMSO+Et₃N |

TABLE 5-continued

| Comp'd. No. | R² | Z | Y | Appearance | Melting point (°C.) | [Solvent] ¹H-NMR | Reaction solvent |
|---|---|---|---|---|---|---|---|
| 154 | NH₂ | H₂N–[pyrrolidine]–Me  Trans(+)-form | CF | Yellow powder | ≧240 (decomposed) | [DMSO-d₆]: 1.07(d, J=5.86Hz, 3H), 2.20-2.4(m, 1H), 3.5-3.8(m, 2H), 3.9-4.1(m, 1H), 4.75-5.05(m, 4H), 5.6-5.8(m, 1H), 7.25(brs, 2H), 8.45(s, 1H) | DMSO+Et₃N |
| 155 | NH₂ | Me–[pyrrolidine], H₂N–  Cis-form | CF | Pale yellow powder | 176-183 | [DMSO-d₆]: 0.97(d, J=6.4Hz, 3H), 2.42(brs, 2H), 2.7-3.0(m, 2H), 3.5-3.9(m, 3H), 4.75-5.02(m, 4H), 5.6-5.75(m, 1H), 7.17(brs, 2H), 8.43(s, 1H) | DMSO+Et₃N |
| 156 | NH₂ | Me–[pyrrolidine], H₂N–  Trans-form | CF | Pale yellow powder | 171-178 | [DMSO-d₆]: 1.06(d, J=4.88Hz, 3H), 1.85-2.1(m, 2H), 3.6-3.9(m, 1H), 4.75-5.05(m, 4H), 5.6-5.87(m, 1H), 7.19(brs, 2H), 8.43(s, 1H) | DMSO+Et₃N |
| 157 | NH₂ | O–[bicyclic]–NH  Trans-form | CF | Pale yellow powder | ≧259 (decomposed) | [DMSO-d₆]: 2.83(brs, 2H), 3.5-3.75(m, 2H), 3.8-3.95(m, 1H), 4.75-5.1(m, 1H), 5.6-5.8(m, 1H), 7.21(brs, 2H), 8.45(s, 1H) | DMSO+Et₃N |
| 158 | NH₂ | H₂N–[pyrrolidine]–F  Isomer B | CF | Yellow powder | ≧224 (decomposed) | [DMSO-d₆]: 2.45-2.75(m, 1H), 3.63(brs, 3H), 3.92(brs, 2H), 4.50(brs, 1H), 4.68(brs, 1H), 4.8-5.1(m, 4H), 5.6-5.8(m, 1H), 7.24(br, 2H), 8.48(s, 1H) | DMSO+Et₃N |

TABLE 5-continued

[Structure: quinolone core with R² at position, F, COOH, N-oxetanyl, Y, Z substituents]

| Comp'd. No. | R² | Z | Y | Appearance | Melting point (°C.) | [Solvent] ¹H-NMR | Reaction solvent |
|---|---|---|---|---|---|---|---|
| 159 | NH₂ | [3-amino-4-fluoromethyl pyrrolidinyl, Isomer A] | CF | Yellow powder | ≧222 (decomposed) | [DMSO-d₆]: 2.5–2.7(m, 1H), 3.75–4.0(m, 1H), 4.52(s, 1H), 4.69(s, 1H), 4.75–5.05(m, 4H), 5.6–5.8(m, 1H), 7.23(brs, 1H), 8.47(s, 1H) | DMSO+Et₃N |
| 160 | H₂N | [4-cyclopropyl piperazinyl] | CF | Yellow powder | 249–251 | [CDCl₃+DMSO-d₆]: 0.25–0.5(m, 4H), 1.52–1.68(m, 1H), 2.66(s, 4H), 3.24(s, 4H), 4.85–5.1(m, 4H), 5.55–5.75(m, 1H), 6.53(brs, 2H), 8.50(s, 1H) | DMSO+Et₃N |
| 161 | H₂N | [4-(2-hydroxyethyl) piperazinyl] | CF | Yellow powder | 257–259 | [DMSO-d₆+D₂O]: 2.46(t, 2H), 2.54(s, 4H), 3.29(s, 4H), 3.52(brs, 2H), 4.40(brs, 1H), 4.80–5.05(m, 4H), 4.65–4.8(m, 1H), 7.27(brs, 2H), 8.53(s, 1H) | DMSO+Et₃N |
| 162 | H₂N | [3-amino-4-methoxymethyl pyrrolidinyl, Isomer B] | CF | Yellow powder | 224–228 | [DMSO-d₆]: 2.25–2.45(m, 1H), 3.28(s, 3H), 3.8–3.95(m, 1H), 4.75–5.0(m, 4H), 4.6–4.75(m, 1H), 7.12(brs, 2H), 8.45(s, 1H) | DMSO+Et₃N |
| 163 | H₂N | [2-fluoromethyl piperazinyl] | CF | Yellow powder | ≧223 (colored & decomposed) | [DMSO-d₆]: 2.9–3.6(m, 7H), 4.37(d, J=5.4Hz, 1H), 4.55(d, J=5.4Hz, 1H), 4.8–5.0(m, 4H), 5.65–5.8(m, 1H), 7.37(brs, 2H), 8.55(s, 1H) | DMSO+Et₃N |

TABLE 5-continued

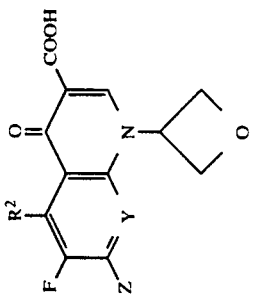

| Comp'd. No. | R² | Z | Y | Appearance | Melting point (°C.) | [Solvent] ¹H-NMR | Reaction solvent |
|---|---|---|---|---|---|---|---|
| 164 | H₂N | piperidine-N-cyclohexyl | CF | Yellow powder | 245–248 | [DMSO-d₆]: 1.05–1.3(m, 6H), 1.65–1.9(m, 4H), 2.2–2.35(m, 1H), 2.59(s, 4H), 3.26(s, 4H), 4.8–5.05(m, 4H), 5.65–5.8(m, 1H), 7.31(brs, 2H), 8.53(s, 1H) | DMSO+Et₃N |
| 165 | H₂N | piperazine-N-cinnamyl | CF | Yellow powder | 193–194 | [CDCl₃]: 2.62(s, 4H), 3.24(d, J=6.35Hz, 2H), 3.39(s, 4H), 4.85–5.1(m, 4H), 5.65–5.85(m, 1H), 6.2–6.4(m, 1H), 6.55–6.7(m, 3H), 7.2–7.5(m, 5H), 8.56(s, 1H) | DMSO+Et₃N |
| 166 | H₂N | piperazine-N-naphthylmethyl | CF | Yellow powder | 178–196 | [CDCl₃]: 2.62(s, 2H), 3.05(s, 3H), 3.39(s, 2H), 3.75(s, 1H), 4.87–5.1(m, 4H), 5.65–5.8(m, 1H), 6.53(brs, 2H), 7.4–7.61(m, 3H), 7.7–7.9(m, 4H), 8.55(s, 1H) | DMSO+Et₃N |
| 167 | H₂N | 3-methylpiperazine | CF | Yellow powder | 225–230 | [DMSO-d₆]: 0.97(d, J=5.37Hz, 3H), 2.77(s, 2H), 3.05–3.2(m, 1H), 3.2–3.45(m, 4H), 4.75–4.9(m, 2H), 4.92–5.00(m, 2H), 5.65–5.81(m, 1H), 7.30(brs, 2H), 8.54(s, 1H) | DMSO+Et₃N |
| 168 | H₂N | 3,5-dimethylpiperazine | CF | Yellow powder | 256–260 | [CDCl₃]: 1.09(d, J=6.34Hz, 6H), 2.75–2.9(m, 2H), 2.95–3.1(m, 2H), 3.2–3.35(m, 2H), 4.89–5.1(m, 4H), 5.65–5.8(m, 1H), 6.54(brs, 2H), 8.57(s, 1H) | DMSO+Et₃N |

TABLE 5-continued

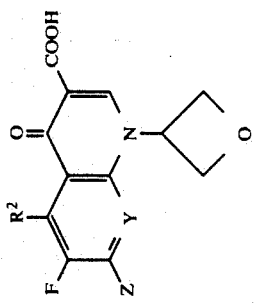

| Comp'd. No. | R² | Z | Y | Appearance | Melting point (°C.) | [Solvent] ¹H-NMR | Reaction solvent |
|---|---|---|---|---|---|---|---|
| 169 | H₂N | ![piperidine-N-tBu] | CF | Yellow powder | 247-250 | [CDCl₃+DMSO-d₆]: 1.12(s, 9H), 2.70(s, 4H), 3.38(s, 4H), 4.9-4.98(m, 2H), 5.0-5.1(m, 2H), 5.67-5.8(m, 1H), 6.65(brs, 2H), 8.57(s, 1H) | DMSO+Et₃N |
| 170 | H₂N | ![piperazine-N-propyl] | CF | Yellow powder | 218-225 | [CDCl₃+DMSO-d₆]: 0.94(t, J=7Hz, 3H), 1.45-1.65(m, 2H), 2.3-2.4(m, 2H), 2.58(s, 4H), 3.39(s, 4H), 4.83-5.15(m, 4H), 5.7-5.9(m, 1H), 6.69(brs, 2H), 8.59(s, 1H) | DMSO+Et₃N |
| 171 | H₂N | ![N-Me piperazine Me] | CF | Yellow powder | 211-216 | [CDCl₃+DMSO-d₆]: 1.10(d, J=6.35Hz, 3H), 2.35(s, 3H), 2.75-2.85(m, 1H), 2.95-3.05(m, 1H), 3.2-3.5(m, 3H), 4.85-5.1(m, 4H), 5.65-5.85(m, 1H), 6.64(brs, 2H), 8.60(s, 1H) | DMSO+Et₃N |
| 172 | H₂N | ![bicyclic amine] | CF | Yellow needle crystals | 244-251 | [CDCl₃]: 1.35-1.5(m, 1H), 1.65-1.9(m, 3H), 2.05-2.25(m, 2H), 2.3-2.45(m, 1H), 2.95-3.2(m, 3H), 3.3-3.55(m, 3H), 4.86-5.15(m, 4H), 5.6-5.8(m, 1H), 6.54(brs, 2H), 8.57(s, 1H) | DMSO+Et₃N |
| 173 | H₂N | ![HN piperazine Me (S)] | CF | Yellow powder | ≧300 | [DMSO-d₆]: 1.23(d, J=6.34Hz, 3H), 3.15-3.5(m, 7H), 4.8-5.0(m, 4H), 5.65-5.8(m, 1H), 7.37(brs, 2H), 8.57(s, 1H) | DMSO+Et₃N |

TABLE 5-continued

| Comp'd. No. | R² | Z | Y | Appearance | Melting point (°C.) | [Solvent] ¹H-NMR | Reaction solvent |
|---|---|---|---|---|---|---|---|
| 174 | H₂N | Et, H₂NCH₂- pyrrolidine (Trans-form) | CF | Yellow powder | 178–185 | [DMSO-d₆]: 0.75–0.97(m, 3H), 1.2–1.4(m, 1H), 1.5–1.7(m, 1H), 1.8–2.0(m, 1H), 2.1–2.25(m, 1H), 4.75–5.05(m, 4H), 2.1–2.25(m, 1H), 4.75–5.05(m, 4H), 5.6–5.8(m, 1H), 7.05–7.35(m, 2H), 8.45(s, 1H) | DMSO+Et₃N |
| 175 | H₂N | Et, H₂NCH₂- pyrrolidine (Cis-form) | CF | Yellow powder | 174–179 | [DMSO-d₆]: 0.8–1.0(m, 3H), 1.25–1.55(m, 2H), 2.05–2.3(m, 1H), 2.9–3.1(m, 1H), 3.5–3.8(m, 2H), 4.7–5.1(m, 4H), 5.55–5.8(m, 1H), 7.15(brs, 2H), 8.44(s, 1H) | DMSO+Et₃N |
| 176 | H₂N | 2-phenylpiperazine | CF | Yellow powder | 224–230 | [DMSO-d₆]: 2.85–3.1(m, 2H), 3.8–3.9(m, 1H), 4.8–5.0(m, 4H), 5.7–5.9(m, 1H), 7.2–7.5(m, 7H), 8.56(s, 1H) | DMSO+Et₃N |
| 177 | H₂N | NH₂, Me, Me-substituted pyrrolidine | CF | Yellow powder | 129–138 | [DMSO-d₆]: 1.07(s, 6H), 1.6–1.75(m, 1H), 1.8–1.95(m, 1H), 2.0–2.2(m, 1H), 4.72–5.0(m, 4H), 5.6–5.75(m, 1H), 7.17(brs, 2H), 8.44(s, 1H) | DMSO+Et₃N |
| 178 | H₂N | Me-N bicyclic, Me (1R, 4R) | CF | Yellow powder | ≧272 (colored & decomposed) | [CDCl₃+DMSO-d₆]: 1.85(d, J=9.27Hz, 1H), 2.00(d, J=9.28Hz, 1H), 2.43(s, 3H), 2.8–3.0(m, 2H), 3.4–3.6(m, 2H), 3.75–3.9(m, 1H), 4.51(brs, 1H), 4.85–5.15(m, 4H), 5.6–5.8(m, 1H), 6.51(brs, 2H), 8.47(s, 1H) | Pyridine DBU |

TABLE 5-continued

[Structure: quinolone core with R² at position, F, Y, Z substituents, N-oxetanyl, COOH]

| Comp'd. No. | R² | Z | Y | Appearance | Melting point (°C.) | [Solvent] ¹H-NMR | Reaction solvent |
|---|---|---|---|---|---|---|---|
| 179 | $H_2N$ | [bicyclic diamine (1R, 4R)] | CF | Yellow solid | ≧300 | [DMSO-$d_6$]: 1.4–1.8(m, 2H), 3.00(brs, 2H), 3.85(brs, 1H), 4.54(s, 1H), 4.65–5.0(m, 4H), 5.65–5.8(m, 1H), 7.20(brs, 2H), 8.42(s, 1H) | Pyridine DBU |
| 180 | $H_2N$ | [3-methylpiperazine (R)] | CF | Yellow powder | ≧260 (decomposed) | [DMSO-$d_6$]: 1.25(d, J=5.86Hz, 3H), 4.8–5.05(m, 4H), 5.65–5.85(m, 1H), 7.3–7.45(m, 2H), 8.57(s, 1H) | DMSO+$Et_3N$ |
| 181 | $H_2N$ | [pyrrolidine with CH(Me)NHMe, Isomer A] | CF | Yellow powder | 185–191 | [DMSO-$d_6$]: 1.18(d, J=6.3Hz, 3H), 1.5–1.85(m, 1H), 2.05–2.25(m, 1H), 2.3–2.45(m, 1H), 2.5(s, 3H), 3.0–3.2(m, 1H), 3.4–3.85(m, 4H), 4.75–5.1(m, 4H), 5.6–5.85(m, 1H), 7.18(brs, 2H), 8.44(s, 1H) | DMSO+$Et_3N$ |

EXAMPLE 13

Ethyl 6,7-difluoro-1-(oxetan-3-yl)-1,4-dihydro-4-oxoquinoline-3-carboxylate (Compound No. 33)

4 g of ethyl 2,4,5-trifluorobenzoylacetate, 4.06 ml of ethyl orthoformate and 6.9 ml of acetic anhydride were reacted at 130° C. for 1.5 hours. Volatile components were distilled off under reduced pressure, followed by the addition of 50 ml of benzene. At room temperature, 1.3 g of 3-aminooxetane were added and stirred at the same temperature for 15 hours. The solvent was distilled off. Hexane was added and a solid thus formed was collected by filtration (about 4.2 g).

4.2 g of the solid and 1.76 g of potassium carbonate were reacted at 110° C. for 15 minutes in 20 ml of dimethylformamide. The solvent was distilled off and the residue was extracted with 50 ml of chloroform. The chloroform extract was washed with water and then dried over MgSO$_4$. The solvent was thereafter distilled off. Hexane was added and the resulting solid was collected by filtration, whereby 2.13 g of the title compound was obtained as a yellow solid.

Melting point: 177°–178° C.
1H-NMR (CDCl$_3$) δ: 1.42(t,J=7Hz,3H), 4.41(q,J=7Hz,2H), 5.0–5.2(m,4H), 5.4–5.6(m,1H), 6.9–7.0(m,1H), 8.2–8.4(m,1H), 8.59(s,1H).

EXAMPLE 14

6,7-Difluoro-1-(oxetan-3-yl)-1,4-dihydro-4-oxoquinoline-3-carboxylic acid (Compound No. 34)

2.13 g of Compound No. 33 was dissolved under heat in the mixture of 30 ml of THF and 30 ml of ethanol, to which 10 ml of water and 15 ml of 10% aq. sodium carbonate solution were added. They were reacted under reflux for 1.5 hours. After the organic solvents were distilled off, the residue was acidified with 1N-HCl and the resultant solid was collected by filtration. The solid was successively washed with 3 ml portions of water, ethanol and ether, whereby 1.58 g of the title compound was obtained as a pale red solid.

Melting point: 255°–256° C.
1H-NMR (DMSO-d$_6$) δ: 4.9–5.2(m,4H), 5.8–5.9(m,1H), 7.8–8.0(m,1H), 8.2–8.4(m,1H), 8.89(s,1H).

EXAMPLE 15

6-Fluoro-7-(4-methylpiperazin-1-yl)-1-(oxetan-3-yl)-1,4-dihydro-4-oxoquinoline-3-carboxylic acid (Compound No. 35)

80 mg of Compound No. 34 and 100 mg of 1-methylpiperazine were reacted at 80° C. for 1 hour in 1 ml of dimethylformamide. After the solvent was distilled off, 3 ml of ethanol was added to the residue so that the latter was solidified. In addition, 10 ml of hexane were added and the solid was collected by filtration. The solid was successively washed with 5 ml of ethanol, 1 ml of chloroform and 5 ml of hexane, whereby 68 mg of the title compound was obtained as a yellow solid.

Melting point: 178°–180° C.
1H-NMR (DMSO-d$_6$) δ: 2.27(s,3H), 2.4–2.6(s,4H), 3.3–3.4(s,4H), 4.9–5.2(m,4H), 5.9–6.1(m,1H), 6.84(d,J=7.3Hz,1H), 7.94(d,J=13.6Hz,1H), 8.71(s,1H).

EXAMPLE 16

Compound Nos. 36–42 and Compound Nos. 182–188, which are shown in Table 6, were obtained in a similar manner to Example 15.

TABLE 6

![structure: R² and F on benzene ring, fused pyridone with COOH, N-oxetanyl, Y and Z substituents]

| Comp'd. No. | R² | Z | Y | Appearance | Melting point (°C.) | [Solvent] ¹H-NMR | Reaction solvent |
|---|---|---|---|---|---|---|---|
| 36 | H | piperazin-1-yl (HN-) | CH | Yellow solid | 129–130 | [DMSO-d₆]: 2.8–2.9(brs, 4H), 3.2–3.3(brs, 4H), 4.9–5.2(m, 4H), 5.9–6.0(m, 1H), 6.81(d, J=7Hz, 1H), 7.92(d, J=13.7Hz, 1H), 8.71(s, 1H) | DMSO |
| 37 | H | 3-aminopyrrolidin-1-yl (H₂N-) | CH | Pale yellow solid | 249–251 | [DMSO-d₆]: 1.7–2.1(m, 2H), 3.1–3.8(m, 5H), 4.9–5.2(m, 4H), 5.8–6.0(m, 1H), 6.3(d, J=7.3Hz, 1H), 7.82(d, J=14.7Hz, 1H), 8.60(s, 1H) | DMSO+Et₃N |
| 38 | H | 3-(aminomethyl)pyrrolidin-1-yl (H₂N-) | CH | Pale yellow solid | 148–149 | [DMSO-d₆]: 1.7–2.2(m, 2H), 2.6–2.8(m, 1H), 2.8–3.0(m, 2H), 3.2–3.9(m, 4H), 4.9–5.2(m, 4H), 5.8–6.0(m, 1H), 6.31(d, J=6Hz, 1H), 7.85(d, J=14.1Hz, 1H), 8.61(s, 1H) | DMSO+Et₃N |
| 39 | H | 3-(dimethylamino)pyrrolidin-1-yl (Me₂N-) | CH | Colorless solid | 246–247 | [DMSO-d₆]: 1.7–1.9(m, 2H), 2.23(s, 6H), 2.7–2.9(m, 1H), 3.2–3.8(m, 2H), 4.9–5.2(m, 4H), 5.8–6.0(m, 1H), 6.34(d, J=7Hz, 1H), 7.82(d, J=14.2Hz, 1H), 8.61(s, 1H) | DMF+Et₃N |
| 40 | H | 3-((dimethylamino)methyl)pyrrolidin-1-yl (Me₂N-) | CH | Yellow solid | 209–210 | [DMSO-d₆]: 1.7–2.3(m, 2H), 2.7–3.0(m, 7H), 3.1–3.3(m, 2H), 3.4–3.9(m, 4H), 4.9–5.2(m, 4H), 5.7–5.9(m, 1H), 7.15(d, J=7Hz, 1H), 7.84(d, J=13.6Hz, 1H), 8.59(s, 1H) | DMF+Et₃N |

TABLE 6-continued

[Structure: quinolone core with R² at 5-position, F at 6-position, Z at 7-position, Y at 8-position (shown as Y/N), N-oxetanyl at 1-position, COOH at 3-position, =O at 4-position]

| Comp'd. No. | R² | Z | Y | Appearance | Melting point (°C) | [Solvent] ¹H-NMR | Reaction solvent |
|---|---|---|---|---|---|---|---|
| 41 | H | H₂N-cyclopropyl-N— | CH | Pale yellow solid | ≧270 (decomposed) | [DMSO-d₆]: 3.7-4.0(m, 3H), 4.25-4.4(m, 2H), 4.8-5.2(m, 4H), 5.8-5.9(m, 1H), 6.18(d, J=7.3Hz, 1H), 7.81(d, J=12.7Hz, 1H), 8.62(s, 1H) | DMSO+Et₃N |
| 42 | H | HO-pyrrolidinyl-N— | CH | Pale yellow solid | 293-295 | [DMSO-d₆]: 1.8-2.1(m, 2H), 3.4-3.8(m, 4H), 4.3-4.5(m, 1H), 4.9-5.2(m, 4H), 5.8-6.0(m, 1H), 6.32(d, J=7.3Hz, 1H), 7.83(d, J=14.1Hz, 1H), 8.60(s, 1H) | DMF+Et₃N |
| 182 | H | Me, H₂N-pyrrolidinyl-N— | CH | Colorless powder | 281-284 | [DMSO-d₆]: 1.28(s, 3H), 1.8-1.9(m, 2H), 3.5-3.9(m, 2H), 4.9-5.15(m, 4H), 5.8-5.95(m, 1H), 6.28(d, J=7.33Hz, 1H), 7.81(d, J=14.65Hz, 1H), 8.60(s, 1H) | DMSO+Et₃N |
| 183 | H | Me, NH₂-pyrrolidinyl-N— Isomer A | CH | Yellow powder | ≧233 (colored & decomposed) | [DMSO-d₆]: 1.27(d, J=5.86Hz, 3H), 1.7-1.9(m, 1H), 2.1-2.3(m, 1H), 2.4-2.6(m, 1H), 4.95(brs, 2H), 5.11(brs, 2H), 5.87(brs, 1H), 6.32(brs, 1H), 7.81(d, J=14.16Hz, 1H), 8.59(s, 1H) | DMSO+Et₃N |
| 184 | H | Me, NH₂-pyrrolidinyl-N— Isomer B | CH | Yellow powder | ≧248 (colored & decomposed) | [DMSO-d₆]: 1.25(d, J=5.86Hz, 3H), 1.65-1.9(m, 1H), 2.05-2.2(m, 1H), 2.3-2.5(m, 1H), 3.5-3.8(m, 4H), 4.87-5.07(m, 2H), 5.1-5.28(m, 2H), 5.75-5.9(m, 1H), 6.27(d, J=6.8Hz, 1H), 7.85(d, J=14.2Hz, 1H), 8.59(s, 1H) | DMSO+Et₃N |

TABLE 6-continued

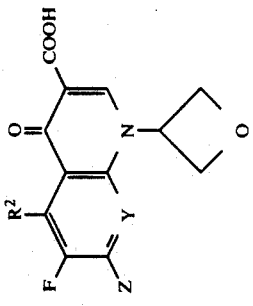

| Comp'd. No. | R² | Z | Y | Appearance | Melting point (°C.) | [Solvent] ¹H-NMR | Reaction solvent |
|---|---|---|---|---|---|---|---|
| 185 | H | 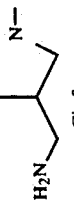 Me, H₂N Cis-form N— | CH | Pale yellow powder | 178-183 | [DMSO-d₆]: 1.00(brs, 3H), 2.7-3.1(m, 2H), 4.98(brs, 2H), 5.13(brs, 2H), 5.7-5.95(m, 1H), 6.30(s, 1H), 7.83(d, J=14.16Hz, 1H), 8.59(s, 1H) | DMSO+Et₃N |
| 186 | H | HN (1R, 4R) N— | CH | Pale yellow solid | 281-286 | [DMSO-d₆]: 1.65-1.9(m, 2H), 2.85-3.05(m, 2H), 3.5-3.85 (m, 3H), 4.69(s, 1H), 4.9-5.18(m, 4H), 5.8-5.95(m, 1H), 6.37(d, J=7.8Hz, 1H), 7.85(d, J=14.16Hz, 1H), 8.61(s, 1H) | Pyridine DBU |
| 187 | H | Me, H₂N Trans-form N— | CH | Pale yellow powder | 204-208 | [DMSO-d₆]: 1.12(s, 3H), 2.16(brs, 2H), 2.75-2.95(m, 1H), 3.05-3.15(m, 1H), 3.75-3.96(m, 2H), 4.97(brs, 2H), 5.15(brs, 2H), 5.75-5.95(m, 1H), 6.28(brs, 1H), 7.85(d, J=14.16Hz, 1H), 8.59(s, 1H) | DMSO+Et₃N |
| 188 | H | 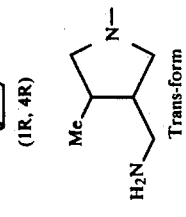 | CH | Pale yellow powder | 185-190 | [CDCl₃]: 1.4-2.0(m, 4H), 2.1-2.3(m, 2H), 2.4-2.6(m, 1H), 2.65-2.8(m, 1H), 3.0-3.25(m, 3H), 3.6-3.83(m, 2H), 5.05-5.3(m, 4H), 5.55-5.7(m, 1H), 6.52(d, J=6.84Hz, 1H), 8.05(d, J=13.2Hz, 1H), 8.67(s, 1H) | DMSO+Et₃N |

EXAMPLE 17

6-Fluoro-7-(imidazol-1-yl)-8-methoxy-1-(oxetan-3-yl)-1,4-dihydro-4-oxoquinoline-3-carboxylic acid (Compound No. 43)

158 mg of Compound No. 8 and 290 mg of sodium methoxide (28% methanol solution) were reacted under reflux for 15 hours in 5 ml of methanol. After the solvent was distilled off, 3 ml of water was added. The pH of the resultant mixture was adjusted to about 6-7 with 20% acetic acid and the resultant solid was collected by filtration. The solid was washed successively with small amounts of water and ethanol, whereby 70 mg of the title compound was obtained as pale yellow powder.

Melting point: 152°-154° C.

$^1$H-NMR (DMSO-d$_6$) δ: 3.34(s,3H), 4.8-5.1(m,4H), 5.9-6.1(m,1H), 7.23(brs,1H), 7.55(brs,1H), 8.03(brs,1H), 8.09(d,J=10Hz,1H), 8.84(s,1H).

EXAMPLE 18

6,8-Difluoro-7-(3-methylaminopyrrolidin-1-yl)-1-(oxetan-3-yl)-1,4-dihydro-4-oxoquinoline-3-carboxylic acid (Compound No. 44)

80 mg of Compound No. 3, 69 mg of 3-methylaminopyrrolidine dihydrochloride and 162 mg of triethylamine were reacted at 80° C. for 1 hour in 0.5 ml of DMSO. 2 ml of ethanol and 10 ml of hexane were added, and the resulting solid was collected by filtration. The solid was washed successively with 3 ml of ethanol and 3 ml of hexane, whereby 68 mg of the title compound was obtained as a pale yellow solid.

Melting point: 252°-255° C.

$^1$H-NMR (DMSO-d$_6$) δ: 1.7-2.1(m,2H), 2.29(s,3H), 3.1-3.9(m,5H), 4.85-5.05(m,4H), 5.8-5.9(m,1H), 7.74(d,J=14Hz,1H), 8.63(s,1H).

EXAMPLE 19

Compound Nos. 45-59, Compound No. 85, Compound No. 112 and Compound Nos. 118-147, which are shown in Table 7, were obtained in a similar manner to Example 18.

TABLE 7

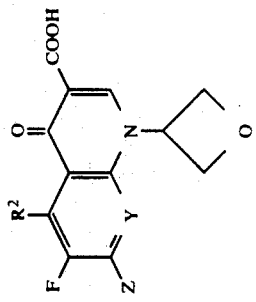

| Comp'd. No. | R² | Z | Y | Appearance | Melting point (°C.) | [Solvent] ¹H-NMR | Reaction solvent |
|---|---|---|---|---|---|---|---|
| 45 | H | Me-N(H)-pyrrolidinyl | CF | Pale yellow solid | 235–237 | [DMSO-d₆]: 1.03(t, J=7Hz, 3H), 1.7–2.1(m, 2H), 2.45–2.7(m, 2H), 3.2–3.9(m, 5H), 4.85–5.1(m, 4H), 5.75–5.9(m, 1H), 7.74(d, J=15.1Hz, 1H), 8.64(s, 1H) | DMSO+Et₃N |
| 46 | H | MeN(H)CH₂-pyrrolidinyl | CF | Pale yellow solid | 266–271 | [DMSO-d₆]: 1.6–2.2(m, 2H), 2.44(s, 3H), 2.3–3.8(m, 7H), 4.9–5.1(m, 4H), 5.8–5.9(m, 1H), 7.75(d, J=15Hz, 1H), 8.65(s, 1H) | DMSO+Et₃N |
| 47 | H | Me-CH₂-N(H)-pyrrolidinyl | CF | Pale yellow solid | 251–253.5 | [DMSO-d₆]: 1.22(t, J=7Hz, 3H), 1.7–2.2(m, 2H), 2.4–2.7 (m, 3H), 2.9–3.1(m, 2H), 3.2–3.9(m, 4H), 4.9–5.1 (m, 4H), 5.8–6.0(m, 1H), 7.8(d, J=15Hz, 1H), 8.65(s, 1H) | DMSO+Et₃N |
| 48 | H | H₂N-azetidinyl | CF | Pale yellow solid | 233–237 | [DMSO-d₆]: 3.7–3.85(m, 1H), 3.9–4.1, 4.45–4.6 (m, 4H), 4.9–5.05(m, 4H), 5.7–5.95(m, 1H), 7.73(d, J=12.2Hz, 1H), 8.63(s, 1H) | DMSO+Et₃N |
| 49 | NH₂ | H₂N-azetidinyl | CF | Pale yellow solid | 178–180 | [DMSO-d₆]: 3.85–4.0(m, 1H), 4.05–4.2, 4.45–4.55(m, 4H), 4.75–5.0(m, 4H), 5.6–5.75(m, 1H), 7.2(brs, 2H), 8.44(s, 1H) | DMSO+Et₃N |

TABLE 7-continued

| Comp'd. No. | R² | Z | Y | Appearance | Melting point (°C.) | [Solvent] ¹H-NMR | Reaction solvent |
|---|---|---|---|---|---|---|---|
| 50 | NH₂ | MeN-H-(pyrrolidin-3-yl) | CF | Yellow powder | 214–216 | [DMSO-d₆]: 1.65–2.0(m, 2H), 2.29(s, 3H), 3.1–3.8(m, 5H), 4.75–5.0(m, 4H), 5.6–5.75(m, 1H), 7.15(brs, 2H), 8.43(s, 1H) | DMSO+Et₃N |
| 51 | NH₂ | Me-N-H-(pyrrolidin-3-yl) | CF | Yellow powder | 205–209 | [DMSO-d₆]: 1.06(t, J=7Hz, 3H), 1.7–2.1(m, 2H), 2.62–2.66(m, 2H), 3.1–3.9(m, 5H), 4.75–5.0(m, 4H), 5.6–5.75(m, 1H), 7.2(brs, 2H), 8.44(s, 1H) | DMSO+Et₃N |
| 52 | NH₂ | MeN-H-CH₂-(pyrrolidin-3-yl) | CF | Yellow solid | 198–201 | [DMSO-d₆]: 1.55–2.15(m, 2H), 2.34(s, 3H), 2.55–2.7(m, 1H), 2.55–2.7(m, 2H), 2.7–3.8(m, 6H), 4.75–5.0(m, 4H), 5.6–5.8(m, 1H), 7.15(brs, 2H), 8.44(s, 1H) | DMSO+Et₃N |
| 53 | NH₂ | Me-N-H-CH₂-(pyrrolidin-3-yl) | CF | Yellow solid | 175–178 | [DMSO-d₆]: 1.03(t, J=6.9Hz, 3H), 1.55–2.1(m, 2H), 2.25–2.4(m, 1H), 2.55–2.7(m, 2H), 3.0–3.8(m, 6H), 4.8–5.0(m, 4H), 5.6–5.8(m, 1H), 7.2(brs, 2H), 8.44(s, 1H) | DMSO+Et₃N |
| 54 | NH₂ | HO-(azetidin-1-yl) | CF | Yellow solid | 250–253 | [DMSO-d₆]: 4.0–4.1, 4.45–4.65(m, 5H), 4.75–5.0(m, 4H), 5.6–5.8(m, 1H), 7.2(brs, 2H), 8.43(s, 1H) | DMSO+Et₃N |

TABLE 7-continued

[Structure: quinolone core with R² at one position, F, Y (=CF), Z substituent, N-cyclobutyl group, and COOH]

| Comp'd. No. | R² | Z | Y | Appearance | Melting point (°C.) | [Solvent] ¹H-NMR | Reaction solvent |
|---|---|---|---|---|---|---|---|
| 55 | NH₂ | piperazin-1-yl (HN‾N–) | CF | Yellow solid | 217–220 | [DMSO-d₆]: 2.80(brs, 4H), 3.21(brs, 4H) 4.75–5.1(m, 4H), 5.65–5.8(m, 1H), 7.28(brs, 2H), 8.54(s, 1H) | DMSO |
| 56 | NH₂ | 3-(dimethylamino)pyrrolidin-1-yl | CF | Yellow solid | 217–220 | [DMSO-d₆]: 2.05–2.4(m, 2H), 2.75(s, 6H), 3.6–4.0(m, 4H), 4.75–5.05(m, 4H), 5.6–5.8(m, 1H), 7.26(brs, 2H), 8.47(s, 1H) | DMSO+Et₃N |
| 57 | NH₂ | 3-[(dimethylamino)methyl]pyrrolidin-1-yl | CF | Yellow solid | 224–227 | [DMSO-d₆]: 1.6–2.2(m, 2H), 2.5–2.6(m, 1H), 2.74 (s, 6H), 3.1–3.2(m, 2H), 3.4–3.9(m, 4H), 4.75–5.0 (m, 4H), 5.6–5.8(m, 1H), 7.2(brs, 2H), 8.43(s, 1H) | DMSO+Et₃N |
| 58 | NH₂ | morpholin-4-yl | CF | Yellow solid | 248–250 | [DMSO-d₆+D₂O]: 3.29(s, 4H), 3.71(s, 4H), 4.8–5.1(m, 4H), 5.65–5.8(m, 1H), 7.3(brs, 2H), 8.54(s, 1H) | DMF |
| 59 | NH₂ | 3-hydroxypyrrolidin-1-yl | CF | Yellow solid | 260–262 | [DMSO-d₆]: 1.7–2.0(m, 2H), 3.3–3.9(m, 4H), 4.25–4.4(brs, 1H), 4.75–5.1(m, 5H), 5.6–5.8(m, 1H), 7.16(brs, 2H), 8.43(s, 1H) | DMF+Et₃N |

TABLE 7-continued

| Comp'd. No. | R² | Z | Y | Appearance | Melting point (°C.) | [Solvent] ¹H-NMR | Reaction solvent |
|---|---|---|---|---|---|---|---|
| 85 | H | H₂N—⟨pyrrolidine⟩—OMe, Trans form | CF | Colorless solid | 219–222 | [DMSO-d₆+D₂O]: 3.30(s, 3H), 3.3–4.2(m, 6H) 4.8–5.1(m, 4H), 5.7–5.9(m, 1H), 7.75(d, J=13.7Hz, 1H), 8.63(s, 1H) | DMSO+Et₃N |
| 112 | H | O₂N—⟨nitropyridyl-tetrahydro⟩—N— | CF | Pale yellow solid | ≧210 (decomposed) | [DMSO-d₆]: 2.7–3.9(m, 4H), 4.3–4.8 (m, 2H), 4.8–5.2(m, 4H), 5.7–6.0(m, 1H), 7.92(d, J=12Hz, 1H), 8.47(s, 1H), 8.76(s, 1H), 9.23(s, 1H) | DMF+Et₃N |
| 118 | H | Me, H₂N—⟨pyrrolidine⟩—N— | CF | Colorless powder | 262–265 | [DMSO-d₆]: 1.25(s, 3H), 1.75(brs, 2H), 3.3–4.0 (m, 4H), 4.85–5.1(m, 4H), 5.75–5.9(m, 1H), 7.73(d, J=13.7Hz, 1H), 8.62(s, 1H) | DMSO+Et₃N |
| 119 | H | H₂N—⟨pyrrolidine⟩—Me, Me —N— | CF | Slightly yellow powder | colored from 160° C. decomposed at 183° C. and above | [DMSO-d₆]: 1.03(s, 3H), 1.10(s, 3H), 2.3–2.7(m, 1H), 3.5–4.0(m, 4H), 4.85–5.15(m, 4H), 5.75–6.0 (m, 1H), 7.76(d, J=13.7Hz, 1H), 8.66(s, 1H) | DMSO+Et₃N |
| 120 | H | Me—CH(NH₂)—⟨pyrrolidine⟩—N—, Isomer A | CF | Yellow powder | 215–218 | [DMSO-d₆]: 1.21(d, J=6.3Hz, 3H), 1.6–1.8(m, 1H), 2.1–2.4(m, 2H), 3.1–3.9(m, 4H), 4.8–5.1(m, 4H), 5.7–5.9(m, 1H), 7.75(d, J=14.1Hz, 1H), 8.64(s, 1H) | DMSO+Et₃N |

TABLE 7-continued

| Comp'd. No. | R² | Z | Y | Appearance | Melting point (°C) | [Solvent] ¹H-NMR | Reaction solvent |
|---|---|---|---|---|---|---|---|
| 121 | H | (pyrrolidine with Me, NH₂; Isomer B) | CF | Yellow powder | ≧264° C. (colored and decomposed) | [DMSO-d₆]: 1.23(d, J=6.4Hz, 3H), 1.5-1.7(m, 1H), 1.9-2.4(m, 2H), 3.1-3.8(m, 4H), 4.8-5.05(m, 4H), 5.7-5.9(m, 1H), 7.75(d, J=14.1Hz, 1H), 8.62(s, 1H) | DMSO+Et₃N |
| 122 | H | (pyrrolidine with Me, H₂N; Cis-form) | CF | Pale yellow powder | 179-184 | [DMSO-d₆]: 0.95(d, J=6.8Hz, 3H), 2.3-2.5(m, 2H), 2.6-2.9(m, 2H), 3.3-3.9(m, 4H), 4.9-5.1(m, 4H), 5.8-6.0(m, 1H), 7.8(d, J=14Hz, 1H), 8.65(s, 1H) | DMSO+Et₃N |
| 123 | H | (pyrrolidine with Me, H₂N; Trans-form) | CF | Pale yellow powder | 125-133 | [DMSO-d₆]: 1.05(d, J=4.9Hz, 3H), 1.9-2.1(m, 2H), 2.6-3.0(m, 2H), 3.0-3.9(m, 4H), 4.9-5.1(m, 4H), 5.8-6.0(m, 1H), 7.8(d, J=14Hz, 1H), 8.66(s, 1H) | DMSO+Et₃N |
| 124 | H | (pyrrolidine with Me, H₂N; Trans(−)-form) | CF | Slightly yellow powder | 193-204 | [DMSO-d₆]: 1.06(d, J=4.4Hz, 3H), 2.3-2.5(m, 1H), 3.1-4.1(m, 5H), 4.85-5.1(m, 4H), 5.75-5.9(m, 1H), 7.75(d, J=13.7Hz, 1H), 8.65(s, 1H) | DMSO+Et₃H |
| 125 | H | (fused bicyclic O,N-H; *Trans-form) | CF | Slightly yellow powder | 231-238 | [DMSO-d₆]: 2.7-3.0(m, 2H), 3.15-3.8(m, 7H), 4.8-4.9(m, 1H), 4.85-5.1(m, 4H), 5.8-5.95 (m, 1H), 7.76(d, J=13.1Hz, 1H), 8.66(s, 1H) | DMSO+Et₃N |

TABLE 7-continued

| Comp'd. No. | R² | Z | Y | Appearance | Melting point (°C.) | [Solvent] ¹H-NMR | Reaction solvent |
|---|---|---|---|---|---|---|---|
| 126 | H | H₂N— ⌬ —CH₂F  Isomer B | CF | Slightly yellow powder | 200–216 | [DMSO-d₆]: 2.2–2.5(m, 1H), 3.1–4.05(m, 5H), 4.4–4.8(m, 2H), 4.85–5.2(m, 4H), 5.75–5.95 (m, 1H), 7.76(d, J=14.2Hz, 1H), 8.67(s, 1H) | DMSO+Et₃N |
| 127 | H | H₂N— ⌬ —CH₂F  Isomer A | CF | Slightly yellow powder | 211–218 | [DMSO-d₆]: 2.2–2.4(m, 1H), 3.2–4.0(m, 5H), 4.45–4.8(m, 2H), 4.85–5.1(m, 4H), 5.75–5.95 (m, 1H), 7.74(d, J=12.7Hz, 1H), 8.66(s, 1H) | DMSO+Et₃N |
| 128 | H | H₂N— ⌬ —CH₂OMe  Isomer B | CF | Slightly yellow powder | 225–229 | [DMSO-d₆]: 2.3–2.45(m, 1H), 3.28(s, 3H), 3.2–4.0 (m, 7H) 4.8–5.1(m, 4H), 5.75–5.9(m, 1H), 7.71(d, J=12.7Hz, 1H), 8.64(s, 1H) | DMSO+Et₃N |
| 129 | H | HN⌬N—CH₂F | CF | Slightly yellow powder | 188–191 | [DMSO-d₆]: 2.9–3.6(m, 7H), 4.5–4.75(m, 2H), 4.9–5.2(m, 4H), 5.85–6.0(m, 1H), 7.90(d, J=11.2Hz, 1H), 8.78(s, 1H) | DMSO+Et₃N |
| 130 | H | ⌬N—C₆H₁₁ | CF | Slightly yellow powder | 228–233 | [CDCl₃]: 1.0–1.4(m, 6H), 1.8–2.0(m, 4H), 2.2–2.4 (m, 1H), 2.73(s, 4H), 3.41(s, 4H), 4.95–5.25(m, 4H) 5.8–6.0(m, 1H), 7.93(d, J=11.7Hz, 1H), 8.78(s, 1H) | DMSO+Et₃N |

TABLE 7-continued

[Structure shown: quinolone core with R² , F, Y, Z substituents, N-cyclobutyl, COOH]

| Comp'd. No. | R² | Z | Y | Appearance | Melting point (°C.) | [Solvent] ¹H-NMR | Reaction solvent |
|---|---|---|---|---|---|---|---|
| 131 | H | [piperazinyl-CH₂-CH=CH-phenyl] | CF | Slightly yellow powder | 190–201 | [CDCl₃]: 2.66(s, 4H), 3.24(d, J=6.8Hz, 1H), 3.42 (s, 4H), 5.0–5.2(m, 4H), 5.75–6.0(m, 1H), 6.2–6.4 (m, 1H), 6.57(d, J=16.1Hz, 1H), 7.2–7.5(m, 5H), 7.94(d, J=11.7Hz, 1H), 8.75(s, 1H) | DMSO+Et₃N |
| 132 | H | [piperazinyl-CH₂-naphthyl] | CF | Slightly yellow powder | 143–153 | [CDCl₃]: 2.4–2.6(m, 4H), 3.08(s, 2H), 3.42 (brs, 3H), 3.77(s, 1H), 4.9–5.2(m, 4H), 5.8–6.0 (m, 1H), 7.5–8.0(m, 7H), 8.75(s, 1H) | DMSO+Et₃N |
| 133 | H | [t-Bu-piperazinyl] | CF | Slightly yellow powder | 153–159 | [CDCl₃+DMSO-d₆]: 1.44(s, 9H), 2.6(brs, 4H), 3.2 (brs, 4H), 4.95–5.2(m, 4H), 5.8–6.0(m, 1H), 7.96(d, J=11.3Hz, 1H), 8.82(s, 1H) | DMSO+Et₃N |
| 134 | H | [N-propyl-piperazinyl] | CF | Slightly yellow powder | 199–201 | [CDCl₃]: 0.95(t, J=7.3Hz, 3H), 1.5–1.7(m, 2H), 2.40(t, J=7.8Hz, 2H), 2.61(brs, 4H), 3.42 (brs, 4H), 4.9–5.2(m, 4H), 5.8–5.95(m, 1H), 7.95(dd, J=12Hz, J=1.6Hz, 1H), 8.76(s, 1H) | DMSO+Et₃N |
| 135 | H | [2-Me,4-Me-piperazinyl] | CF | Slightly yellow powder | 165–168 | [CDCl₃]: 1.14(d, J=5.9Hz, 3H), 2.39(s, 3H), 2.3–2.5 (m, 2H), 2.85–3.0(m, 1H), 3.1–3.6(m, 4H), 4.9–5.2 (m, 4H), 5.8–5.95(m, 1H), 7.95(d, J=9.8Hz, 1H), 8.77(s, 1H) | DMSO+Et₃N |

TABLE 7-continued

| Comp'd. No. | R² | Z | Y | Appearance | Melting point (°C.) | [Solvent] ¹H-NMR | Reaction solvent |
|---|---|---|---|---|---|---|---|
| 136 | H | ![structure: bicyclic diamine] | CF | Slightly yellow powder | 182–193 | [CDCl₃]: 1.35–1.6(m, 1H), 1.7–2.0(m, 3H), 2.1–2.3 (m, 1H), 2.35–2.5(m, 1H), 2.95–3.2(m, 3H), 3.3–3.6 (m, 3H), 4.9–5.2(m, 4H), 5.8–6.0(m, 1H), 7.94(d, J = 11.7Hz, 1H), 8.76(s, 1H) | DMSO + Et₃N |
| 137 | H | ![structure: piperazine with Me(S)] | CF | Slightly yellow powder | 245–253 | [DMSO-d₆]: 1.26(d, J = 5.9Hz, 3H), 3.0–3.6(m, 7H), 4.85–5.1(m, 4H), 5.8–5.95(m, 1H), 7.90 (d, J = 11.2Hz, 1H), 8.79(s, 1H) | DMSO + Et₃N |
| 138 | H | ![structure: phenyl piperazine] | CF | Slightly yellow powder | 128–133 | [DMSO-d₆]: 2.8–3.5(m, 6H), 3.85–3.95(m, 1H), 4.85–5.1(m, 4H), 5.85–6.0(m, 1H), 7.25–7.5 (m, 5H), 7.87(d, J = 12.2Hz, 1H), 8.78(s, 1H) | DMSO + Et₃N |
| 139 | H | ![structure: pyrrolidine with C(Me)₂NH₂] | CF | Slightly yellow powder | 238–243 | [DMSO-d₆]: 1.07(s, 6H), 1.5–2.0(m, 2H), 2.05–2.2 (m, 1H), 3.1–3.9(m, 4H), 4.85–5.1(m, 4H), 5.75–5.95(m, 1H) | DMSO + Et₃N |

TABLE 7-continued

| Comp'd. No. | R² | Z | Y | Appearance | Melting point (°C.) | [Solvent] ¹H-NMR | Reaction solvent |
|---|---|---|---|---|---|---|---|
| 140 | H | (piperazinyl with Me(R)) | CF | Slightly yellow powder | Colored from 230° C. decomposed at 240° C. and above | [DMSO-d₆]: 1.24(d, J=6.3Hz, 3H), 3.0–3.6(m, 7H), 4.85–5.1(m, 4H), 5.8–6.0(m, 1H), 7.91(d, J=13.7Hz, 1H), 8.79(s, 1H), 7.73(d, J=14.2Hz, 1H), 8.63(s, 1H) | DMSO+Et₃N |
| 141 | H | (N-cyclopropyl piperazinyl) | CF | Colorless powder | 211–215 | [CDCl₃]: 1.35–1.55(m, 4H), 1.6–1.8(m, 1H), 2.76(brs, 4H), 3.35(brs, 4H), 4.95–5.2(m, 4H), 5.8–5.95(m, 1H), 7.93(d, J=10.3Hz, 1H), 8.75(s, 1H) | DMSO+Et₃N |
| 142 | H | (N-hydroxyethyl piperazinyl) | CF | Colorless powder | 216–219 | [CDCl₃+DMSO-d₆]: 2.5–2.75(m, 6H), 3.41(brs, 4H), 3.6–3.8(m, 2H), 4.95–5.25(m, 4H), 5.8–6.0(m, 1H), 7.93(d, J=11.7Hz, 1H), 8.79(s, 1H) | DMSO+Et₃N |
| 143 | H | (aminomethyl-methyl-hydroxymethyl pyrrolidinyl) Isomer A | CF | Slightly yellow powder | 165–171 | [DMSO-d₆]: 1.10(s, 3H), 3.2–4.1(m, 7H), 4.8–5.1(m, 4H), 5.7–6.0(m, 1H), 7.76(d, J=13.7Hz, 1H), 8.66(s, 1H) | DMSO+Et₃N |
| 144 | H | (aminomethyl-methyl-hydroxymethyl pyrrolidinyl) Isomer B | CF | Slightly yellow powder | 150–154 | [DMSO-d₆]: 1.02(s, 3H), 2.8–4.0(m, 7H), 4.8–5.1(m, 4H), 5.75–6.0(m, 1H), 7.75(d, J=13.6Hz, 1H), 8.67(s, 1H) | DMSO+Et₃N |

TABLE 7-continued

Structure: quinolone core with R², F, Y, Z substituents, N-oxetanyl group, COOH at 3-position.

| Comp'd. No. | R² | Z | Y | Appearance | Melting point (°C.) | [Solvent] 1H-NMR | Reaction solvent |
|---|---|---|---|---|---|---|---|
| 145 | H | MeN-bicyclic (1R, 4R) | CF | Pale yellow powder | ≧260° C. (colored and decomposed) | [CDCl$_3$+DMSO-d$_6$]: 1.87(d, J=9.77Hz, 1H), 2.03 (d, J=9.76Hz, 1H), 2.44(s, 3H), 2.8–3.0(m, 2H), 3.47 (brs, 1H), 3.5–3.6(m, 1H), 3.8–3.95(m, 1H), 4.56(s, 1H), 4.9–5.15(m, 4H), 5.65–5.85(m, 1H), 7.85(d, J=12.2Hz, 1H), 8.66(s, 1H) | pyridine DBU |
| 146 | H | HN-bicyclic (1R, 4R) | CF | Pale yellow powder | ≧275° C. (decomposed) | [DMSO-d$_6$]: 1.6–2.0(m, 2H), 3.05(brs, 2H), 4.61 (brs, 1H), 4.7–5.1(m, 4H), 5.6–5.9(m, 1H), 7.75(d, J=13Hz, 1H), 8.61(s, 1H) | Pyridine DBU |
| 147 | H | Me-CH(NHMe)-pyrrolidinyl Isomer A | CF | Pale yellow powder | 215–220 | [DMSO-d$_6$]: 1.00(d, J=6.4Hz, 3H), 1.6–1.75(m, 1H), 2.0–2.25(m, 2H), 2.30(s, 1H), 4.9–5.1(m, 4H), 5.8–5.95(m, 1H), 7.73(d, J=14.6Hz, 1H), 8.64(s, 1H) | DMSO+Et$_3$N Pyridine DBU |

EXAMPLE 20

Ethyl 7-chloro-6-fluoro-1-(oxetan-3-yl)-1,4-dihydro-4-oxo-1,8-naphthylidine-3-carboxylate (Compound No. 60)

8.4 g of ethyl 2,6-dichloro-5-fluoronicotinoylacetate, 7.5 ml of ethyl orthoformate and 12.7 ml of acetic anhydride were reacted at 130° C. for 2 hours. Volatile components were distilled off under reduced pressure, followed by the addition of 30 ml of dichloromethane and 2.56 g of 3-aminooxetane. They were reacted at room temperature for 1.5 hours. The solvent was distilled off. 100 ml of hexane was added to the resulting solid, followed by the collection of the solid by filtration. 10.5 g of the solid thus collected was dissolved in 140 ml of tetrahydrofuran, to which 1.21 g of sodium hydride (content: 60%) was added by portions under ice cooling over 30 minutes. They were reacted further at room temperature for 30 minutes and then under reflux for additional 1 hour. Tetrahydrofuran was distilled off, followed by the extraction with 100 ml of chloroform. The chloroform layer was washed successively with 30 ml of 1N-HCl and 50 ml of water, and then dried over MgSO$_4$. Chloroform was distilled off. To the residue were added 50 ml of hexane and 50 ml of ether, so that the residue was solidified. The solid thus obtained was ground and collected by filtration. 5.15 g of the title compound were obtained as pale yellow powder.

Melting point: 163°-166° C.

$^1$H-NMR (CDCl$_3$) δ: 1.43(t,J=7Hz,3H), 4.40(q,J=7Hz,2H,), 4.97(t,J=6.8Hz,2H), 5.20(t-J=7.4Hz,2H), 5.95-6.15(m,1H), 8.47(d,J=8.3Hz,1H,), 8.81(s,1H).

EXAMPLE 21

6-Fluoro-7-(4-methylpiperazin-1-yl)-1-(oxetan-3-yl)-1,4-dihydro-4-oxo-1,8-naphthylidine-3-carboxylic acid (Compound No. 61)

200 mg of Compound No. 60, 64 mg of N-methylpiperazine and 65 mg of triethylamine were reacted under reflux for 1.5 hours in 5 ml of chloroform. Volatile components were distilled off and to the residue were added 5 ml of ethanol, 3 ml of 10% aq. sodium carbonate solution and 2 ml of water. They were reacted under reflux for 1.5 hours. The solvent was distilled off. 20% acetic acid was added to the residue to adjust the pH to about 6. The resulting solid was collected by filtration and successively washed with ethanol and ether, whereby 13 mg of the title compound was obtained as a colorless solid.

Melting point: 235°-236.5° C.

$^1$H-NMR (CDCl$_3$) δ: 2.36(s,3H), 2.5-2.6(m,4H), 3.8-3.9(m,4H), 4.95-5.2(m,4H), 5.8-6.0(m,1H), 8.1(d,J=13.2Hz,1H), 8.76(s,1H).

EXAMPLE 22

Compound Nos. 62-73, Compound No. 88 and Compound Nos. 189-196, which are shown in Table 8, were obtained in a similar manner to Example 21.

TABLE 8

[Structure: quinolone core with R² at one position, F, Z, Y=N, and N-oxetanyl (4-membered ring with O) substituent, bearing COOH and ketone]

| Comp'd. No. | R² | Z | Y | Appearance | Melting point (°C.) | [Solvent] ¹H-NMR | Reaction solvent |
|---|---|---|---|---|---|---|---|
| 62 | H | HN⟨piperazinyl⟩N— | N | Colorless solid | ≥280 C. (decomposed) | [DMSO-d₆]: 2.83(brs, 4H), 3.73(brs, 4H), 4.9–5.1(m, 4H), 5.75–5.95(m, 1H), 8.08 (d, J=13.2Hz, 1H), 8.68(s, 1H) | CHCl₃ |
| 63 | H | O⟨morpholinyl⟩N— | N | Colorless solid | 249.5–251 | [CDCl₃]: 3.86(S, 8H), 5.0–5.2(m, 4H), 5.85–6.0(m, 1H), 8.14(d, J=13.2Hz, 1H), 8.78(s, 1H) | CHCl₃ |
| 64 | H | S⟨thiomorpholinyl⟩N— | N | Colorless solid | 265–266.5 | [CDCl₃]: 2.7–2.9(m, 4H), 4.05–4.2(m, 4H), 5.0–5.2(m, 4H), 5.8–5.95(m, 1H), 8.14 (d, J=13.2Hz, 1H), 8.77(s, 1H) | CHCl₃ |
| 65 | H | H₂N⟨3-aminopyrrolidinyl⟩N— | N | Pale yellow solid | ≥300 (decomposed) | [DMSO-d₆]: 1.6–2.1(m, 2H), 3.1–4.0(m, 5H), 4.9–5.1(m, 4H), 5.7–5.85(m, 1H), 7.96(d, J=13.2Hz, 1H), 8.56(s, 1H) | CHCl₃ |
| 66 | H | Me₂N⟨3-dimethylaminopyrrolidinyl⟩N— | N | Pale yellow solid | 225–228 | [DMSO-d₆]: 1.7–2.3(m, 2H), 2.22(s, 6H), 2.7–2.9 (m, 1H), 3.2–4.05(m, 4H), 4.9–5.15(m, 4H), 5.7–5.9 (m, 1H), 7.99(d, J=13.7Hz, 1H), 8.60(s, 1H) | CHCl₃ + Et₃N |

TABLE 8-continued

[Structure: quinolone core with R² at 5-position, F at 6-position, Z at 7-position, Y at 8-position, cyclobutyl on N-1, COOH at 3-position, =O at 4-position]

| Comp'd. No. | R² | Z | Y | Appearance | Melting point (°C.) | [Solvent] ¹H-NMR | Reaction solvent |
|---|---|---|---|---|---|---|---|
| 67 | H | 3-hydroxypyrrolidin-1-yl (HO on pyrrolidine) | N | Pale yellow solid | 259–261 | [DMSO-d₆]: 1.8–2.1(m, 2H), 3.55–4.0(m, 4H), 4.35–4.5(m, 1H), 4.9–5.1(m, 4H), 5.7–5.9(m, 1H), 7.98(d, J=13.2Hz, 1H), 8.59(s, 1H) | CHCl₃ + Et₃N |
| 68 | H | 3-(methylamino)pyrrolidin-1-yl (MeNH) | N | Pale yellow solid | ≅280° C. (decomposed) | [DMSO-d₆]: 1.8–2.1(m, 2H), 2.30(s, 3H), 3.1–4.0 (m, 5H), 4.9–5.1(m, 4H), 5.7–5.85(m, 1H), 7.98(d, J=13.2Hz, 1H), 8.58(s, 1H) | CHCl₃ + Et₃N |
| 69 | H | 3-(ethylamino)pyrrolidin-1-yl (MeCH₂NH) | N | Pale yellow solid | 210–213 | [DMSO-d₆]: 1.05(t, J=7Hz, 3H), 1.8–2.2(m, 2H), 2.5–2.7(m, 2H), 3.2–3.9(m, 5H), 4.9–5.1(m, 4H), 5.7–5.9(m, 1H), 7.97(d, J=13.2Hz, 1H), 8.57(s, 1H) | CHCl₃ + Et₃N |
| 70 | H | 3-((methylamino)methyl)pyrrolidin-1-yl (MeNHCH₂) | N | Colorless solid | 232–236 | [DMSO-d₆]: 1.6–2.2(m, 2H), 2.30(s, 3H), 2.3–2.6 (m, 1H), 3.2–4.0(m, 6H), 4.9–5.1(m, 4H), 5.7–5.9(m, 1H), 7.97(d, J=13.2Hz, 1H), 8.58(s, 1H) | CHCl₃ + Et₃N |
| 71 | H | 3-(aminomethyl)pyrrolidin-1-yl (H₂NCH₂) | N | Pale yellow solid | 216–218 | [DMSO-d₆]: 1.6–2.2(m, 2H), 2.5–2.7(m, 1H), 3.0–4.0 (m, 6H), 4.9–5.1(m, 4H), 5.7–5.9(m, 1H), 7.95(d, J=13.2Hz, 1H), 8.56(s, 1H) | CHCl₃ + Et₃N |

TABLE 8-continued

| Comp'd. No. | R² | Z | Y | Appearance | Melting point (°C.) | [Solvent] ¹H-NMR | Reaction solvent |
|---|---|---|---|---|---|---|---|
| 72 | H | (pyrrolidinyl N-) | N | Pale yellow solid | 286–289 | [CDCl₃]: 1.9–2.1(brs, 4H), 3.6–4.0(m, 4H), 5.0–5.2(m, 4H), 5.75–5.9(m, 1H), 7.98(d, J=12.7Hz, 1H), 8.64(s, 1H) | CHCl₃ |
| 73 | H | (thiazolidinyl N-) | N | Pale yellow solid | 264–267 | [CDCl₃ + DMSO-d₆]: 3.21(t, J=6.3Hz, 2H), 4.05–4.2 (m, 2H), 4.88(s, 2H), 5.0–5.2(m, 4H), 5.8–6.0 (m, 1H), 8.10(d, J=12.2Hz, 1H), 8.77(s, 1H) | CHCl₃ |
| 88 | H | H₂N, MeO (Trans-form) pyrrolidinyl | N | Colorless powder | 155.5–156.5 | [DMSO-d₆ + D₂O]: 3.32(s, 3H), 3.3–4.1(m, 6H), 4.85–5.2(m, 4H), 5.7–5.9(m, 1H), 7.98(d, J=12.2Hz, 1H), 8.59(s, 1H) | CHCl₃ + Et₃N |
| 189 | H | H₂N, Me Trans(−)-form pyrrolidinyl | ≡N— | Pale yellow powder | colored from 230° C., decomposed at 280° C. and above | [DMSO-d₆]: 1.03(s, 3H), 2.15–2.35(m, 1H), 4.85–5.2(m, 4H), 5.7–5.9(m, 1H), 7.93(d, J=13.2Hz, 1H), 8.55(s, 1H) | CHCl₃ + Et₃N |
| 190 | H | H₂N, Me pyrrolidinyl | ≡N— | Pale yellow powder | 266–269 | [DMSO-d₆]: 1.29(s, 3H), 1.7–1.9(m, 2H), 4.85–5.1(m, 4H), 5.7–5.9(m, 1H), 7.93(d, J=13.2Hz, 1H), 8.55(s, 1H) | CHCl₃ + Et₃N |

TABLE 8-continued

[Structure: quinolone core with R² at 5-position, F at 6-position, Z at 7-position, Y at 8-position (N or CH), cyclobutyl N-substituent, 3-COOH, 4-oxo]

| Comp'd. No. | R² | Z | Y | Appearance | Melting point (°C.) | [Solvent] ¹H-NMR | Reaction solvent |
|---|---|---|---|---|---|---|---|
| 191 | H | pyrrolidin-2-yl with Me and NH₂ (Isomer A) | =N— | Pale yellow powder | 234–237 | [DMSO-d₆]: 1.05(d, 3H), 2.05–2.2(m, 2H), 2.75–2.9(m, 1H), 4.95–5.05(m, 4H), 5.75–5.85(m, 1H), 8.0(d, J=13Hz, 1H), 8.32(s, 1H) | CHCl₃ + Et₃N |
| 192 | H | 2-methyl-2,5-diazabicyclo (1R, 4R) | =N— | Colorless powder | ≧270° C. (colored and decomposed) | [DMSO-d₆]: 1.8–2.05(m, 2H), 2.35(s, 3H), 2.6–2.7(m, 1H), 2.85–2.95(m, 1H), 3.6–3.9 (m, 2H), 4.85–5.15(m, 5H), 5.6–5.75(m, 1H), 8.02(d, J=12.7Hz, 1H), 8.60(s, 1H) | CHCl₃ + DBU |
| 193 | H | 2-methyl-2,5-diazabicyclo (1R, 4R) | CH | Pale yellow powder | 256–260 | [DMSO-d₆]: 2.0–2.25(m, 2H), 2.65(s, 3H), 3.4–3.8(m, 4H), 4.03(brs, 1H), 4.82(s, 1H), 4.9–5.2(m, 4H), 5.8–6.0(m, 1H), 6.46(d, J=6.35Hz, 1H), 7.89(d, J=13.57Hz, 1H), 8.65(s, 1H) | Pyridine DBU |
| 194 | H | 2,5-diazabicyclo (1R, 4R) | =N— | Pale yellow powder | ≧300 | [DMSO-d₆]: 1.7–1.9(m, 2H), 2.9–3.1(m, 2H), 3.77(brs, 1H), 4.9–5.2(m, 5H), 5.7–5.9(m, 1H), 7.98(d, J=12.2Hz, 1H), 8.59(s, 1H) | CHCl₃ + DBU |

TABLE 8-continued

[Structure shown: quinolone core with R² at C5, F at C6, Z at C7, Y at C8 position, N-oxetanyl at N1, COOH at C3, =O at C4]

| Comp'd. No. | R² | Z | Y | Appearance | Melting point (°C.) | [Solvent] ¹H-NMR | Reaction solvent |
|---|---|---|---|---|---|---|---|
| 195 | H | [3-(1-aminoethyl)pyrrolidin-1-yl, Isomer B] | =N— | Pale yellow powder | 218–223 | [DMSO-d$_6$]: 1.23(brs, 3H), 1.6–1.85(m, 1H), 1.96–2.2 (m, 1H), 2.2–2.42(m, 1H), 3.0–3.25(m, 1H), 4.85–5.2 (m, 4H), 5.7–5.9(m, 1H), 7.95(d, J=12.7Hz, 1H), 8.58(s, 1H) | CHCl$_3$ + Et$_3$N |
| 196 | H | [(1S,4S)-2,5-diazabicyclo[2.2.1]heptan-2-yl] ArOH | H | Yellow powder | ≧275 (decomposed) | [DMSO-d$_6$]: 1.65–1.95(m, 2H), 1.88(s, 3H), 2.8–3.1 (m, 2H), 3.5–3.9(m, 2H), 4.70(s, 1H), 4.8–5.15(m, 4H), 5.8–5.95(m, 1H), 6.36(d, J=6.83Hz, 1H), 7.83(d, J=14.2Hz, 1H), 8.60(s, 1H) | CHCl$_3$ + Et$_3$N |

EXAMPLE 23

Ethyl 6,7-difluoro-8-methoxy-1-(oxetan-3-yl)-1,4-dihydro-4-oxoquinoline-3-carboxylate (Compound No. 74)

10.8 g of ethyl 2-chloro-4,5-difluoro-3-methoxybenzoylacetate, 9.4 ml of ethyl orthoformate and 15.7 ml of acetic anhydride were reacted at 130° C. for 3 hours. After volatile components were distilled off, 40 ml of benzene and 29.2 g of 3-aminooxetane were added at room temperature. They were reacted at the same temperature for 50 minutes. After the solvent was distilled off, 30 ml of ether was added to the residue so that the latter was solidified. The resultant solid was ground and then collected by filtration, whereby 10.4 g of a white solid was obtained. The solid was dissolved in 500 ml of tetrahydrofuran, to which 1.28 g of sodium hydride (content: 60%) was added. They were stirred for 3 days under gently refluxed. The solvent was distilled off, and 300 ml of water was added to the residue, followed by extraction with chloroform (200 ml×3 times). The organic layers were dried over $MgSO_4$ and distilled off. To the residue was added 100 ml of ether so that the latter was solidified. The solid thus formed was ground and then collected by filtration, whereby 3.8 g of the title compound was obtained as a pale yellow solid.

Melting point: 195°–198° C.
$^1$H-NMR (CDCl$_3$) δ: 1.41(t,J=7.05Hz,3H), 4.03(d,J=1.95Hz,3H), 4.41(q, J=7.05Hz,2H), 4.85–5.2(m,4H), 5.8–6.0(m,1H), 8.0–8.1(m,1H), 8.67(s,1H).

EXAMPLE 24

6,7-Difluoro-8-methoxy-1-(oxetan-3-yl)-1,4-dihydro-4-oxoquinoline-3-carboxylic acid (Compound No. 75)

2.7 g of Compound No. 74 was reacted under reflux for 20 minutes in a liquid mixture which consisted of 110 ml of tetrahydrofuran and 40 ml of 2N sodium hydroxide solution. Tetrahydrofuran was distilled off and the remaining aqueous solution was rendered acidic (about pH 6) with 20% acetic acid. The resultant solid was collected by filtration and then successively washed with 10 ml of water, 20 ml of ethanol and 30 ml of ether, whereby 1.97 g of the title compound was obtained as a colorless solid.

Melting point: 178°–179° C.
$^1$H-NMR (CDCl$_3$) δ: 4.10(d,J=2.48Hz,3H), 4.85(m,4H), 5.9–6.1(m,1H), 8.05–8.15(m,1H), 8.87(m,1H).

EXAMPLE 25

7-(3-Aminopyrrolidin-1-yl)-6-fluoro-8-methoxy-1-(oxetan-3-yl)-1,4-dihydro-4-oxoquinoline-3-carboxylic acid (Compound No. 76)

100 mg of Compound No. 75 and 86 g of 3-aminopyrrolidine were reacted at 80° C. for 30 minutes in 1 ml of DMSO. After the reaction mixture was cooled, 2 ml of ethanol and 20 ml of ether were added and the resultant mixture was stirred. The supernatant was removed by decantation. The residue was solidified with 5 ml of ethanol, followed by grinding. The solid was collected by filtration and washed with 5ml of ethanol, whereby 42 mg of the title compound was obtained as a colorless solid.

Melting point: 199°–202° C.
$^1$H-NMR (DMSO-d$_6$+D$_2$O) δ: 1.6–2.1(m,2H), 3.46(s,3H), 3.2–3.9(m,5H), 4.7–5.1(m,4H), 5.8–6.0(m,1H), 7.65(d,J=14.6Hz,1H), 8.58(s,1H).

EXAMPLE 26

Compound Nos. 77–84, 86, 87, 89–96, 101–103, 106 and 107, which are shown in Table 9, were obtained in a similar manner to Example 25.

TABLE 9

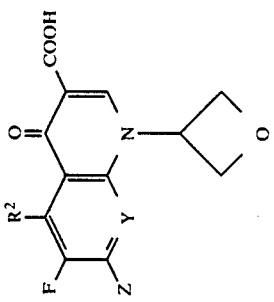

| Comp'd. No. | R² | Z | Y | Appearance | Melting point (°C.) | [Solvent] ¹H-NMR | Reaction solvent |
|---|---|---|---|---|---|---|---|
| 77 | H | Me₂N-pyrrolidin-3-yl | C—OMe | Pale yellow solid | 212.5-214 | [CDCl₃]: 1.7-2.3(m, 2H), 2.33(s, 6H), 2.6-2.8 (m, 1H), 3.50(s, 3H), 3.5-4.0(m, 4H), 4.7-5.3(m, 4H), 5.8-6.0(m, 1H), 7.85(d, J=13.7Hz, 1H), 8.63(s, 1H) | DMF + Et₃N |
| 78 | H | pyrrolidin-1-yl | C—OMe | Yellow solid | 237-239 | [CDCl₃]: 1.99(brs, 4H), 3.48(s, 3H), 3.61(brs, 4H), 4.85-5.2(m, 4H), 5.8-5.95(m, 1H), 7.83(d, J=13.7Hz, 1H), 8.60(s, 1H) | DMF |
| 79 | H | MeNHCH₂-pyrrolidin-3-yl | C—OMe | Yellow solid | 147-149 | [DMSO-d₆]: 1.22(t, J=6.3Hz, 3H), 1.7-2.2(m, 2H), 2.4-2.7 (m, 1H), 2.8-3.1(m, 4H), 3.48(s, 3H), 3.3-3.8(m, 4H), 4.7-5.1(m, 4H), 5.8-6.0(m, 1H), 7.71(d, J=13.7Hz, 1H), 8.61(s, 1H) | DMSO + Et₃N |
| 80 | H | 3-hydroxy-pyrrolidin-1-yl | C—OMe | Yellow solid | 225-227 | [DMSO-d₆]: 1.7-2.1(m, 2H), 3.45(s, 3H), 3.2-4.0(m, 4H), 4.2-4.45(m, 1H), 4.6-5.2(m, 4H), 5.8-6.0(m, 1H), 7.67 (d, J=13.7Hz, 1H), 8.59(s, 1H) | DMF + Et₃N |
| 81 | H | piperazin-1-yl | C—OMe | Pale yellow solid | 157-159 | [DMSO-d₆]: 2.82(brs, 4H), 3.22(brs, 4H), 3.67(s, 3H), 4.65-5.1(m, 4H), 5.8-6.0(m, 1H), 7.76(d, J=12.7Hz, 1H), 8.66(s, 1H) | DMSO |

TABLE 9-continued

| Comp'd. No. | R² | Z | Y | Appearance | Melting point (°C.) | [Solvent] ¹H-NMR | Reaction solvent |
|---|---|---|---|---|---|---|---|
| 82 | H | (MeHN-CH₂-pyrrolidine) | C—OMe | Colorless solid | 182-184 | [DMSO-d₆]: 1.03(t, J=7.6Hz, 3H), 1.7-2.1(m, 2H), 2.4-2.6(m, 2H), 3.46(s, 3H), 3.0-3.8(m, 5H), 4.7-5.1(m, 4H), 5.8-6.0(m, 1H), 7.68(d, J=13.2Hz, 1H), 8.60(s, 1H) | DMSO + Et₃N |
| 83 | H | (H₂N-cyclobutyl) | C—OMe | Pale yellow solid | 200.5-203 | [DMSO-d₆]: 3.50(s, 3H), 3.7-4.0, 4.35-4.55(m, 5H), 4.7-5.1(m, 4H), 5.8-6.0(m, 1H), 7.68(d, J=13.7Hz, 1H), 8.59(s, 1H) | DMSO + Et₃N |
| 84 | H | (MeHN-CH₂-pyrrolidine) | C—OMe | Colorless solid | 202-204 | [DMSO-d₆]: 1.5-2.2(m, 2H), 2.30(s, 3H), 3.49(s, 3H), 2.3-3.8(m, 7H), 4.6-5.1(m, 4H), 5.8-6.0(m, 1H), 7.68(d, J=14.2, Hz, 1H), 8.61(s, 1H) | DMSO + Et₃N |
| 86 | —NH₂ | (H₂N, MeO-pyrrolidine, Trans-form) | CF | Pale yellowish green solid | 161-164 | [CDCl₃ + DMSO-d₆]: 3.43(s, 3H), 3.2-4.2(m, 6H), 4.8-5.2(m, 4H), 5.6-5.8(m, 1H), 6.6-6.9(br, 2H), 8.52(s, 1H) | DMSO + Et₃N |

TABLE 9-continued

[Structure: quinolone core with R² at 5-position, F at 6-position, Z at 7-position, Y at 8-position, N-cyclobutyl(oxetane) at 1-position, COOH at 3-position, =O at 4-position]

| Comp'd. No. | R² | Z | Y | Appearance | Melting point (°C.) | [Solvent] ¹H-NMR | Reaction solvent |
|---|---|---|---|---|---|---|---|
| 87 | H | H₂N—[pyrrolidine]—OMe (Trans-form) | CH | Gray solid | 132-133 | [DMSO-d₆ + D₂O]: 3.33(s, 3H), 3.2-4.1(m, 6H), 4.8-5.2 (m, 4H), 5.8-6.0(m, 1H), 6.2-6.4(m, 1H), 7.83 (d, J=13.6Hz, 1H), 8.61(s, 1H) | DMSO + Et₃N |
| 89 | H | H₂N—[pyrrolidine]—OMe (Cis-form) | CF | Pale yellow solid | 191-195 | [DMSO-d₆]: 3.45(s, 3H), 3.2-3.9(m, 6H), 4.8-5.1 (m, 4H), 5.75-5.9(m, 1H), 7.73(d, J=13.6Hz, 1H), 8.64(s, 1H) | DMSO + Et₃N |
| 90 | —NH₂ | H₂N—[pyrrolidine]—OMe (Cis-form) | CF | Pale yellow solid | 183-187 | [DMSO-d₆]: 3.34(s, 3H), 3.1-3.9(m, 6H), 4.75-5.0 (m, 4H), 5.6-5.8(m, 1H), 7.1-7.3(br, 2H), 8.44(s, 1H) | DMSO + Et₃N |

TABLE 9-continued

| Comp'd. No. | R² | Z | Y | Appearance | Melting point (°C.) | [Solvent] ¹H-NMR | Reaction solvent |
|---|---|---|---|---|---|---|---|
| 91 | H | MeN-H / Me (Trans-form) | CF | Pale yellow solid | 252–254 | [DMSO-d₆]: 0.97(d, J=6.84Hz, 3H), 2.29(s, 3H), 2.2–2.4 (m, 1H), 3.0–3.9(m, 5H), 4.8–5.1(m, 4H), 5.7–5.9(m, 1H), 7.72(d, J=13.7Hz, 1H), 8.64(s, 1H) | DMSO + Et₃N |
| 92 | —NH₂ | MeN-H / Me (Trans-form) | CF | Pale yellow solid | 197–201 | [DMSO-d₆]: 0.96(d, J=6.84Hz, 3H), 2.29(s, 3H), 2.2–2.4 (m, 1H), 3.0–3.9(m, 5H), 4.7–5.0(m, 4H), 5.6–5.8(m, 1H), 7.1–7.3(br, 2H), 8.43(s, 1H) | DMSO + Et₃N |
| 93 | H | Me / MeN-H (Cis-form) | CF | Pale yellow solid | 256–258 | [DMSO-d₆]: 1.03(d, J=6.34Hz, 3H), 1.95–2.1(m, 1H), 2.31(s, 3H), 2.6–4.0(m, 5H), 4.8–5.1(m, 4H), 5.7–5.9(m, 1H), 7.74(d, J=13.7Hz, 1H), 8.65(s, 1H) | DMSO + Et₃N |

TABLE 9-continued

| Comp'd. No. | R² | Z | Y | Appearance | Melting point (°C.) | [Solvent] ¹H-NMR | Reaction solvent |
|---|---|---|---|---|---|---|---|
| 94 | —NH₂ | Me, N- pyrrolidinyl with MeNH (Cis-form) | CF | Pale yellow solid | 203–206 | [DMSO-d₆]: 1.03(d, J=6.35Hz, 3H), 1.9–2.1(m, 1H), 2.31(s, 3H), 2.6–3.9(m, 5H), 4.7–5.0(m, 4H), 5.6–5.8(m, 1H), 7.0–7.3(br, 2H), 8.43(s, 1H) | DMSO + Et₃N |
| 95 | H | 3-(1,1-dimethylhydrazino)pyrrolidinyl | CF | Pale yellow solid | 150–151.5 | [DMSO-d₆ + D₂O]: 1.9–2.3(m, 2H), 2.57(s, 6H), 3.0–3.9 (m, 5H), 4.8–5.1(m, 4H), 5.7–5.9(m, 1H), 7.78 (d, J=13.5Hz, 1H), 8.66(s, 1H) | DMSO + Et₃N |
| 96 | —NH₂ | 3-(1,1-dimethylhydrazino)pyrrolidinyl | CF | Yellow solid | 242–245 | [DMSO-d₆]: 2.0–2.4(m, 2H), 2.79(s, 6H), 2.9–3.9 (m, 5H), 4.7–5.0(m, 4H), 5.6–5.8(m, 1H), 7.1–7.3(br, 2H) 8.47(s, 1H) | DMSO + Et₃N |
| 101 | —NH₂ | H₂N, Me pyrrolidinyl (Cis-form) | CF | Yellow solid | 217–220 | [DMSO-d₆]: 1.10(d, J=6.3Hz, 3H), 2.0–2.2(m, 1H), 2.8–4.2(m, 5H), 4.75–5.1(m, 4H), 5.6–5.8(m, 1H), 7.1–7.4(br, 2H), 8.45(s, 1H) | DMSO + Et₃N |

TABLE 9-continued

![Structure: fluoroquinolone with R2, Y, Z substituents and N-oxetanyl group]

| Comp'd. No. | R² | Z | Y | Appearance | Melting point (°C.) | [Solvent] ¹H-NMR | Reaction solvent |
|---|---|---|---|---|---|---|---|
| 102 | H | H₂N—[pyrrolidinyl]—Me (Trans-form) | CF | Pale yellow solid | 227–230 | [CDCl₃ + DMSO-d₆]: 1.13(d, J=6.84Hz, 3H), 2.2–2.45 (m, 1H), 3.4–4.1(m, 5H), 4.85–5.1(m, 4H), 5.75–5.95(m, 1H), 7.76(d, J=13.7Hz, 1H), 8.69(s, 1H) | DMSO + Et₃N |
| 103 | —NH₂ | H₂N—[pyrrolidinyl]—Me (Trans-form) | CF | Pale yellow solid | 234–238 | [DMSO-d₆]: 0.98(d, J=6.83Hz, 3H), 2.05–2.25(m, 1H) 3.1–3.8(m, 5H), 4.75–5.1(m, 4H), 5.6–5.8(m, 1H), 7.05–7.3(br, 2H), 8.42(s, 1H) | DMSO + Et₃N |
| 106 | H | HO—N[piperazinyl]N— | CF | Pale yellow solid | 242–245 | [DMSO-d₆]: 2.5–3.5(m, 8H), 4.8–5.1(m, 4H) (5.8–6.0 (m, 1H), 7.86(d, J=12.2Hz, 1H), 8.76(s, 1H) | DMSO + Et₃N |
| 107 | —NH₂ | HO—N[piperazinyl]N— | CF | Yellow solid | 224–227 | [DMSO-d₆]: 2.5–3.5(m, 8H), 4.7–5.0(m, 4H), 5.6–5.8 (m, 1H), 7.2–7.4(br, 2H), 8.54(s, 1H) | DMSO + Et₃N |

EXAMPLE 27

7-(Cis-3-amino-4-methylpyrrolidin-1-yl)-6,8-difluoro-1-(oxetan-3-yl)-1,4-dihydro-4-oxoquinoline-3-carboxylic acid trifluoroacetic acid salt (Compound No. 97)

200 mg of Compound No. 3, 160 mg of cis-3-t-butoxycarbonylamino-4-methylpyrrolidine and 150 mg of triethylamine were reacted at 80° C. for 1 hour in 3 ml of DMF. DMF was distilled off and ether was added to the residue. The resultant solid was collected by filtration. The solid was dissolved in 10 ml of chloroform, followed by the addition of 2 ml of trifluoroacetic acid under ice cooling. They were reacted at the same temperature for 10 minutes and then at room temperature for further 40 minutes. Volatile components were distilled off. To the residue were added 2 ml of ethanol and 30 ml of hexane. The resultant mixture was stirred and the supernatant was removed by decantation. To the oily residue was added 5 ml of ethanol so that the latter was solidified. The solid thus formed was ground and collected by filtration, whereby 150 mg of the title compound was obtained as a yellow solid.

Melting point: 225°–227° C.

$^1$H-NMR (DMSO-$d_6$) δ: 1.14(d,J=6.35Hz,3H), 2.25–2.4(m,1H), 3.0–4.1(m,5H), 4.8–5.2(m,4H), 5.7–6.0(m,1H), 7.76(d,J=14.2Hz,1H), 8.67(s,1H).

EXAMPLE 28

Compound Nos. 98–100 and 197–214, which are shown in Table 10, were obtained in a similar manner to Example 27.

TABLE 10

[Structure: quinolone core with R² at 7-position, F at 6, Y at 5 (labeled differently), Z at 7-position, N-oxetanyl at N1, COOH at 3]

| Comp'd. No. | R² | Z | Y | Appearance | Melting point (°C.) | [Solvent] ¹H-NMR | Reaction solvent |
|---|---|---|---|---|---|---|---|
| 98 | NH₂ | H₂N−[pyrrolidinyl]−Me .CF₃COOH (Cis-form) | CF | Yellow solid | 229–234 | [DMSO-d₆]: 1.12(d, J=6.35Hz, 3H), 2.2-2.4(m, 1H), 3.1-4.1(m, 5H), 4.7-5.0(m, 4H), 5.6-5.8(m, 1H), 7.1-7.3(br, 2H), 8.46(s, 1H) | DMF + Et₃N |
| 99 | H | H₂N−[pyrrolidinyl]−Me .CF₃COOH (Trans-form) | CF | Pale Yellow solid | 220–224 | [DMSO-d₆]: 1.10(brs, 3H), 2.4-2.7(m, 1H), 3.1-4.2 (m, 5H), 4.8-5.2(m, 4H), 5.7-6.0(m, 1H), 7.78(d, J=13.2Hz, 1H), 8.66(s, 1H) | DMF + Et₃N |
| 100 | —NH₂ | H₂N−[pyrrolidinyl]−Me .CF₃COOH (Trans-form) | CF | Yellow solid | 237–240.5 | [DMSO-d₆]: 1.08(d, J=5.86Hz, 3H), 2.4-2.6(m, 1H), 3.2-4.2(m, 5H), 4.7-5.1(m, 4H), 5.6-5.8(m, 1H), 7.1-7.5(br, 2H), 8.45(s, 1H) | DMF + Et₃N |

TABLE 10-continued

| Comp'd. No. | R² | Z | Y | Appearance | Melting point (°C.) | [Solvent] ¹H-NMR | Reaction solvent |
|---|---|---|---|---|---|---|---|
| 197 | H | .CF₃COOH<br>(structure: bicyclic amine with HN and N—)<br>(1S, 4S) | =N— | Pale yellow solid | 202–207 | [DMSO-d₆]: 1.9–2.2(m, 2H), 3.94(s, 2H), 4.53(s, 1H), 4.95–5.2(m, 4H), 5.17(s, 1H), 5.7–5.9(m, 1H), 8.15(d, J=12.2Hz, 1H), 8.65(s, 1H), 9.1–9.6(br, 2H) | Pyridine + DBU |
| 198 | H | .CF₃COOH<br>(structure: bicyclic amine with HN and N—)<br>(1S, 4S) | CF | Pale yellow solid | 240–243 | [DMSO-d₆]: 1.85–2.25(m, 2H), 3.5–3.7(m, 2H), 3.85–4.0(m, 1H), 4.47(s, 1H), 4.82(s, 1H), 4.85–5.1(m, 4H), 5.75–5.95(m, 1H), 7.83 (d, J=14.2Hz, 1H), 8.67(s, 1H), 9.10(brs, 2H) | Pyridine + DBU |
| 199 | H₂N | .CF₃COOH<br>(structure: bicyclic amine with HN and N—)<br>(1S, 4S) | CF | Pale yellow solid | 234–237 | [DMSO-d₆]: 1.8–2.0(m, 1H), 2.05–2.2(m, 1H), 3.45–3.6(m, 1H), 3.8–4.0(m, 1H), 4.44(s, 1H), 4.6–5.1(m, 4H), 5.55–5.8(m, 1H), 7.29(brs, 2H), 8.46(s, 1H), 8.6–9.2(br, 2H) | Pyridine + DBU |
| 200 | H | (structure: pyrrolidine with H₂N and HO substituents, N—)<br>(Isomer A) | CF | Slightly yellow powder | 168–175 | [DMSO-d₆]: 2.3–2.55(m, 1H), 3.55(brs, 2H), 4.85–5.05 (m, 4H), 5.75–6.0(m, 1H), 7.81(d, J=13.7Hz, 1H), 8.22(brs, 3H), 8.68(s, 1H) | DMSO + Et₃N |

TABLE 10-continued

[Structure: quinolone core with R² at position, F, Z, Y substituents, N-cyclobutyl-like (oxetane) group, COOH]

| Comp'd. No. | R² | Z | Y | Appearance | Melting point (°C.) | [Solvent] ¹H-NMR | Reaction solvent |
|---|---|---|---|---|---|---|---|
| 201 | H₂N | H₂N-[pyrrolidine with CH₂OH]·CF₃COOH (Isomer A) | CF | Pale yellow powder | 221–224 | [DMSO-d₆]: 2.35–2.5(m, 1H), 3.54(brs, 2H), 3.69 (brs, 2H), 4.75–5.1(m, 4H), 5.6–5.8(m, 1H), 8.20 (brs, 3H), 8.48(s, 1H) | DMSO + Et₃N |
| 202 | H | H₂N-[pyrrolidine with CH₂OH]·CF₃COOH (Isomer B) | CF | Pale yellow powder | 197–201 | [DMSO-d₆]: 2.55–2.7(m, 1H), 4.0–4.15(m, 1H), 4.8–5.05(m, 4H), 5.75–5.9(m, 1H), 7.80 (d, J=13.67Hz, 1H), 8.04(brs, 3H), 8.68(s, 1H) | DMSO + Et₃N |
| 203 | H₂N | H₂N-[pyrrolidine with CH₂OH]·CF₃COOH (Isomer B) | CF | Yellow powder | 224–248 | [DMSO-d₆]: 2.52–2.7(m, 1H), 3.9–4.1(m, 1H), 4.75–5.0 (m, 4H), 5.6–5.8(m, 1H), 6.9–7.6(br, 2H), 8.04(brs, 3H), 8.47(s, 1H) | DMSO + Et₃N |
| 204 | H | H₂N-[Me-pyrrolidine]·CF₃COOH (Isomer A) | CF | Pale yellow powder | 203–208 | [DMSO-d₆]: 1.13(d, J=5.86Hz, 3H), 2.0–2.35(m, 2H), 4.3–4.5(m, 1H), 4.85–5.1(m, 4H), 5.8–6.0(m, 1H), 7.87(d, J=12.7Hz, 1H), 8.16(brs, 3H), 8.72(s, 1H) | DMSO + Et₃N |

TABLE 10-continued

Structure:
R² substituent on a bicyclic quinolone core with F, Y, Z substituents, N-linked oxetanyl group, and COOH group.

| Comp'd. No. | R² | Z | Y | Appearance | Melting point (°C.) | ¹H-NMR [Solvent] | Reaction solvent |
|---|---|---|---|---|---|---|---|
| 205 | H₂N | Me-pyrrolidinyl with H₂N (Isomer A)·CF₃COOH | CF | Yellow powder | 228-231 | [DMSO-d₆]: 1.11(d, J=6.84Hz, 3H), 2.0-2.38(m, 2H) 3.8-4.1(m, 2H), 4.3-4.45(m, 1H), 4.75-5.1(m, 4H), 5.6-5.9(m, 1H), 7.1-7.5(br, 2H), 8.13(brs, 3H), 8.51(s, 1H) | DMSO + Et₃N |
| 206 | H | Me-pyrrolidinyl with H₂N (Isomer B)·CF₃COOH | CF | Pale yellow powder | 160-178 | [DMSO-d₆]: 1.19(d, J=5.86Hz, 3H), 1.85-2.05(m, 1H), 2.25-2.4(m, 1H), 3.45-3.6(m, 2H), 4.1-4.3(m, 1H), 4.85-5.1(m, 4H), 5.8-6.0(m, 1H), 7.85(d, J=13.7Hz, 1H), 8.35(brs, 3H), 8.71(s, 1H) | DMSO + Et₃N |
| 207 | H₂N | Me-pyrrolidinyl with H₂N (Isomer B)·CF₃COOH | CF | Yellow powder | 230-234 | [DMSO-d₆]: 1.19(d, J=6.35Hz, 3H), 1.8-2.05(m, 1H), 2.2-2.4(m, 1H), 3.8-4.0(m, 1H), 4.05-4.25(m, 1H), 4.8-5.05(m, 4H), 5.65-5.8(m, 1H), 7.1-7.5(br, 2H), 8.31(brs, 3H), 8.50(s, 1H) | DMSO + Et₃N |
| 208 | H | Et-pyrrolidinyl with H₂N ·CF₃COOH (Cis-form:Trans-form = 1:1) | CF | Yellow powder | 152-160 | [DMSO-d₆]: 0.8-1.0(m, 3H), 1.3-1.65(m, 2H), 2.1-2.3 and 2.3-2.45(m, 1H), 3.45-4.2(m, 5H), 4.87-5.1 (m, 4H), 5.8-5.95(m, 1H), 7.79(d, J=13.7Hz, 1H), 8.05-8.35(m, 3H), 8.68 and 8.67(s, two peaks, 1H) | DMSO + Et₃N |

TABLE 10-continued

| Comp'd. No. | R² | Z | Y | Appearance | Melting point (°C.) | [Solvent] ¹H-NMR | Reaction solvent |
|---|---|---|---|---|---|---|---|
| 209 | H | (octahydropyrrolo-pyrrole)·CF₃COOH | CF | Pale yellow powder | 246–248 | [DMSO-d₆]: 3.04(s, 4H), 3.4–3.75(m, 6H), 4.85–5.1 (m, 4H), 5.8–5.95(m, 1H), 7.83(dd, J=11.2Hz, J=1.95Hz, 1H), 8.70(s, 1H), 8.97(brs, 2H) | DMSO + Et₃N |
| 210 | H₂N | (octahydropyrrolo-pyrrole)·CF₃COOH | CF | Yellow powder | 250–252 | [DMSO-d₆]: 3.01(s, 4H), 3.35–3.75(m, 6H), 4.8–5.0 (m, 4H), 5.6–5.8(m, 1H), 7.1–7.5(m, 2H), 8.47(s, 1H), 8.99(brs, 2H) | DMSO + Et₃N |
| 211 | H | 3-methylpiperazine·CF₃COOH | CH | Pale yellow powder | 131–140 | [DMSO-d₆]: 1.18(d, J=6.84Hz, 3H), 3.1–3.6(m, 7H), 4.95–5.1(m, 4H), 5.95–6.1(m, 1H), 7.00(d, J=6.84Hz, 1H), 8.00(d, J=12.7Hz, 1H), 8.77(s, 1H), 8.8–9.1(br, 1H), 9.1–9.4(br, 1H) | DMSO + Et₃N |
| 212 | H | 3-methylpiperazine·CF₃COOH | CF | Yellow powder | 198–205 | [DMSO-d₆]: 1.00(d, J=6.35Hz, 3H), 2.8–3.05(m, 1H), 3.1–3.4(m, 5H), 3.6–3.75(m, 1H), 4.85–5.1(m, 4H), 5.75–6.0(m, 1H), 7.97(d, J=12.2Hz, 1H), 8.83(s, 1H), 8.9–9.2(m, 2H) | DMSO + Et₃N |

TABLE 10-continued

[Structure shown: quinolone core with R² at top-left position, F, Y, Z substituents on benzene ring, COOH at position 3, carbonyl, N-oxetanyl group]

| Comp'd. No. | R² | Z | Y | Appearance | Melting point (°C.) | [Solvent] ¹H-NMR | Reaction solvent |
|---|---|---|---|---|---|---|---|
| 213 | H₂N | (Trans-form) Et—[pyrrolidine with H₂N]—N— · CF₃COOH | CF | Yellow powder | 259–264 | [DMSO-d₆]: 0.96(t, J=7.4Hz, 3H), 1.25–1.6(m, 2H) 2.3–2.45(m, 1H), 3.5–3.75(m, 2H), 3.8–3.9(m, 1H) 4.0–4.1(m, 1H), 4.75–5.0(m, 4H), 5.6–5.75(m, 1H), 7.25(brs, 2H), 8.47(s, 1H) | DMSO + Et₃N |
| 214 | H₂N | (Cis-form) Et—[pyrrolidine with H₂N]—N— · CF₃COOH | CF | Yellow powder | 219–225 | [DMSO-d₆]: 0.94(t, J=7.3Hz, 3H), 1.25–1.45(m, 1H) 1.55–1.75(m, 1H), 2.05–2.2(m, 1H), 3.55–3.75(m, 1H) 3.8–4.0(m, 2H), 4.75–5.0(m, 4H), 5.6–5.8(m, 1H), 7.26(brs, 2H), 8.48(s, 1H) | DMSO + Et₃N |

EXAMPLE 29

7-(Trans-3-amino-4-methylpyrrolidin-1-yl)-6,8-difluoro-1-(oxetan-3-yl)-1,4-dihydro-4-oxoquinoline-3-carboxylic acid hydrochloride (Compound No. 104)

70 mg of Compound No. 102 was suspended in 3 ml of ethanol. Under ice cooling, HCl-saturated ethanol was added little by little until the compound was completely dissolved. 3 ml of ether was added and the resultant solid was collected by filtration, whereby 60 mg of the title compound was obtained as a pale yellow solid.

Melting point: 188°–190° C.

$^1$H-NMR (DMSO-$d_6$) δ: 1.10(d,J=6.83Hz,3H), 2.4–2.6(m,1H), 3.2–4.2(m,5H), 4.8–5.1(m,4H), 5.75–6.0(m,1H), 7.79(d,J=13.7Hz,1H), 8.67(s,1H).

EXAMPLE 30

5-Amino-7-(trans-3-amino-4-methylpyrrolidin-1-yl)-6,8-difluoro-1-(oxetan-3-yl)-1,4-dihydro-4-oxoquinoline-3-carboxylic acid hydrochloride (Compound No. 105)

Using 100 mg of Compound No. 103, 90 mg of the title compound was obtained as a pale yellow solid by similar procedures to Example 29.

Melting point: ≧260° C. (decomposed).

$^1$H-NMR (DMSO-$d_6$) δ: 1.08(d,J=6.84Hz,3H), 2.4–2.6(m,1H), 3.5–4.2(m,5H), 4.7–5.1(m,4H), 5.6–5.9(m,1H), 7.2–7.4(br,2H), 8.45(s,1H).

EXAMPLE 31

5-Amino-6,8-difluoro-7-(4-formimidoylpiperazin-1-yl)-1-(oxetan-3-yl)-1,4-dihydro-4-oxoquinoline-3-carboxylic acid hydrochloride (Compound No. 108)

100 mg of Compound No. 55 and 100 mg of DBU were stirred in 8 ml of ethanol, followed by the addition of 68 mg of benzyl formimidate hydrochloride at room temperature. They were reacted for 1 hour. HCl-saturated ethanol was added to the reaction mixture, so that the reaction mixture was rendered weakly acidic. The resulting solid was collected by filtration and washed with 5 ml of ether, whereby 83 mg of the title compound was obtained as a pale yellow solid.

Melting point: 240°–245° C.

$^1$H-NMR (DMSO-$d_6$) δ: 3.0–3.8(m,8H), 4.8–5.1(m,4H), 5.7–5.9(m,1H), 7.3–7.6(br,2H), 8.09(s,1H), 8.56(s,1H).

EXAMPLE 32

Compound Nos. 109–111 shown in Table 11 were obtained in a similar manner to Example 31.

TABLE 11

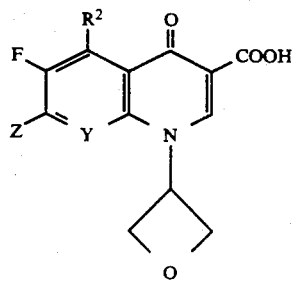

| Comp'd. No. | R$^2$ | Z | Y | Appearance | Melting point (°C.) | [Solvent] $^1$H-NMR | Reaction solvent |
|---|---|---|---|---|---|---|---|
| 109 | —NH$_2$ | HN=C(Me)–N(piperazine)N— ·HCl | CF | Yellow solid | 232–235 | [DMSO-$d_6$]: 2.34(s, 3H), 3.1–3.8(m, 8H) 4.75–5.1(m, 4H), 5.6–5.9(m, 1H), 7.2–7.6(br, 2H), 8.56(s, 1H) | EtOH + DBU |
| 110 | —NH$_2$ | HN=CH–NH–(pyrrolidine)N— ·HCl | CF | Yellow solid | 182–185 | [DMSO-$d_6$]: 1.7–2.2(m, 2H), 3.3–3.9(m, 5H), 4.7–5.1(m, 4H), 5.6–5.8(m, 1H), 7.1–7.3 (br, 2H), 7.60(s, 1H), 8.41(s, 1H) | EtOH + DBU |
| 111 | H | HN=CH–NH–(pyrrolidine)N— ·HCl | N | Colorless solid | 270–273 | [DMSO-$d_6$]: 1.8–2.4(m, 2H), 3.2–4.4(m, 5H), 4.9–5.1(m, 4H), 5.7–5.9(m, 1H), 7.92(s, 1H), 8.07(d, J=13.7Hz, 1H), 8.61(s, 1H) | EtOH |

EXAMPLE 33

5-Amino-7-{(−)-trans-3-amino-4-methylpyrrolidin-1-yl}-6,8-difluoro-1-(oxetan-3-yl)-1,4-dihydro-4-oxoquinoline-3-carboxylic acid (Compound No. 113)

(1) In the presence of triethylamine, 59 g of benzoyl chloride was reacted at room temperature with 81.4 g of trans-3-tert-butoxycarbonylamino-4-methylpyrrolidine in methylene chloride, whereby 120 g of trans-3-tertbutoxycarbonylamino-4-methyl-1-benzoylpyrrolidine (a) was obtained. Hydrochloric acid was then reacted at room temperature with 123 g of the compound (a) in ethanol, so that 83 g of trans-3-amino-4-methyl-1-benzoylpyrrolidine (b) was obtained. In methylene chloride, 68.4 g of (R)-(—)mandelic acid was then reacted at room temperature with 83 g of the compound (b) in the presence of 87.3 g o 1-hydroxybenzotriazole, 87.4 g of 1-ethyl-3-(3-dimethylaminopropyl)carbodiimide hydrochloride and 46.5 g of triethylamine. 34 g of trans-3-(2-(R)-2-phenyl-2-hydroxyacetylamino)-4-methyl-1-benzoylpyrrolidine diastereomer (A), (c) was obtained. Acetic acid and hydrochloric acid were then reacted with the compound (c) under reflux, whereby 16.8 g of (—)-trans-3-amino-4-methylpyrrolidine dihydrochloride was obtained as a colorless solid.

[α]$_D^{20}$: −10.9° (c=0.53, MeOH)

$^1$H-NMR (CD$_3$OD) δ: 1.22(d,J=7.3HZ,3H), 2.7–2.85(m,1H), 3.2–3.35(m,1H), 3.4–3.7(m,2H), 3.75–4.1(m,2H).

(2) Using 22 g of Compound No. 26, 16.5 g of the (—)-trans-3-amino-4-methylpyrrolidine dihydrochloride obtained in the above procedure (1), 43.4 g of triethylamine and 250 ml of DMSO, 22 g of the title compound was obtained as pale yellow powder by similar procedures to Example 25. The powder was dissolved under heat and reflux in 2 l of methanol. After insoluble matter was filtered off, the methanol solution was allowed to cool down so that the powder was crystallized. 15 g of the title compound was obtained as pale yellow needle crystals.

Melting point: 270°–275° C. (decomposed).

$^1$H-NMR (DMSO-d$_6$) δ: 1.07(d,J=7.33Hz,3H), 2.4–2.6(m,1H), 3.4–4.1(m,5H), 4.7–5.1(m,4H), 5.6–5.8(m,1H), 7.1–7.4(brs,2H), 8.45(s,1H), 9.0–10.00(br,2H).

EXAMPLE 34

5-Amino-7-{(—)-trans-3-amino-4-methylpyrrolidin-1-yl}-6,8-difluoro-1-(oxetan-3-yl)-1,4-dihydro-4-oxoquinoline-3-carboxylic acid methanesulfonic acid salt (Compound No. 114)

In a liquid mixture consisting of 50 ml of ethanol and 10 ml of water, 850 mg of Compound No. 113 and 934 mg of methanesulfonic acid were stirred at 45° C. for 20 minutes. Insoluble matter was filtered off and 400 ml of ether was added to the filtrate. The resulting solid was collected by filtration and washed with ether, whereby 670 mg of the title compound was obtained as yellow powder.

Melting point: 242°–245° C. (decomposed).

$^1$H-NMR (DMSO-d$_6$) δ: 1.08(d,J=6.8Hz,3H), 2.33(s,3H), 2.5–2.6(m,1H), 3.5–4.1(m,5H), 4.75–5.0(m,4H), 5.6–5.8(m,1H), 7.1–7.4(br,2H), 8.09(brs,3H), 8.45(s,1H).

EXAMPLE 35

5-Amino-7-{(—)-trans-3-amino-4-methylpyrrolidin-1-yl}-6,8-difluoro-1-(oxetan-3-yl)-1,4-dihydro-4-oxoquinoline-3-carboxylic acid p-toluene sulfonic acid salt (Compound No. 115)

500 mg of Compound No. 113 was suspended in 50 ml of ethanol, followed by the addition of 30 ml of an ethanol solution of 725 mg of p-toluenesulfonic acid monohydrate and 80 ml of chloroform. They were stirred at 45° C. for 10 minutes. Insoluble matter was filtered off. The filtrate was subjected to distillation under reduced pressure, so that chloroform was removed. 400 ml of ether was added and the resulting solid was collected by filtration, so that 584 mg of the title compound was obtained as yellow powder.

Melting point: 174°–190° C.

$^1$H-NMR (DMSO-d$_6$) δ: 1.08(d,J=6.8Hz,3H), 2.28(s,3H), 2.4–2.6(m,1H,), 3.4–4.1(m,5H), 4.7–5.1(m,4H), 5.6–5.8(m,1H), 7.1 and 7.47(d,J=7.8Hz,4H), 8.07(brs,3H), 8.45(s,1H).

EXAMPLE 36

5-Amino-7-((—)-trans-3-amino-4-methylpyrrolidin-1-yl}-6,8-difluoro-1-(oxetan-3-yl)-1,4-dihydro-4-oxoquinoline-3-carboxylic acid hydrochloride (Compound No. 116)

100 mg of Compound No. 113 was dissolved in a liquid mixture consisting of 5 ml of water and 5 ml of ethanol, followed by the addition of 3 ml of 1N-HCl under ice cooling. They were stirred for 5 minutes. 30 ml of ether was added and the resulting solid was collected by filtration, whereby 70 mg of the title compound was obtained as yellow powder.

Melting point: 265°–275° C. (decomposed).

$^1$H-NMR (DMSO-d$_6$) δ: 1.09(d,J=6.8Hz,3H), 2.4–2.6(m,1H), 3.5–4.1(m,5H), 4.7–5.1(m,4H), 5.6–5.8(m,1H), 7.1–7.4(br,2H), 8.45(s,1H), 8.3–8.7(brs,3H).

EXAMPLE 37

5-Amino-7-{(—)-trans-3-amino-4-methylpyrrolidin-1-yl}-6,8-difluoro-1-(oxetan-3-yl)-1,4-dihydro-4-oxoquinoline-3-carboxylic acid sulfuric acid salt (Compound No. 117)

1 g of Compound No. 113 was dissolved in a liquid mixture consisting of 6 ml of water and 18 ml of ethanol, followed by the addition of 1.53 g of sulfuric acid (97%) at 10°–15° C. They were stirred for 10 minutes. The resulting solid was collected by filtration, washed with ethanol (10 ml, twice) and ether (10 ml, twice), whereby 1.08 g of the title compound was obtained as a pale yellow solid.

Melting point: ≧290° C. (colored and decomposed).

$^1$H-NMR (DMSO-d$_6$) δ: 1.09(d,J=6.8Hz,3H), 2.5–2.7(m,1H), 3.5–4.1(m,5H), 4.7–5.1(m,4H), 5.6–5.8(m,1H), 7.1–7.4(br,2H), 7.9–8.2(br,3H), 8.45(s,1H).

EXAMPLE 38

6-Fluoro-7-[(2S,4S)-2-methyl-4-aminopyrrolidin-1-yl]-1-(oxetan-3-yl)-1,4-dihydro-4-oxoquinoline-3-carboxylic acid [Compound No. 215)

100 g Of Compound No. 34, 172 mg of (2S,4S)-2-methyl-4-benzyloxycarbonylaminopyrrolidine hydrochloride and 172 mg of triethylamine were reacted at 80° C. for 2.5 hours in 2 ml of dimethylformamide. After the solvent was distilled off, the residue was subjected to columnchromatography on silica gel (chloroform/methanol=10/1) and the corresponding fractions were collected. The solvent was distilled off and the residue was dissolved in 60 ml of methanol. 100 mg of palladium/carbon was added to the solution. A reaction was then conducted for 2 days under hydrogen gas. After the catalyst was filtered off, the filtrate was distilled. The residue was solidified with 5 ml of ethanol and then ground, so that 35 mg of the title compound was obtained as a pale yellow solid.

Melting point: ≧217° C. (decomposed).

$^1$H-NMR (DMSO-d$_6$) δ: 1.18(s,3H), 1.95-2.15(m,1H), 2.25-2.5(m,1H), 3.99(brs,1H), 4.85-5.2(m,4H), 5.8-6.05(m,1H), 6.55(brs,1H), 7.91(d,J=13.67Hz,1H), 8.65(s,1H).

EXAMPLE 39

Compound Nos. 216 and 217 shown in Table 12 were obtained in a similar manner to Example 38.

TABLE 12

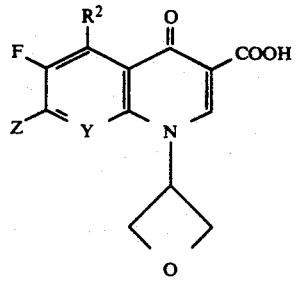

| Comp'd. No. | R$^2$ | Z | Y | Appearance | Melting point (°C.) | [Solvent] $^1$H-NMR | Reaction solvent |
|---|---|---|---|---|---|---|---|
| 216 | H | CH$_3$—N<(CH$_2$)—NH$_2$COOH (2S, 4S) | CF | Pale yellow powder | 170-174 | [DMSO-d$_6$]: 1.05-1.15(m, 3H), 1.6-1.8(m, 1H), 2.3-2.45(m, 1H), 3.55-3.7(m, 1H), 4.87-5.10 (m, 4H), 5.8-5.95(m, 1H), 7.75(d, J=13Hz, 1H), 8.7(s, 1H) | DMSO + Et$_3$N |
| 217 | H$_2$N | CH$_3$—N<(CH$_2$)—NH$_2$COOH (2S, 4S) | CF | Yellow powder | 180-189 | [DMSO-d$_6$]: 1.12(s, 3H), 1.8-2.0(m, 1H), 2.2-2.45(m, 1H), 2.95-3.15(m, 1H), 4.8-5.1(m, 4H), 5.65-5.8(m, 1H), 7.31(brs, 2H), 8.49(s, 1H) | DMSO + Et$_3$N | whereby 4.7 g of 6-benzyloxy-2,3,4-trifluorobenzoic acid was obtained as colorless powder.

After 4.6 g of the benzoic acid derivative was reacted with 3 ml of oxalyl chloride at room temperature for 1 hour in 20 ml of dichloromethane which had been added with a single droplet of dimethylformamide, excess reagents and solvent were distilled off. An acid chloride was thus obtained as an oily residue. Into a homogeneous solution which had been obtained reacting 390 mg of magnesium and 2.8 g of diethyl malonate in a liquid mixture consisting of 2.5 ml of ethanol and 20 ml of tetrahydrofuran and which was cooled at −40° C., a solution of the above acid chloride in 10 ml of tetrahydrofuran was added dropwise so that they were reacted. The temperature of the reaction mixture was allowed to rise to room temperature, followed by the distillation of the solvents. The residue was added with 2 ml of concentrated hydrochloric acid, 20 ml of water and 50 ml of chloroform, followed by separation into two layers. The solvent was distilled off from the chloroform layer. To the residue were added 0.5 g of p-toluenesulfonic acid monohydrate and 30 ml of water. They were reacted at about 100° C. for 2 hours. The reaction mixture was allowed to cool to room temperature, followed by extraction with 50 ml of chloroform. The chloroform layer was washed with 5% aq. sodium hydrogencarbonate solution and was then treated with anhydrous magnesium sulfate, whereby ethyl 6-benzyloxy-2,3,4-trifluorobenzoylacetate was obtained as an oily residue.

1.76 g of the ethyl benzoylacetate was dissolved in 15 ml of benzene, followed by the addition of 0.66 g of dimethylformamide dimethylacetal. They were reacted under reflux for 45 minutes. The solvent was distilled

EXAMPLE 40

Ethyl 6,7-Difluoro-5-hydroxy-1-(oxetan-3-yl)-1,4-dihydro-4-oxoquinoline-3-carboxylate [Compound No. 218]

6.5 g of benzyl alcohol was dissolved in 150 ml of benzene. While the resultant solution was cooled with water, 2.4 g of sodium hydride (60%) was added and reacted. To the reaction mixture was added 15 g of benzyl 2,3,4,6-tetrafluorobenzoate, and stirred at room temperature for 1 hour. 3.6 g of acetic acid was added, followed by the removal of the solvent by distillation. To the residue, 6.5 g of potassium hydroxide and 50 ml of water and 100 ml of methanol were added. They were reacted at 50° C. for 30 minutes. 6 g of acetic acid was added, followed by the removal of the solvent by distillation. To the residue were added 50 ml of benzene and 7% aq. potassium hydroxide solution. The resultant mixture was shaken, followed by separation into two layers. Concentrated hydrochloric acid was added to the water layer so that the water layer was rendered acidic. The thus-acidified water layer was extracted twice with 100 ml portions of chloroform. The extract was treated with anhydrous magnesium sulfate and the solvent was distilled out. A solid thus formed was dispersed in n-hexane and then collected by filtration, off and to the residue was added 10 ml of dichloromethane and 0.5 g of 3-aminooxetane. They were reacted at room temperature for 45 minutes. The solvent was distilled off. To the residue was added 1 g of anhydrous potassium carbonate and 5 ml of dimethylformamide, followed by a reaction at 100° C. for 1 hour. After the reaction mixture was allowed to cool down, 40 ml of chloroform and 250 ml of water were added to the reaction mixture. The thus-prepared mixture was then allowed to separate into two layers. The chloroform layer was washed with water and then treated with anhydrous magnesium sulfate. The solvent was distilled off. Crystals thus precipitated were dispersed in a liquid mixture of diisopropyl ether and chloroform and then collected by filtration, whereby 810 mg of ethyl 5-benzyloxy-6,7-difluoro-1-(oxetan-3-yl)-1,4-dihydro-4-oxoquinolin-3-carboxylate was obtained (m.p. 220°–222° C.).

1.62 g of the ethyl quinolonecarboxylate derivative and 250 mg of 10% palladium/carbon were added to a liquid mixture which consisted of 8 ml of dichloromethane, 8 ml of methanol and 6 ml of acetic acid. The resultant mixture was hydrogenated for 2 hours. After the catalyst was filtered off, the solvent was distilled off. A solid thus precipitated was dispersed in diisopropyl ether and then collected by filtration, whereby 1.13 g of the title compound was obtained as colorless powdery crystals.

Melting point: 242°–246° C. (decomposed).
$^1$H-NMR (CDCl$_3$) δ: 1.42(t,J=7Hz,3H), 4.43(q,J=7Hz,2H), 4.98–5.22(m,4H), 5.40–5.42(m,1H), 6.28(dd,J=11Hz,6Hz,1H), 8.59(s,1H).

EXAMPLE 41

6,7-Difluoro-5-hydroxy-1-(oxetan-3-yl)-1,4-dihydro-4-oxoquinoline-3-carboxylic acid (Compound No. 219)

315 mg of Compound No. 218 was dissolved in 80 ml of tetrahydrofuran, followed by the addition of 5.8 g of a 10% aqueous solution of tetra-n-butylammonium hydroxide. They was reacted at 45° C. for 1 hour. After 180 mg of acetic acid and 5 ml of water were added, tetrahydrofuran was distilled off. A solid thus precipitated was collected by filtration and then successively washed with ethanol and diisopropyl ether, whereby 212 mg of the title compound was obtained as colorless powdery crystals.

Melting point: 273°–276° C.
$^1$H-NMR (DMSO-d$_6$) δ: 4.90–5.18(m,4H), 5.70–5.85(m,1H), 7.17(dd,J=11Hz,6Hz, 1H), 8.79(s,1H).

EXAMPLE 42

6-Fluoro-5-hydroxy-1-(oxetan-3-yl)-7-(piperazin-1-yl)-1,4-dihydro-4-oxoquinolin-3-carboxylic acid (Compound No. 220)

In 500 mg of dimethylsulfoxide, 90 mg of Compound No. 219 and 90 mg of piperazine were reacted at 90° C. for 15 minutes. After the reaction mixture was allowed to cool down, 4 ml of diisopropyl ether was added. The resulting mixture was shaken and the supernatant was decanted with an oily precipitate left behind. This procedure was repeated three times. To the final oily precipitate was added 1 ml of ethanol. A precipitate thus formed was collected by filtration and then washed successively with ethanol and diisopropyl ether, whereby 75 mg of the title compound was obtained as pale yellow powder.

Melting point: 266°–273° C. (blackened).
$^1$H-NMR (DMSO-d$_6$) δ: 2.84–2.95(m,4H), 4.88–5.11(m,4H), 5.81–5.92(m,1H), 6.23(d,J=6Hz,1H), 8.64(s,1H).

EXAMPLE 43

Compound Nos. 221, 222, 224 and 225, which are shown in Table 13, were obtained in a similar manner to Example 42.

TABLE 13

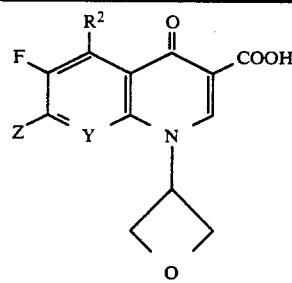

| Comp'd. No. | R$^2$ | Z | Y | Appearance | Melting point (°C.) | [Solvent] $^1$H-NMR | Reaction solvent |
|---|---|---|---|---|---|---|---|
| 221 | OH | —N(CH$_2$CH$_2$)$_2$NCH$_3$ | CH | Colorless powder | 240–245 (Decomposed) | [DMSO-d$_6$]: 2.24(s, 3H), 2.44–2.54 (m, 4H), 3.25–3.36(m, 4H), 4.89–5.10 (m, 4H), 5.81–5.92(m, 1H), 6.24(d, J=6.0Hz, 1H), 8.65(s, 1H) | DMSO |
| 222 | OH | —N(pyrrolidinyl)NH$_2$ | CH | Pale yellow powder | 286–290 (Decomposed) | | DMSO |
| 224 | OH | —N(CH$_2$CH$_2$)$_2$NH | CF | Yellow powder | 263–269 (Blackened) | [DMSO-d$_6$]: 2.78–2.88(m, 4H), 4.84–5.02 (m, 4H), 5.78–5.90(m, 1H), 8.64(s, 1H) | DMSO |

TABLE 13-continued

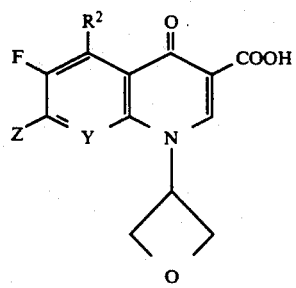

| Comp'd. No. | R² | Z | Y | Appearance | Melting point (°C.) | [Solvent] ¹H-NMR | Reaction solvent |
|---|---|---|---|---|---|---|---|
| 225 | OH | -N⟨pyrrolidinyl-NH₂⟩ | CF | Pale brown powder | 234–238 (Decomposed) | | DMSO |

EXAMPLE 44

5-Hydroxy-1-(oxetan-3-yl)-6,7,8-trifluoro-1,4-dihydro-4-oxoquinolin-3-carboxylic acid (Compound No. 223)

220 mg of 60% sodium hydride was dispersed in 50 ml of benzene, followed by the addition of 5.1 g of benzyl alcohol. They were then reacted. 1.7 g of Compound No. 23 was added, followed by a reaction at room temperature for 15 minutes. After the reaction mixture was washed twice with 250 ml portions of water, the reaction mixture was treated with anhydrous magnesium sulfate and the solvent was distilled off. To the residue was added 40 ml of diisopropyl ether. A solid thus precipitated was collected by filtration. The solid and 260 mg of 10% palladium/carbon were added to a liquid mixture which consisted of 15 ml of dichloromethane and 15 ml of methanol, followed by overnight hydrogenation. 50 ml of chloroform was added to dissolve the precipitate. The catalyst was filtered off and the filtrate was concentrated. Colorless powdery crystals thus precipitated were collected by filtration and then washed with diisopropyl ether, whereby 790 mg of the title compound was obtained.

Melting point: 242°–244° C. (blackened).

¹H-NMR (DMSO-d₆) δ: 4.87–5.05(m,4H), 5.78–5.91(m,1H), 8.78(s,1H).

EXAMPLE 45

Ethyl 5-amino-6,7-difluoro-1-(oxetan-3-yl)-1,4-dihydro-4-oxoquinolin-3-carboxylate (Compound No. 226)

60 g of methyl 2,3,4,6-tetrafluorobenzoate and 70 g of benzylamine were reacted under reflux for 1 hour in 400 ml of benzene. After the reaction mixture was allowed to cool down, it was washed successively with water, 1% hydrochloric acid and 1% aq. sodium carbonate, each in the amount of 600 ml. The reaction mixture was treated with anhydrous magnesium sulfate and then concentrated. Crystals thus precipitated were collected by filtration and thereafter washed with methanol. 30 g of the crystals and about 2 ml of palladium/carbon were added to a liquid mixture which consisted of 100 ml of acetic acid and 200 ml of methanol. The resultant mixture was hydrogenated for 1.5 hours. The catalyst was filtered off and the filtrate was concentrated, whereby methyl 6-amino-2,3,4-trifluorobenzoate was obtained as a crystalline residue.

The entire amount crystalline residue was added by portions to a liquid mixture which consisted of 200 ml of acetic acid containing 95 g of sodium perborate tetrahydrate suspended therein and 200 ml of trifluoroacetic acid and was stirred at 60° C. They were reacted at the same temperature for 1.5 hours. The solvent was concentrated to about ¼ of the original volume. Subsequent to the addition of 1 l of water, extraction was conducted twice, each with 250 ml of chloroform. The chloroform layer was washed with water and then treated with anhydrous magnesium sulfate. The solvent was distilled off to obtain a crystalline residue, to which 50 ml of 10% sulfuric acid and 60 ml of acetic acid were added. The resulting mixture was stirred under reflux for 3 days. A majority of the acetic acid was distilled off. After the addition of 60 ml of water, the mixture thus obtained was extracted four times, each with 100 ml of chloroform. The chloroform layer was treated with anhydrous magnesium sulfate and then concentrated. A colorless powdery solid thus precipitated was dispersed in a liquid mixture of chloroform and n-hexane and then collected by filtration, whereby 5.7 g of 6-nitro-2,3,4-trifluorobenzoic acid was obtained.

After 9.3 g of the benzoic acid derivative was reacted with 4.5 ml of oxalyl chloride at 40° C. for 1.5 hours in 70 ml of dichloromethane, excess reagents and solvent were distilled off. An acid chloride was thus obtained as an oily residue. Into a homogeneous solution which had been obtained by the reaction with 1.1 g of magnesium and 7.2 g of diethyl malonate in a liquid mixture consisting of 6 ml of ethanol and 50 ml of tetrahydrofuran at −60° C., a solution of the above acid chloride in 15 ml of tetrahydrofuran was added dropwise so that they were reacted. The temperature of the reaction mixture was allowed to rise to room temperature, followed by the distillation of the solvents. To the residue were added 8.5 ml of concentrated hydrochloric acid, 50 ml of water and 100 ml of chloroform, followed by separation into two layers. The chloroform layer was concentrated to obtain an oily residue. 2 g of p-toluenesulfonic acid monohydrate and 60 ml of water were added to the entire amount of the oily residue. They were reacted at about 100° C. for 1.5 hours. The reaction mixture was allowed to cool down, followed by the addition of 150 ml of dichloromethane. The resultant mixture was allowed to separate into two layers. The dichloromethane layer was washed with 1% aq. sodium hydrogencarbonate solution and was then treated with anhydrous magnesium sulfate. The dichloromethane solution was then concentrated, whereby ethyl 6-nitro-2,3,4-trifluorobenzoylacetate was obtained as an oily residue.

12.2 g of the ethyl benzoylacetate was heated to 140° C. along with 12.2 g of acetic anhydride and 9.8 g of ethyl orthoformate. They were reacted for 20 minutes. Excess reagents were distilled off at the same temperature under reduced pressure. The residue was allowed to cool down and then dissolved in 50 ml of dichloromethane. 3.1 g of 3-aminooxetane was added to the resultant solution. The mixture was stirred at room temperature for 10 minutes, followed by distillation of the solvent. To the residue were added 4.8 g of anhydrous potassium carbonate and 50 ml of dimethylformamide, followed by a reaction at 80° C. for 25 minutes. To the reaction mixture were added 200 ml of chloroform and 700 ml of water. The mixture thus formed was shaken. A solid thus precipitated was collected by filtration and then washed successively with water, methanol and chloroform, whereby 5.8 g of ethyl 6,7-difluoro-5-nitro-1-(oxetan-3-yl)-4-oxo-1,4-dihydroquinoline-4-carboxylate was obtained as colorless needle crystals (m.p. 233°-235° C.).

2 g of the ethyl quinolonecarboxylate derivative and 0.2 g of 10% palladium/carbon were added to a liquid mixture which consisted of 100 ml of dichloromethane, 100 ml of methanol and 2 ml of acetic acid. The resultant mixture was hydrogenated overnight. To the reaction mixture were added 100 ml of chloroform and 20 ml of methanol to dissolve a precipitate thus formed. The catalyst was filtered off. The filtrate was concentrated. Colorless needle crystals thus precipitated were collected by filtration and then washed with chloroform, whereby 1.6 g of the title compound was obtained.

Melting point: 272°-275° C. (decomposed).
$^1$H-NMR (CDCl$_3$-CD$_3$OD, 10:1) δ: 1.4(t,J=7Hz,3H), 4.38(q.J=7Hz,2H), 4.95-5.02(m,2H), 5.11-5.19(m,2H), 5.35-5.48(m,1H), 5.94(dd,J=12Hz,6Hz, 1H), 8.42(s,1H).

EXAMPLE 46

5-Amino-6,7-difluoro-1-(oxetan-3-yl)-1,4-dihydro-4-oxoquinoline-3-carboxylic acid (Compound No. 227)

To 20 ml of tetrahydrofuran, 110 mg of Compound No. 226 was added along with 1.5 g of a 10% aqueous solution of tetra-n-butylammonium hydroxide. They were reacted at 60° C. for 10 minutes. To the reaction mixture was added 10 mg of acetic acid and 3 ml of water and then concentrated. A precipitate was collected by filtration and then successively washed with water, ethanol and diisopropyl ether, whereby 44 mg of the title compound was obtained as colorless powdery crystals.

Melting point: ≧300° C.
$^1$H-NMR (DMSO-d$_6$) δ: 4.85-5.13(m,4H), 5.60-5.71(m,1H), 6.41(dd,J=12Hz,6Hz, 1H), 7.95(br.2H), 8.64(s,1H).

EXAMPLE 47

5-Amino-6-fluoro-1-(oxetan-3-yl)-7-(piperazin-1-yl)-1,4-dihydro -4-oxoquinoline-3-carboxylic acid (Compound No. 228)

810 mg of Compound 226 and 810 mg of piperazine were added to 5 g of dimethylsulfoxide and were reacted at about 100° C. for 1 hour. The reaction mixture was cooled to about 80° C., followed by the addition of 325 mg of potassium hydroxide in 2 ml of water. They were reacted for 5 minutes, followed by the addition of 300 mg of acetic acid and 8 ml of ethanol. The resultant mixture was stirred at the same temperature and then allowed to cool down. A precipitate thus formed was collected by filtration and then washed with ethanol and diisopropyl ether. It was recrystallized from chloroform-methanol, whereby 610 mg of the title compound was obtained as pale yellow powdery crystals.

Melting point: 244°-246° C.
$^1$H-NMR (DMSO-d$_6$) δ: 2.82-2.89(m,4H), 3.11-3.21(m,4H), 5.86-5.96(m,2H), 5.99-6.09(m,2H), 5.70-5.79(m,1H), 5.81(d,J=6Hz,1Hz), 7.37(br.s,2H), 8.50(s,1H).

EXAMPLE 48

Compound Nos. 229-232, which are shown in Table 14, were obtained in a similar manner to Example 47.

TABLE 14

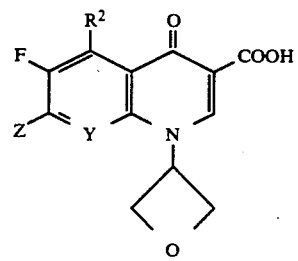

| Comp'd. No. | R$^2$ | Z | Y | Appearance | Melting point (°C.) | [Solvent] $^1$H-NMR | Reaction solvent |
|---|---|---|---|---|---|---|---|
| 229 | —NH$_2$ | —N\_/NCH$_3$ | CH | Pale brown powder | 241-244 | [CDCl$_3$—CD$_3$OD, 10:1]:2.39(s, 3H), 2.58-2.68(m, 4H) 3.25-3.33(m, 4H), 5.00-5.19(m, 4H), 5.47-5.56(m, 1H), 5.66 (d, J=6Hz, 1H), 8.56(s, 1H) | DMSO |

TABLE 14-continued

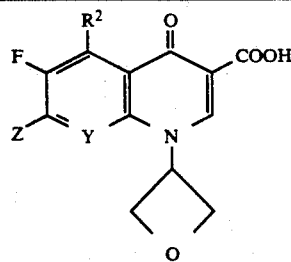

| Comp'd. No. | R² | Z | Y | Appearance | Melting point (°C.) | [Solvent] ¹H-NMR | Reaction solvent |
|---|---|---|---|---|---|---|---|
| 230 | —NH₂ | —N⟨⟩NH with CH₃ | CH | Yellow powder | 228–232 | [DMSO-d₆]:1.03(d, J=6Hz, 3H), 2.80–2.99(m, 3H) 4.85–5.07(m, 4H), 5.71–5.80 (m, 1H), 5.82(d, J=Hz, 1H)7.34(brs, 2H), 8.50(s, 1H) | DMSO |
| 231 | —NH₂ | —N⟨⟩NH₂ | CH | Pale brown powder | 268–271 (Blackened) | [DMSO-d₆]:1.63–1.75(m, 1H), 1.93–2.06 (m, 1H)–3.71(m), 4.84–4.92(m, 2H), 4.99–5.07(m, 2H), 5.42(d, J=6Hz, 1H), 7.20(brs, 2H), 8.40(s, 1H) | DMSO |
| 232 | —NH₂ | —N⟨⟩NH₂ with ""CH₃ (−) | CH | Pale yellow powder | 277–282 (Blackened) | [DMSO-d₆]:1.07(d, J=6Hz, 3H), 2.39–2.54 (m, 1H)–3.89(m), 4.82–5.08(m, 4H), 5.45(d, J=6Hz, 1H), 5.60–5.71(m, 1H), 7.27(brs, 1H), 8.42(s, 1H) | DMSO |

EXAMPLE 49

Ethyl 1-(oxetan-3-yl)-5,7,8-trifluoro-1,4-dihydro-4-oxoquinoline-3-carboxylate (Compound No. 233)

3 g of ethyl 2,3,4,6-tetrafluorobenzoylacetate, 3 g of acetic anhydride and 2.7 g of ethyl orthoformate were reacted at 140° C. for 1.5 hours. At the same temperature, excess reagents were distilled out. The residue was allowed to cool down and then dissolved in 50 ml of dichloromethane. 0.6 g of 3-aminooxetane was added, followed by concentration. 5 ml of diisopropyl ether was added. The resultant mixture was left over. Crystals thus precipitated were collected by filtration. Those crystals were added to 40 ml of tetrahydrofuran, followed by the addition of 280 mg of 60% sodium hydride under stirring and reflux. They were reacted for 10 minutes. After the solvent was distilled off, 100 ml of chloroform and 20 ml of water were added. The resulting mixture was shaken and then allowed to separate into two layers. The chloroform layer was treated with anhydrous magnesium sulfate and concentrated. Colorless crystals thus precipitated were collected by filtration and then washed with diisopropyl ether, whereby 1.97 g of the title compound was obtained.

Melting point: 169°–171° C.

¹H-NMR (CDCl₃) δ: 1.40(t,J-7Hz,3H), 4.39(q,J=7Hz,2H), 4.93–5.04(m,2H), 5.08–5.19(m,2H), 5.73–5.84(m,1H), 6.96(dt,J=6Hz, J=11Hz,1H), 8.53(s,1H).

EXAMPLE 50

1-(Oxetan-3-yl)-5,7,8-trifluoro-1,4-dihydro-4-oxoquinoline-3-carboxylic acid (Compound No. 234)

650 mg of Compound No. 233, 1.2 ml of 2N aq. sodium hydroxide solution and 50 mg of benzyltriethylammonium chloride were added to 20 ml of tetrahydrofuran. The resultant mixture was stirred under reflux for 2.5 hours. A majority of the tetrahydrofuran was distilled off, followed by the addition of 5 ml of ethanol. The resulting mixture was refluxed for 5 minutes and then allowed to cool down, whereby 560 mg of the title compound was obtained as pale brownish yellow powder.

Melting point: >300° C.

¹H-NMR (DMSO-d₆) δ: 4.79–5.03(m,4H), 5.67–5.80(m,1H), 7.40(dt,J=6Hz,11Hz, 1H), 8.55(s,1H).

EXAMPLE 51

5,8-Difluoro-1-(oxetan-3-yl)-7-(piperazin-1-yl)-1,4-dihydro-4-oxoquinoline-3-carboxylic acid (Compound No. 235)

100 mg of Compound No. 234, 100 mg of piperazine and 400 mg of dimethylsulfoxide were stirred at about 100° C. for 20 minutes. To the resultant mixture was added 1 ml of ethanol and then refluxed for 2 minutes. The reaction mixture was allowed to cool down. Pale yellow powdery crystals thus precipitated were collected by filtration and then washed successively with ethanol and chloroform, whereby 60 mg of the title compound was obtained.

Melting point: >300° C.

¹H-NMR (DMSO-d₆) δ: 2.76–2.90(m,4H), 3.14–3.25(m,4H), 4.81–5.05(m,4H), 5.76–5.89(m,1H), 7.12(dd,J=7Hz,14Hz,1H), 8.64(s,1H).

EXAMPLE 52

Ethyl 8-chloro-6,7-difluoro-1-(oxetan-3-yl)-1,4-dihydro-4-oxoquinoline-3-carboxylate (Compound No. 236)

7 g of ethyl 2,3-dichloro-4,5-difluoro-benzyolacetate, 7.5 g of acetic anhydride and 6 g of ethyl orthoformate were reacted at 140° C. for 40 minutes. Excess reagents were distilled off at the same temperature under reduced pressure and the residue was allowed to cool down. The residue was dissolved in 40 ml of dichloromethane, followed by the addition of 1.8 g of 3-aminooxetane. The mixture thus obtained was concentrated. A precipitate was dispersed in chloroform-diisopropyl ether and then collected by filtration. The precipitate was dissolved in 70 ml of tetrahydrofuran, followed by the addition of 640 mg of 60% sodium hydride. The resultant mixture was stirred at 60° C. for 30 minutes. The solvent was distilled off and 150 ml of chloroform and 50 ml of water were added to the residue. The mixture thus obtained was shaken and then allowed to separate into two layers. The chloroform layer was treated with anhydrous magnesium sulfate and then concentrated. Colorless powdery crystals thus precipitated were dispersed in chloroform-diisopropyl ether and then collected by filtration, whereby 3.5 g of the title compound was obtained.

Melting point: 139°–141° C.

$^1$H-NMR (CDCl$_3$) δ: 1.42(t,J=7Hz,3H), 4.42(q,J=7Hz,2H), 4.82–4.91(m,2H), 5.14–5.24(m,2H), 6.01–6.10(m,1H), 8.24(dd,J=10Hz,8Hz,−1H), 8.90(s,1H).

was collected by filtration and then washed successively with ethanol and diisopropyl ether, whereby 650 mg of the title compound was obtained.

Melting point: >300° C.

$^1$H-NMR (CDCl$_3$-CD$_3$OD, 10:1) δ: 4.84–5.93(m,2H), 5.12–5.23(m,2H), 6.07–6.18(m,1H), 8.21(dd,J=10Hz,8Hz,1H), 9.08(s,1H).

EXAMPLE 54

8-Chloro-6-fluoro-7-(4-methylpiperazin-1-yl)-1-(oxetan-3-yl)-1,4-dihydro-4-oxoquinolin-3-carboxylic acid (Compound No. 238)

100 mg of Compound No. 237, 100 mg of N-methylpiperazine and 300 mg of dimethylsulfoxide were reacted at about 100° C. for 15 minutes. The reaction mixture was allowed to cool down and 4 ml of diisopropyl ether was added. The resulting mixture was shaken and the upper layer was decanted with an oily precipitate left behind. To the oily precipitate was added 0.5 ml of ethanol. Colorless prism crystals thus formed were collected by filtration and then washed successively with ethanol and diisopropyl ether, whereby 85 mg of the title compound was obtained.

Melting point: 211°–212° C.

$^1$H-NMR (DMSO-d$_6$) δ: 2.25(s,3H), 2.40–2.54(m,4H), 4.72–4.82(m,2H), 5.04–5.15(m,2H), 6.04–6.15(m,1H), 7.95(d,J=12Hz,1H), 8.98(s,1H).

EXAMPLE 55

Compound Nos. 239 and 240, which are shown in Table 15, were obtained in a similar manner to Example 54.

TABLE 15

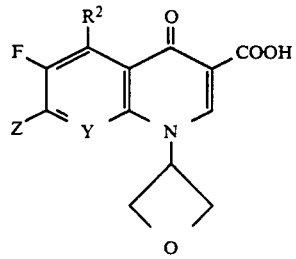

| Comp'd. No. | R$^2$ | Z | Y | Appearance | Melting point (°C.) | [Solvent] $^1$H-NMR | Reaction solvent |
|---|---|---|---|---|---|---|---|
| 239 | H | −N\_\_NH (piperazinyl) | CCl | Colorless powder | 230–233 (Decomposed) | [DMSO-d$_6$]:2.80–2.89(m, 4H), 3.22–3.31(m, 4H) 4.70–4.80(m, 2H), 5.03–5.12(m, 2H), 6.01–6.10 (m, 1H), 7.92(d, J=10Hz, 1H), 8.95(s, 1H) | DMSO |
| 240 | H | −N\_\_NH$_2$ (aminopyrrolidinyl) | CCl | Pale brown powder | 168–175 (Decomposed) | [DMSO-d$_6$]:1.63–1.75(m, 1H), 1.97–2.09(m, 1H) −3.88(m), 4.70–4.80(m, 2H), 5.04–5.14(m, 2H), 5.96–6.07(m, 1H), 8.82(d, J=10Hz, 1H), 8.87 (s, 1H) | DMSO |

EXAMPLE 53

8-Chloro-6,7-difluoro-1-(oxetan-3-yl)-1,4-dihydro-4-oxoquinoline-3-carboxylic acid (Compound No. 237)

To 16 ml of tetrahydrofuran, 900 mg of Compound No. 236 was added along with 1.5 ml of 2N aq. sodium hydroxide solution. They were reacted at 60° C. for 40 minutes. To the reaction mixture was added 200 mg of acetic acid. The resultant mixture was stirred for 10 minutes and then allowed to cool down. A reaction product precipitated in the form of pale yellow powder

EXAMPLE 56

Ethyl 6,7-difluoro-1-(oxetan-3-yl)-1,4-dihydro-8-methyl-4-oxoquinoline-3-carboxylate (Compound No. 241)

2.1 g of ethyl 2-chloro-3-methyl-4,5-difluorobenzoylacetate, 2.0 ml of ethyl orthoformate and 3.4 ml of acetic anhydride were reacted at 130° C. for 4 hours. Volatile components were distilled off under reduced pressure, followed by the addition of 20 ml of benzene.

To the resultant mixture was added at room temperature 0.6 g of 3-aminooxetane. They were reacted at the same temperature for 15 hours. The solvent was distilled off, followed by the addition of hexane. A solid thus formed was collected by filtration (yield: about 2.3 g).

In 8 ml of dimethylformamide, 0.8 g of the solid and 0.32 g of potassium carbonate were reacted at 110° C. for 20 hours. The solvent was distilled off. The residue was extracted with 20 ml of chloroform. After the chloroform solution was washed with water and then dried over MgSO4, the solvent was distilled off. Hexane was added. A solid thus formed was collected by filtration, whereby 0.44 g of the title compound was obtained as a yellow solid.

Melting point: 157°-165° C.

1H-NMR (CDCl3) δ: 1.42(t,J=7.1Hz,3H), 2.41(d,J=2.9Hz,3H), 4.42(q,J=7.1Hz,2H), 4.90-5.20(m,4H), 5.61(m,1H), 8.08(d,J=9.3Hz,1H), 9.07(s,1H).

EXAMPLE 57

6,7-Difluoro-1-(oxetan-3-yl)-1,4-dihydro-8-methyl-4-oxoquinoline-3-carboxylic acid (Compound No. 242)

0.44 g of Compound No. 241 was dissolved in 10 ml of tetrahydrofuran, to which 1 ml of 2N aq. sodium hydroxide solution was added. They were reacted under reflux for 5 hours. After the organic solvent was distilled off, the residue was rendered acidic with 1N HCl. A solid thus formed was collected by filtration. The solid was washed successively with water, ethanol and ether, each in the amount of 1 ml, whereby 0.20 g of the title compound was obtained as a pale brown solid.

Melting point: 193°-202° C.

1H-NMR (CDCl3) δ: 2.50(d,3H), 4.92-5.23(m,4H), 5.77(m,1H), 8.17(d,J=9.16Hz,1H), 9.32(s,1H).

EXAMPLE 58

7-(3-Aminopyrrolidin-1-yl)-6-fluoro-1-(oxetan-3-yl)-1,4-dihydro-8-methyl-4-oxoquinoline-3-carboxylic acid (Compound No. 243)

In 1 ml of DMSO, 100 mg of Compound No. 242 and 85 mg of 3-aminopyrrolidine were reacted at 80° C. for 2 hours. The reaction mixture was washed three times with diisopropyl ether. The residue was solidified with ether and the resultant solid was collected by filtration. The solid was then washed successively with chloroform, ethanol and hexane, each in the amount of 3 ml, whereby 38 mg of the title compound was obtained as a brown solid.

Melting point: ≧230° C. (carbonized)

EXAMPLE 59

Ethyl 5-dimethylamino-6,7,8-trifluoro-1-(oxetan-3-yl)-1,4-dihydro-4-oxoquinoline-3-carboxylate (Compound No. 244)

In 18 ml of toluene, 800 mg of Compound No. 23, 4.6 g of triethylamine and 1.88 g of dimethylamine hydrochloride were stirred at room temperature for 2 hours. After the solvent was distilled off, the residue was subjected to columnchromatography on silica gel (chloroform/acetone=10/1), whereby 790 mg of the title compound was obtained as a yellow solid.

Melting point: 130°-134° C.

1H-NMR (CDCl3) δ: 1.38(t,J=7Hz,3H), 2.98(s,3H), 2.99(s,3H), 4.38(q,7Hz, 2H),4.9-5.0(m,2H), 5.05-5.15(m,2H), 5.55-5.7(m,1H), 8.41(s,1H).

EXAMPLE 60

5-Dimethylamino-6,7,8-trifluoro-1-(oxetan-3-yl)-1,4-dihydro-4-oxoquinoline-3-carboxylic acid (Compound No. 245)

790 mg of Compound No. 244 was dissolved in 15 ml of tetrahydrofuran. Under reflux, 2.5 ml of 1N aq. sodium hydroxide solution was added dropwise. Then, they were then reacted for 30 minutes. After the organic solvent was distilled off, the residue was rendered acidic (about pH 5.0) with 20% acetic acid. A solid thus formed was collected by filtration. The solid was washed successively with water (5 ml×2), methanol (3 ml) and ether (5 ml×2), whereby 433 mg of the title compound was obtained as a yellow solid.

Melting point: 173°-175° C.

1H-NMR (CDCl3) δ: 3.05(s,3H), 3.06(s,3H), 4.86-5.2(m,4H), 5.65-5.8 (m,1H), 8.69(s,1H).

EXAMPLE 61

5-Dimethylamino-6,8-difluoro-7-(4-methylpiperazin-1-yl)-1-(oxetan-3-yl)-1,4-dihydro-4-oxoquinoline-3-carboxylic acid (Compound No. 246)

In 1 ml of dimethylsulfoxide, 100 mg of Compound No. 245 and 100 mg of 1-methylpiperazine were reacted at 80° C. for 1.5 hours. To the reaction mixture was added 150 ml of ether, followed by stirring. After decantation, the residue was solidified with ethanol and ether, each in the amount of 10 ml. A solid thus formed was collected by filtration, whereby 55 mg of the title compound was obtained as a yellow powder.

Melting point: 186°-187° C.

1H-NMR (CDCl3) δ: 2.36(s,3H), 2.54(s,4H), 2.99(s,3H), 3.00(s,3H), 3.37(s,4H), 4.85-4.95(m,2H), 5.0-5.1(m,2H), 5.6-5.75(m,1H), 8.59(s,1H).

EXAMPLE 62

Compound Nos. 247 and 248, which are shown in Table 16, were obtained in a similar manner to Example 61.

TABLE 16

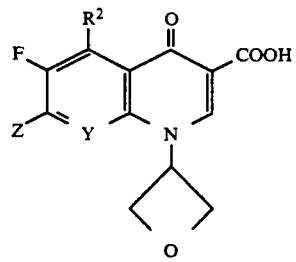

| Comp'd. No. | R² | Z | Y | Appearance | Melting point (°C.) | [Solvent] ¹H-NMR | Reaction solvent |
|---|---|---|---|---|---|---|---|
| 247 | Me—N—Me | H₂N-[azetidinyl]-N— | CF | Yellow powder solid | 150–154 | [CDCl₃ + DMSO-d₆]:1.65–1.9(m, 1H), 2.0–2.25(m, 1H), 2.97(s, 3H), 2.98(s, 3H), 3.3–3.4(m, 1H), 3.55–4.0(m, 4H), 4.8–5.1(m, 4H), 5.55–5.71(m, 1H), 8.55(s, 1H) | DMSO |
| 248 | Me—N—Me | HN[piperazinyl]N— | CF | Yellow powder solid | 150–159 | [CDCl₃ + DMSO-d₆]:2.99(s, 3H), 3.00(s, 3H), 2.8–3.1(br, 4H), 3.37(s, 4H), 4.8–5.15(m, 4H), 5.6–5.8(m, 1H), 8.63(s, 1H) | DMSO |

EXAMPLE 63

Ethyl 6,7,8-trifluoro-1-(thietan-3-yl)-1,4-dihydro-4-oxoquinoline-3-carboxylate (Compound No. 249)

1.32 g of ethyl 2,3,4,5-tetrafluorobenzoylacetate, 1.25 ml of ethyl orthoformate and 2.3 ml of acetic anhydride were reacted at 130° C. for 1 hour. Volatile components were distilled off under reduced pressure. The residue was added with 30 ml of benzene and also with a solution of 623 mg of 3-aminothietane in 5 ml of ethanol. The resultant mixture was stirred at room temperature for 12 hours. The solvent was distilled off and hexane was added to the residue. A solid thus formed was collected by filtration, whereby 1.16 g of a white solid was obtained. In 5 ml of dimethylformamide, 1.16 g of the white solid and 440 mg of potassium carbonate were reacted at 100° C. for 30 minutes. The solvent was distilled off, followed by extraction with 50 ml of chloroform. The organic layer was washed with 10 ml of water and then dried over anhydrous sodium sulfate. The solvent was distilled off. Ether was added to the residue. A solid thus formed was collected by filtration, whereby 785 mg of the title compound was obtained as a pale yellow solid.

Melting point: 160°–164° C.
¹H-NMR (CDCl₃) δ: 1.43(t,J=7Hz,3H), 3.45–3.65(m,2H), 3.8–4.0(m,2H), 4,42(q,J=7Hz,2H), 6.0–6.2(m,1H), 8.08–8.13(m,1H), 8.86(s,1H).

EXAMPLE 64

6,7,8-Trifluoro-1-(thietan-3-yl)-1,4-dihydro-4-oxoquinoline-3-carboxylic acid (Compound No. 250)

750 mg of Compound No. 249 was dissolved in 5 ml of tetrahydrofuran and under reflux, 3 ml of 2N aq. sodium hydroxide solution was added dropwise. They were reacted for 10 minutes. The solvent was distilled off and the residue was acidified to pH 5–4 with 20% acetic acid. A solid thus formed was collected by filtration. The solid was washed successively with water (3 ml×2), ethanol (5 ml×2) and ether (5 ml×2), whereby 690 mg of the title compound was obtained as a slightly red solid.

Melting point: 172°–175° C.
¹H-NMR (CDCl₃) δ: 3.5–3.63(m,2H), 3.8–4.0(m,2H), 6.1–6.3(m,1H), 8.1–8.15(m,1H), 9.09(s,1H).

EXAMPLE 65

6,8-Difluoro-7-(4-methylpiperazin-1-yl)-1-(thietan-3-yl)-1,4-dihydro-4-oxoquinoline-3-carboxylic acid (Compound No. 251)

In 1 ml of dimethylformamide, 60 mg of Compound No. 250 and 100 mg of 1-methylpiperazine were reacted at 80° C. for 40 minutes. The solvent was distilled off. To the residue was added 4 ml of ethanol, so that the residue was solidified. The solid thus obtained was ground and collected by filtration, whereby 41 mg of the title compound was obtained as pale yellow powder.

Melting point: 204°–206° C.
¹H-NMR (CDCl₃) δ: 2.38(s,3H), 2.58(s,4H), 3.44(s,4H), 3.5–3.65(m,2H), 3.85–4.0(m,2H), 6.05–6.15(m,1H), 7.94(d,J=11.7Hz,1H), 8.99(s,1H).

EXAMPLE 66

Compound Nos. 252–256, which are shown in Table 17, were obtained in a similar manner to Example 65.

TABLE 17

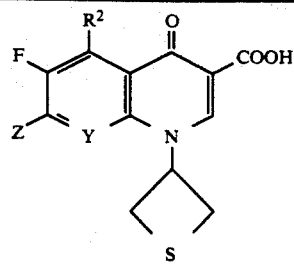

| Comp'd. No. | R² | Z | Y | Appearance | Melting point (°C.) | [Solvent] ¹H-NMR | Reaction solvent |
|---|---|---|---|---|---|---|---|
| 252 | H | O⟨  ⟩N— | CF | Colorless powder | 210–213 | [CDCl₃]:3.41(s, 4H), 3.45–3.6(m, 2H), 3.85(s, 4H), 3.8–4.0(m, 2H), 6.0–6.2(m, 1H), 7.96(d, J=11.7Hz, 1H), 8.99(s, 1H) | DMF |
| 253 | H | S⟨  ⟩N— | CF | Colorless powder | 215–217 | [CDCl₃]:2.81(s, 4H), 3.4–3.6(m, 2H), 3.61(s, 4H), 3.85–4.0(m, 2H), 6.05–6.2(m, 1H), 7.97(d, J=11.5Hz, 1H), 9.01(s, 1H) | DMF |
| 254 | H | H₂N-⟨ ⟩N— | CF | Yellow powder | 215–222 | [DMSO-d₆]:1.6–1.75(m, 1H), 1.9–2.05(m, 1H), 3.8–4.0(m, 2H), 5.9–6.1(m, 1H), 7.69(d, J=13.7Hz, 1H), 8.78(s, 1H) | DMSO |
| 255 | H | HO-⟨ ⟩N— | CF | Yellow powder | 283–287 | [DMSO-d₆]:1.8–2.05(m, 2H), 3.3–3.5(m, 4H), 3.6–3.8(m, 1H), 3.8–4.05 (m, 4H), 4.38(brs, 1H), 5.07(s, 1H) 5.9–6.1(m, 1H), 7.73(d, J=14.2Hz, 1H), 8.82(s, 1H) | DMSO + Et₃N |
| 256 | H | EtNH-CH₂-⟨ ⟩N— | CF | Colorless powder | 210–212 | [DMSO-d₆ + CF₃EtOH]:1.21(t, J=7.3Hz, 3H), 1.6–1.8(m, 1H), 2.05–2.2(m, 1H), 2.8–3.1(m, 4H), 3.4–3.6(m, 3H), 3.7–3.9(m, 3H), 3.95–4.1(m, 2H), 5.85–6.05(m, 1H), 7.75(d, J=14.2Hz, 1H), 8.47(brs, 2H), 8.83(s, 1H) | DMSO + Et₃N |

REFERENTIAL EXAMPLE

Synthesis of 3-Aminothietane (1) 3-Phthalimidoylthietane 14.3 g of 3-hydroxythietane, 418 g of triphenylphosphine and 23.4 g of phthalimide were dissolved in 200 ml of tetrahydrofuran, followed by the dropwise addition of a solution of 27.8 g of diethyl azodicarboxylate in 70 ml of tetrahydrofuran at room temperature over 1 hour. They were reacted for further 12 hours and the solvent was then distilled off. The residue was subjected to columnchromatography on silica gel (chloroform-/ethyl acetate=50:1). Relevant fractions were collected, from which the solvents were distilled off. To the residue was added 300 ml of isopropyl ether. A solid thus formed was collected by filtration, whereby 9.6 g of the title compound was obtained as a slightly yellow solid.

Melting point: 118°–126° C.

¹H-NMR (CDCl₃) δ: 3.5–3.25(m,2H), 4.25–4.4(m,2H), 5.5–5.7(m,1H), 7.65–7.95(m,4H).

(2) 3-Aminothietane

In 30 ml of methanol, 1.53 g of 3-phthalimidoylthietane and 0.29 ml of hydrazine anhydride were reacted for 1 hour under reflux. After the reaction mixture was allowed to cool down 40 ml of ether was added. Insoluble matter was filtered off. The filtrate was distilled under normal pressure. The residue was provided, as was, for subsequent reactions.

EXAMPLE 67

Ethyl 1-(1-diphenylmethylazetidin-3-yl)-6,7-difluoro-1,4-dihydro-4-oxoquinolin-3-carboxylate (Compound No. 257)

4.92 g of ethyl 2,4,5-trifluorobenzoylacetate, 5 ml of ethyl orthoformate and 8.5 ml of acetic anhydride were reacted at 130° C. for 1.5 hours. After volatile components were distilled off, 50 ml of benzene and 4.77 g of 3-amino-1-diphenylmethylazetidine were added. They were reacted at room temperature for 30 minutes. The solvent was distilled off and 25 ml of dimethylformamide and 2.8 g of potassium carbonate were added to the residue. They were reacted at 140° C. for 20 minutes. The solvent was distilled off and 50 ml of hexane was added to the residue. A solid thus formed was collected by filtration and then washed with water (10 ml×2). The solid was dissolved in 50 ml of chloroform. The resultant solution was dried over anhydrous sodium sulfate. The solvent was distilled off, followed by the addition of ether. A solid thus formed was collected by filtration, whereby 9 g of the title compound was obtained as a pale orange solid.

Melting point: 196°-201° C.

$^1$H-NMR (CDCl$_3$) δ: 1.35(t,J=7Hz,3H), 3.3-3.5(m,2H), 3.85-3.95(m,2H), 4.4(q,J=7Hz,2H), 4.42(s,1H), 4.85-5.0(m,1H), 7.05-7.15(m,1H), 7.2-7.5(m,10H), 8.2-8.35(m,1H), 8.61(s,1H).

EXAMPLE 68

1-(1-Diphenylmethylazetidin-3-yl)-6,7-difluoro-1,4-dihydro-4-oxoquinoline-3-carboxylic acid (Compound No. 258)

5.0 g of Compound No. 257 was dissolved in 120 ml of tetrahydrofuran and under reflux, 9.8 ml of 2N aq. sodium hydroxide solution and 13.7 ml of water were added dropwise. They were reacted for 45 minutes. After the reaction mixture was allowed to cool down, the solvent was distilled off and the residue was acidified to pH 4-5 with 20% acetic acid. A solid thus formed was collected by filtration. The solid was washed successively with 3 ml of water, ethanol (5 ml×3) and ether (10 ml), whereby 4.06 g of the title compound was obtained as a pale yellow solid.

Melting point: 245°-247° C.

$^1$H-NMR (CDCl$_3$) δ: 3.3-3.5(m,2H), 4.85-5.0(m,2H), 4.43(s,1H), 5.0-5.1(m,1H), 7.2-7.55(m,11H), 8.25-8.35(m,1H), 8.85(s,1H).

EXAMPLE 69

1-(Azetidin-3-yl)-6,7-difluoro-1,4-dihydro-4-oxoquinoline-3-carboxylic acid hydrochloride (Compound No. 259)

1.0 g of Compound No. 258 was dissolved in 100 ml of tetrahydrofuran, followed by the addition of 0.54 ml of 4N-HCl/dioxane under ice cooling. The resultant mixture was stirred for 30 minutes. The solvent was distilled off and 30 ml of ether was added. 1.01 g of a solid was collected by filtration. 200 mg of the solid was dissolved in 80 ml of methanol, followed by the addition of 40 mg of palladium black. The thus-prepared mixture was stirred at room temperature for 1 day under hydrogen gas. The catalyst was filtered off and the filtrate was concentrated under reduced pressure. To the residue was added 10 ml of ether. A solid thus formed was collected by filtration, whereby 100 mg of the title compound was obtained as slightly yellow solid.

Melting point: ≧250° C. (colored and decomposed).

$^1$H-NMR (DMSO-d$_6$) δ: 4.5-4.7(m,4H), 5.65-5.8(m,1H), 8.0-8.1(dd,J=12.5Hz, J=6.2Hz,1H), 8.29-8.36(dd,J=10.3Hz,J=8.8Hz,1H), 9.0(s,1H).

EXAMPLE 70

1-(Azetidin-3-yl)-6-fluoro-7-(4-methylpiperazin-1-yl)-1,4-dihydro-4-oxoquinoline-3-carboxylic acid (Compound No. 260)

In 500 mg of dimethylformamide, 60 mg of Compound No. 259 and 80 mg of 1-methylpiperazine were reacted at 80° C. for 1 hour. After the solvent was distilled off, 5 ml of ethanol was added to the residue to solidify the latter. The resulting solid was collected by filtration and then washed successively with ethanol (5 ml) and ether (5 ml), whereby 50 mg of the title compound was obtained as a pale yellow solid.

Melting point: >220° C. (decomposed).

$^1$H-NMR (DMSO-d$_6$) δ: 2.2(s,3H), 2.5(brs,4H), 4.0-4.2(m,4H), 5.5-5.7(m,1H), 7.00(d,J=6.8Hz,1H), 7.94(d,J=13.8Hz,1H), 8.8(s,1H).

EXAMPLE 71

Compound Nos. 261-263, which are shown in Table 18, were obtained in a similar manner to Example 70.

TABLE 18

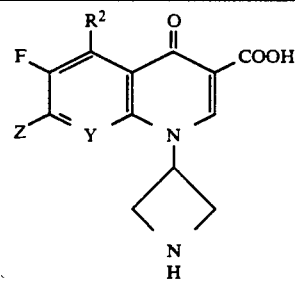

| Comp'd. No. | R$^2$ | Z | Y | Appearance | Melting point (°C.) | [Solvent] $^1$H-NMR | Reaction solvent |
|---|---|---|---|---|---|---|---|
| 261 | H | HN⟨  ⟩N— | CH | Yellow powder | Carbonized (210° C. and up) | [DMSO-d$_6$]:3.12(brs, 4H), 3.42(brs, 4H), 3.9-4.2(m, 4H)5.6-5.7(m, 1H), 7.03-7.10(d, 1H), 7.93-7.98(d, J=12.7Hz, 1H), 8.8(s, 1H) | CHCl$_3$ + Et$_3$N |
| 262 | H | H$_2$N⟨  ⟩N— | CH | Pale brown powder | Carbonized (230° C. and up) |  | CHCl$_3$ + Et$_3$N |
| 263 | H | O⟨  ⟩N— | CH | Pale yellow powder | Carbonized (245° C. and up) |  | CHCl$_3$ + Et$_3$N |

EXAMPLE 72

Ethyl 6,7-difluoro-1-(thietan-3-yl)-1,4-dihydro-4-oxoquinoline-3-carboxylate (Compound No. 264)

2.46 g of ethyl 2,4,5-trifluorobenzoylacetate, 2.5 ml of ethyl orthoformate and 4.2 ml of acetic anhydride were reacted at 130° C. for 3 hours. Volatile components were distilled off under reduced pressure. To the residue were added 40 ml of benzene and a solution of 1.3 g of 3-aminothietane in 20 ml of methanol. The resultant mixture was stirred at room temperature for 12 hours. The solvent was distilled off and 20 ml of hexane was added to the residue. A solid thus formed was collected by filtration, whereby 2.5 g of a pale yellow solid was obtained. In 10 ml of dimethylformamide, 2.5 g of the solid and 1 g of potassium carbonate were stirred at 100° C. for 30 minutes. The solvent was distilled off and the residue was extracted with 100 ml of chloroform. The extract was washed with 20 ml of water. The organic layer was dried over anhydrous sodium sulfate and the solvent was then distilled off. The residue was subjected to columnchromatography on silica gel (chloroform/ethyl acetate=8:1). Relevant fractions were collected, followed by distillation of the solvents. To the residue was added 30 ml of ether. A solid thus formed was collected by filtration, whereby 1.29 g of the title compound was obtained as a colorless solid.

Melting point: 174°–177° C.
$^1$H-NMR (CDCl$_3$) δ: 1.43(t,J=7Hz,3H), 3.54–3.60(dd,J=9.77Hz,J=8.33Hz,2H), 3.90–3.97(dd,J=9.77Hz,J=9.27Hz,2H), 4.42(q,J=7Hz,2H), 5,57–5.75(m,1H), 7.41–7.48(dd,J=11.23Hz,J=5.86Hz,1H), 8.27–8.35(dd,J=10.25Hz,J=8.79Hz,1H), 8.70(s,1H).

EXAMPLE 73

6,7-Difluoro-1-(thietan-3-yl)-1,4-dihydro-4-oxoquinoline-3-carboxylic acid (Compound No. 265)

1.24 g of Compound No. 264 was dissolved in 30 ml of tetrahydrofuran, followed by the addition of 1N aq. sodium hydroxide solution. Under reflux, they were reacted for 20 minutes. The solvent was distilled off under reduced pressure and the residue was neutralized with 20% acetic acid. A solid thus formed was collected by filtration and then washed successively with water (2 ml), ethanol (5 ml×3) and ether (5 ml×2), whereby 970 mg of the title compound was obtained as a pale yellow solid.

Melting point: 251°–256° C.
$^1$H-NMR (CDCl$_3$+DMSO-d$_6$) δ: 3.60–3.68(dd,J=8.3Hz,J=9.76Hz,2H), 3.97(t,J=9.28Hz, 2H), 5.85–6.05(m,1H), 7.84–7.91(dd,J=11.23Hz,J=6.35Hz, 1H), 8.29–8.36(dd,J=8.79Hz,J=9.77Hz,1H), 9.02(s,1H).

EXAMPLE 74

6-Fluoro-7-(4-methylpiperazin-1-yl)-1-(thietan-3-yl)-1,4-dihydro-4-oxoquinoline-3-carboxylic acid (Compound No. 266)

In 0.5 ml of dimethylsulfoxide, 100 mg of Compound No. 265 and 100 mg of 1-methylpiperazine were reacted at 80° C. for 1 hour. The reaction mixture was allowed to cool down, to which 20 ml of ether was added. A solid thus formed was collected by filtration. The solid was washed successively with ethanol (3 ml×3) and ether (3 ml×3), whereby 42 mg of the title compound was obtained as pale yellow powder.

Melting point: 231°–237° C.
$^1$H-NMR (CDCl$_3$) δ: 2.39(s,3H), 2.65(t,J=4.88Hz,4H), 3.38(t,J=4.88Hz,4H), 3.56–3.63(dd,J=8.3Hz,J=9.77Hz,2H),3.96–4.03(dd, J=9.28Hz,J=9.76Hz,2H), 5.7–5.9(m,1H), 7.04(d,J=6.84Hz, 1H),8.06(d,J=13.19Hz,1H), 8.82(s,1H).

EXAMPLE 75

Compound Nos. 267–272, which are shown in Table 19, were obtained in a similar manner to Example 74.

TABLE 19

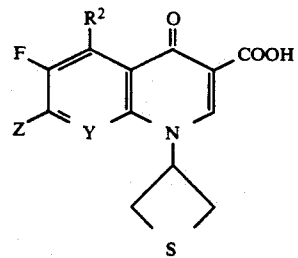

| Comp'd. No. | R$^2$ | Z | Y | Appearance | Melting point (°C.) | [Solvent] $^1$H-NMR | Reaction solvent |
|---|---|---|---|---|---|---|---|
| 267 | H | HN\_\_\_N— | CH | Pale yellow powder | 216–223 | [DMSO-d$_6$]:2.91(brs, 4H), 3.2(brs, 4H), 3.6–3.67(m, 2H), 3.97–4.05 (m, 2H), 6.1–6.35(m, 1H), 7.34(d, J=7.33Hz, 1H), 7.92(d, J=14.16Hz, 1H), 8.81(s, 1H) | DMSO |
| 268 | H | O\_\_\_N— | CH | Colorless powder | 292–296 | [DMSO-d$_6$]:3.35(brs, 4H), 3.55–3.7(m, 2H), 3.80(brs, 4H), 3.9–4.1 (m, 2H), 6.1–6.25(m, 1H), 7.37(d, J=7.32Hz, 1H), 7.95(d, J=13.67Hz, 1H), 8.81(s, 1H) | DMSO |

TABLE 19-continued

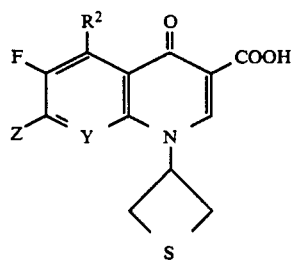

| Comp'd. No. | R² | Z | Y | Appearance | Melting point (°C.) | [Solvent] ¹H-NMR | Reaction solvent |
|---|---|---|---|---|---|---|---|
| 269 | H | S⌐N— (morpholine-like with S) | CH | Colorless powder | 290–295 | [DMSO-d₆]:2.81(brs, 4H), 3.63 (brs, 4H), 3.4–3.65(m, 2H), 3.9–4.1(m, 2H), 6.1–6.3(m, 1H), 7.42 (d, J=6.84Hz, 1H), 7.94(d, J=13.2Hz, 1H), 8.82(s, 1H) | DMSO |
| 270 | H | H₂N-pyrrolidinyl | CH | Pale yellow powder | 270–274 | [DMSO-d₆]:1.65–1.8(m, 1H), 1.95–2.1(m, 1H), 3.4–3.75(m, 6H), 3.94–4.05(m, 2H), 6.02–6.18(m, 1H), 6.84(d, J=7.82Hz, 1H), 7.81 (d, J=14.65Hz, 1H), 8.69(s, 1H) | DMSO |
| 271 | H | H₂N-, Me- pyrrolidinyl Trans (−)-form | CH | Pale yellow powder | 180–186 | [DMSO-d₆]:1.12(d, J=6.35Hz, 3H), 2.4–2.6(m, 1H), 3.5–3.88(m, 4H), 3.9–4.15(m, 2H), 6.05–6.25 (m, 1H), 6.89(d, J=7Hz, 1H), 7.87(d, J=14.16Hz, 1H), 8.72(s, 1H) | DMSO + Et₃N |
| 272 | H | EtNH-CH₂-pyrrolidinyl | CH | Colorless powder | 268–273 | [DMSO-d₆]:1.23(t, J=7.3Hz, 3H), 1.75–1.9(m, 1H), 2.15–2.3(m, 1H), 2.6–2.86(m, 1H), 2.9–3.15(m, 4H), 3.45–3.9(m, 6H), 3.95–4.1(m, 2H), 6.0–6.15(m, 1H), 6.85(d, J=6.84Hz, 1H), 7.85(d, J=14.16Hz, 1H), 8.71(s, 1H) | DMSO + Et₃N |

EXAMPLE 76

Ethyl 7-chloro-6-fluoro-1-(thietan-3-yl)-1,4-dihydro-4-oxo-1,8-naphthyridine-3-carboxylate (Compound No. 273)

2.8 g of ethyl 2,6-dichloro-5-fluoronicotinoylacetate, 2.5 ml of ethyl orthoformate and 4.2 ml of acetic anhydride were reacted at 130° C. for 3 hours. Volatile components were distilled off under reduced pressure. To the residue was added 40 ml of benzene and a solution of 1.3 g of 3-aminothietane in 20 ml of methanol. The resultant mixture was stirred at room temperature for 12 hours. The solvent was distilled off and to the residue was added 20 ml of hexane. A solid thus formed was collected by filtration, whereby 3.02 g of a colorless solid was obtained. 2.95 g of the solid was dissolved in 40 ml of tetrahydrofuran, to which 430 mg of sodium hydride (content: 60%) was added under ice cooling. The resultant mixture was stirred at the same temperature for 30 minutes and then under reflux for further 4 hours. The solvent was distilled off and 20 ml of water was added to the residue. The resultant mixture was extracted with 100 ml of chloroform. The organic layer was dried over anhydrous sodium sulfate and the solvent was distilled off. The residue was subjected to columnchromatography on silica gel (chloroform/ethyl acetate=8:1). Relevant fractions were collected. The solvents was distilled off. To the residue was added 30 ml of ether. A solid thus formed was collected by filtration, whereby 1.11 g of the title compound was obtained as a colorless solid.

Melting point: 157°–161° C.
¹H-NMR (CDCl₃) δ: 1.43(t,J=7.2Hz,3H), 3.54–3.62(dd,J=8.3Hz,J=9.76Hz,2H), 3.86–3.94(dd,J=9.28Hz,J=9.76Hz,2H), 4.43(q,J=7.2Hz, 2H), 6.35–6.55(m,1H), 8.45(d,J=7.33Hz,1H), 8.87(s,1H).

EXAMPLE 77

6-Fluoro-7-(4-methylpiperazin-1-yl)-1-(thietan-3-yl)-1,4-dihydro-4-oxo-1,8-naphthyridine-3-carboxylic acid (Compound No. 274)

In 10 ml of chloroform, 100 mg of Compound No. 273 and 100 mg of 1-methylpiperazine were reacted for 3 hours under reflux. After the reaction mixture was allowed to cool down, the solvent was distilled off under reduced pressure. To the residue was added 5 ml of ethanol and 2 ml of 10% aq. sodium carbonate solution. The resultant mixture was stirred under reflux for 4 hours. After the reaction mixture was allowed to cool down, the solvent was distilled off under reduced pressure. The residue was neutralized with 20% acetic acid. A solid thus formed was collected by filtration and then washed successively with ethanol (3 ml×2) and ether (3 ml×2), whereby 82 mg of the title compound was obtained as pale yellow powder.

Melting point: 270°–280° C.

$^1$H-NMR (DMSO-d$_6$) δ: 2.57(s,3H), 3.03(brs,4H), 3.35-3.55(m,2H), 3.9-4.2 (br,4H), 4.21(brs,2H), 6.1-6.25(m,1H), 8.18(d,J=14.16Hz,1H), 8.87(s,1H).

EXAMPLE 78

Compound Nos. 275-281, which are shown in Table 20, were obtained in a similar manner to Example 77.

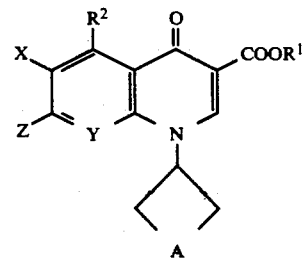

TABLE 20

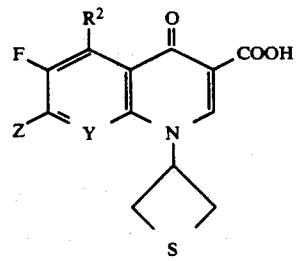

| Comp'd. No. | R² | Z | Y | Appearance | Melting point (°C.) | [Solvent] ¹H-NMR | Reaction solvent |
|---|---|---|---|---|---|---|---|
| 275 | H | HN⌒N— (piperazine) | —N= | Colorless powder | ≧270 Colored ≧300 | [DMSO-d$_6$]:3.17(brs, 4H), 3.3-3.7(m, 2H), 4.02(brs, 4H), 4.1-4.35(m, 2H), 6.05-6.35(m, 1H), 8.14(d, J=12.7Hz, 1H), 8.86(s, 1H) | CHCl$_3$ |
| 276 | H | O⌒N— (morpholine) | —N= | Colorless powder | 280-285 | [DMSO-d$_6$]:3.3-3.6(m, 2H), 3.79(brs, 4H), 3.89(brs, 4H), 4.05-4.25(m, 2H), 6.1-6.25(m, 1H), 8.12(d, J=12.2Hz, 1H), 8.85(s, 1H) | CHCl$_3$ |
| 277 | H | S⌒N— (thiomorpholine) | —N= | Pale yellow powder | 274-283 | [DMSO-d$_6$]:2.8(brs, 4H), 3.35-3.6(m, 2H), 4.02-4.35(m, 6H), 6.05-6.25(m, 1H), 8.11(d, J=13.67Hz, 1H), 8.84(s, 1H) | CHCl$_3$ |
| 278 | H | H$_2$N⌒(R)-pyrrolidinyl | —N= | Pale yellow powder | ≧260 Colored and decomposed | [DMSO-d$_6$]:1.8-2.05(m, 1H), 2.05-2.25(m, 1H), 3.4-4.1(m, 6H), 4.12-4.4(m, 2H), 6.0-6.2(m, 1H), 7.97(d, J=13Hz, 1H), 8.73(s, 1H) | CHCl$_3$ + Et$_3$N |
| 279 | H | H$_2$N⌒(S)-pyrrolidinyl | —N= | Pale yellow powder | ≧260 Colored and decomposed | [DMSO-d$_6$]:1.8-2.0(m, 1H), 2.0-2.25(m, 1H), 3.4-4.1(m, 6H), 4.1-4.4(m, 2H), 6.0-6.25(m, 1H), 7.95(d, J=12Hz, 1H), 8.73(s, 1H) | CHCl$_3$ + Et$_3$N |
| 280 | H | H$_2$N, Me-pyrrolidinyl Trans (−) form | —N= | Pale yellow powder | ≧270 Colored ≧300 | [DMSO-d$_6$]:1.05(d, J=7.3Hz, 3H), 2.2-2.45(m, 1H), 3.7-4.05(m, 3H), 4.1-4.25 (m, 2H), 6.0-6.35(m, 1H), 7.99(d, J=13.2Hz, 1H), 8.76(s, 1H) | CHCl$_3$ + Et$_3$N |
| 281 | H | HN⌒N— Me (methylpiperazine) | —N= | Colorless solid | 260-270 | [DMSO-d$_6$]:1.24(d, 3H), 2.95-3.6(m, 7H), 4.15-4.35(m, 2H), 4.45-4.7(m, 2H), 6.1-6.25(m, 1H), 8.15(d, J=13.7Hz, 1H), 8.87(s, 1H) | CHCl$_3$ + Et$_3$N |

We claim:
1. A quinolone derivative represented by the following formula (1) or a salt thereof; wherein R¹ is a hydrogen atom or a carboxyl-protecting group; R² is a hydrogen atom or halogen atom or a hydroxyl, lower alkoxyl, amino, phenyl lower alkyl, or mono- or di-(lower alkyl)amino group; A represents an oxygen atom; X is a hydrogen or halogen atom; Y represents C—R$^4$, in which R$^4$ is a hydrogen atom, halogen atom, low alkyl or lower alkoxyl group; and Z denotes a group of the formula:

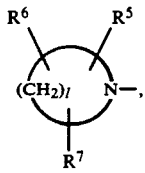

wherein R$^5$, R$^6$ and R$^7$ are the same or different and each individually is a hydrogen atom or halogen atom or a hydroxyl, amino, lower alkyl group; or a group selected from the group consisting of unsubstituted mono- or di-(lower alkyl)amino, mono-or-di-(lower alkyl)amino substituted by phenyl, hydroxyl, lower alkoxyl, and halogen, cyclo(lower alkyl) amino-lower alkyl, mono- and di-(lower alkyl)-amino-lower alkyl, cyclo(lower alkyl)amino-lower alkyl substituted by hydroxyl and phenyl, mono-or-di-(lower alkyl)amino-lower alkyl substituted by hydroxyl and phenyl; unsubstituted lower alkoxyl, lower alkoxyl substituted by halogen and lower alkoxyl; or lower acyloxy, lower alkylthio, phenyl, cyano-lower alkyl, lower acylamino, lower alkoxycarbonyl, aminocyclo-lower alkyl, acylamino-lower alkyl, lower alkoxycarbonylamino-lower alkyl, hydroxy-lower alkyl, lower alkoxy-lower alkyl, lower alkenyl, cyano, mercapto or lower alkylimidoylamino group; and l is 3, 4 or 5.

2. The derivative of claim 1, wherein in the formula—CR$^4$, R$^4$ is a hydrogen or halogen atom.

3. The derivative of claim 1, wherein R$^1$ is a hydrogen atom, X is a halogen atom and R$^2$ is a hydrogen atom or amino group.

4. The derivative of claim 1, which is 5-amino-7-(3-amino-4-methylpyrrolidin-1-yl)-6,8-difluoro-1-(oxetan-3-yl)-1,4-dihydro-4-oxoquinoline-3-carboxylic acid.

* * * * *

UNITED STATES PATENT AND TRADEMARK OFFICE
CERTIFICATE OF CORRECTION

PATENT NO. : 5,245,037
DATED : SEPTEMBER 14, 1993
INVENTOR(S) : TASUHIRO KURAMOTO ET AL

It is certified that error appears in the above-identified patent and that said Letters Patent is hereby corrected as shown below:

Column 152, line 2, "cyclo(lower alkyl)amino-lower alkyl" should read --mono- and di(lower alkyl)-amino-lower alkyl--.

Signed and Sealed this

Twenty-second Day of August, 1995

*Attest:*

BRUCE LEHMAN

*Attesting Officer*     *Commissioner of Patents and Trademarks*